US008748384B2

(12) United States Patent
Andersen et al.

(10) Patent No.: US 8,748,384 B2
(45) Date of Patent: *Jun. 10, 2014

(54) MODULATION OF ACTIVITY OF PRONEUROTROPHINS

(75) Inventors: Olav Michael Andersen, Skamby (DK); Anders Nykjaer, Risskov (DK)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/448,422

(22) PCT Filed: Dec. 21, 2007

(86) PCT No.: PCT/DK2007/000567
§ 371 (c)(1),
(2), (4) Date: Mar. 29, 2010

(87) PCT Pub. No.: WO2008/074329
PCT Pub. Date: Jun. 26, 2008

(65) Prior Publication Data
US 2010/0210523 A1  Aug. 19, 2010

Related U.S. Application Data

(60) Provisional application No. 60/880,771, filed on Jan. 16, 2007.

(30) Foreign Application Priority Data

Dec. 21, 2006 (DK) ................................. 2006 01692

(51) Int. Cl.
*A01N 37/18* (2006.01)
*A61K 39/395* (2006.01)

(52) U.S. Cl.
USPC ....... 514/17.7; 514/18.2; 514/18.3; 514/21.2; 424/130.1; 424/143.1

(58) Field of Classification Search
None
See application file for complete search history.

(56) References Cited

U.S. PATENT DOCUMENTS

| | | | |
|---|---|---|---|
| 5,516,772 A | 5/1996 | Glicksman et al. | |
| 6,011,004 A | 1/2000 | Kessler et al. | |
| 6,291,247 B1 | 9/2001 | Riopelle et al. | |
| 6,300,327 B1 | 10/2001 | Knusel et al. | |
| 6,333,310 B1 | 12/2001 | Presta et al. | |
| 6,417,159 B1 | 7/2002 | Riopelle et al. | |
| 8,066,997 B2* | 11/2011 | Nykjaer et al. | 424/139.1 |
| 8,460,657 B2* | 6/2013 | Nykjaer et al. | 424/139.1 |
| 2001/0064695 | 11/2001 | Hadcock | |
| 2006/0216292 A1* | 9/2006 | Hopf | 424/145.1 |
| 2007/0264195 A1 | 11/2007 | Nykiaer et al. | |

FOREIGN PATENT DOCUMENTS

| | | | |
|---|---|---|---|
| EP | 0994188 A1 | 4/2000 | |
| EP | 1891966 A1 | 2/2008 | |
| WO | 9846254 A1 | 10/1998 | |
| WO | 0044396 A1 | 8/2000 | |
| WO | 0149313 A1 | 7/2001 | |
| WO | 02096356 A2 | 12/2002 | |
| WO | 2004049901 A2 | 6/2004 | |
| WO | 2004053093 A2 | 6/2004 | |
| WO | 2004056385 A2 | 7/2004 | |
| WO | WO 2004/056385 A * | 7/2004 | ............. A61K 38/18 |
| WO | 2005044293 A2 | 5/2005 | |

OTHER PUBLICATIONS

Airaksinen and Saarma; "The GDNF family: Signalling. Biological functions and therapeutic value"; Nature Reviews—Neuroscience; 3:383-394 (2002).
Antonelli et al.; "Neurotensin Enhances Glutamate Excitotoxicity in Mesencephalic Neurons in Primary Culture"; Journal of Neuroscience Research; 70:766-773 (2002).
Appel, S.H.; "A Unifying Hypothesis for the Cause of Amyotrophic Lateral Sclerosis, Parkinsonism, and Alzheimer's Disease"; Ann. Neurol. 10:499-505 (1981).
Arshaysky, Y.I.; "Alzheimer's disease, brain immune privilege and memory: a hypothesis"; J. Neural Transm.; 113:1697-1707 (2006).
Ballabh, et al.; "The blood-brain barrier: an overview. Structure, regulation and clinical implications"; Neurobiology of Disease; 16:1-13 (2004).
Bibel, et al.; "Biochemical and functional interactions between the neurotrophin receptors trk and p75NTR"; The EMBO Journal; 18(3):616-622 (1999).
Bickel, Ulrich; "Antibody delivery through the blood-brain barrier"; Advanced Drug Delivery Reviews; 15:53-72 (1995).
Bigner, et al.; "Phase I studies of treatment of malignant gliomas and neoplastic meningitis with 131 I-radiolabeled monoclonal antibodies anti-tenascin 81C6 and anti-chondroitin proteoglycan sulfate Mel-14 F(ab')2—a preliminary report."; Journal of Neuro-Oncology 24:109-122 (1995).
Boules et al., "Antiparkinson-like effects of a novel neurontensin analog in unilaterally 6-hydroxydopamine lesioned rats", European Journal of Pharmacology 428: 227-233 (2001).
Buhler A V et al.; "Neurotensin activation of the NTR1 on spinally-projecting serotonergic neurons in the rostral ventromedial medulla is antinocieptive"; Pain, 114(1-2):285-294, XP004759800, ISSN 0304-3959 (Mar. 1, 2005).
Chao, Moses and Mark Bothwell "Neurotrophins: to cleave or not the cleave"; Neuron 33:9-12 (Jan. 3, 2002).

(Continued)

*Primary Examiner* — Olga N Chernyshev
(74) *Attorney, Agent, or Firm* — Mary Catherine Di Nunzio

(57) ABSTRACT

The present invention provides agents for inhibiting binding of a pro-neurotrophin to a Vps1 Op-domain receptor, in particular the binding of a pro-NGF or a pro-BDNF to a Sortilin receptor. The invention thus provides agents for the manufacture of a medicament, for treating and/or preventing disease or disorders such as but not limited to neurological, neuropsychiatric and ocular diseases, disorders, and degeneration as well as obesity, diabetes, pain and/or nociception in an individual.

9 Claims, 22 Drawing Sheets

(56) References Cited

OTHER PUBLICATIONS

Chao, Moses V.; "Neurotrophin Receptors: A Window into Neuronal Differentiation"; Neuron; 9:583-593 (1992).

Chao, Moses V.; "Neurotrophins and their receptors: a convergence point for many signaling pathways"; Nature Reviews—Neuroscience; 4:299-309 (2003).

Chen, et al.; "The proNGF-p75 NTR-sortilin Signalling complex as new target for the therapeutic treatment of Parkinson's Disease"; CNS & Neurological Disorders Drug Targets; 7:512-523 (2008).

DeBoer,and Gaillard; Blood-brain barrier dysfunction and recovery.; Journal of Neural Transmission; 113:455-462 (2006).

Dechant, George; "Molecular interactions between neurotrophin receptors"; Cell Tissue Res 305:229-238; (2001).

Duman et al.; "A Molecular and Cellular Theory of Depression"; Arch. Gen. Psychiatry 54:597-606 (1997).

Fahnestock, Margaret et al.; "The Precursor Pro-Nerve Growth Factor is the Predominant Form of Nerve Growth Factor in Brain and Is Increased in Alzheimer's Disease"; Molecular and Cellular Neuroscience 18:210-220, XP002294169, ISSN: 1044-7431 (Aug. 1, 2001).

Fan, et al.; "Differential effects of pro-BDNF on sensory neurons after sciatic nerve transection in neonatal rats"; European Journal of Neuroscience 27:2380-2390 (2008).

Frenchand Tschopp; "Protein-based therapeutic approaches targeting death receptors"; Cell Death and Differentiation; 10:117-123 (2003).

Friden, et al.; "Anti-transferrin receptor antibody-drug conjugates cross the blood-brain barrier"; Proc. Natl. Acad. Sci. USA 88:4771-4775 (1991).

Hampe, Wolfgang et al.; "The genes for the human VPS10 domain-containing receptors are large and contain many small exons"; Human Genetics 108:529-536, (2001).

Hempstead, Barbara L.; "The many faces of p75NTR"; Curr Opin. Neurobiol, 12(3):260-7 (Jun. 2002).

Jacobsen et al.; "Molecular characterization of a novel human hybrid-type receptor that binds the α2-macroglobulin receptor-associated protein" J. Biol. Chem. 271(49):31379-31383 (Dec. 6, 1996).

Jacobsen et al.; "Activation and Functional Characterization of the Mosaic Receptor SorLA/LR11", J. Biol. Chem. 271 (25):22788-22796 (Jun. 22, 2001).

Lashford, et al.; "A pilot study of 131 I monoclonal antibodies in the therapy of leptomeningeal tumors"; Cancer 61: 857-868 (1988).

Lee, et al. "Regulation of cell survival by secreted proneurotrophins". Science 294:1945-1948 (Nov. 3, 2001).

Lee, et al.; "The uniqueness of being a neurotrophin receptor"; Curr. Opin. Neurobiol. 11: 281-286 (2001).

Lin et al.; "Sortilin is a major protein component of Glut4-containing vesicles"; Journal of Biological Chemistry, 272 (39): 24145-47 (1997).

Mazella et al.; "The 100-kDa neurotensin receptor is gp95/sortilin, a non-G-Protein-coupled receptor";.J.Biol. Chem. 273: 26273-26276 (Oct. 9, 1998).

Mazella J.; "Sortilin/neurotensin receptor-3: a new tool to investigate neurotensin signaling and cellular trafficking?" Cellular Signalling, 13:1-6, (Jan. 2001).

Miller, F.D. and D.R. Kaplan; "Neurotrophin signalling pathways regulating neuronal apoptosis"; Cell. Mol. Life Sci. 58, 1045-1053 (2001).

Munck Petersen et al. "Propeptide cleavage conditions sortitlin/neurotensin receptor-3 for ligand binding"; the EMBO Journal 18 (3):595-604 (1999).

Neet, K.E. and R.B. Campenot; "Receptor binding Internalization, and retrograde transport of neurotrophic factors"; Cell. Mol. Life Sci. 58:1021-1035 (2001).

Neuwelt, Edward A.; "Mechanisms of disease: the blood-brain barrier"; Neurosurgery 54:131-142 (2004).

Nielsen et al.; "Sortilin/Neurotensin Receptor-3 Binds and Mediates Degradation of Lipoprotein Lipase", The Journal of Biological Chemistry, 274 (13):8832-8836 (Mar. 26, 1999).

Nielsen et al.; "The sortilin cytoplasmic tail conveys Golgi-endosome transport and binds the VHS domain of the GGA2 sorting protein"; The EMBO Journal, 20 (9):2180-2190 (2001).

Nykjaer et al.; "p75NTR—live or let die"; Current Opinion in Neurobiology, 15:49-57 (2005).

Nykjaer, et al.; "Sortilin is essential for proNGF-induced neuronal cell death"; 427:843-848, XP002286438, ISSN: 0028-0836 (Feb. 26, 2004).

Pardridge, William M.; "Drug targeting to the brain"; Pharmaceutical Research 24(9):1733-1744 (Sep. 2007).

Petersen et al.; "Molecular identification of a novel candidate sorting receptor purified from human brain by receptor-associated protein"; J. Biol. Chem. 272:3599-3605 (Feb. 7, 1997).

Raffioni et al.; "The Receptors for Nerve Growth Factor and other Neurotrophins"; Ann. Rev. Biochem. 62:823-850 (1991).

Rattenholl et al.; "The pro-sequence facilitates folding of human nerve growth factor from *Escherichia coli* inclusion bodies"; Eur. J. Biochem. 268:3296-3303 (2001).

Rubenstein, et al.; "Rituximab therapy for CNS lymphomas: targeting the leptomeningeal compartment"; Blood, 101 (2):466-468 (2003).

Rubin and Staddon; "The cell biology of the blood-brain barrier"; Annu.Rev Neurosci. 22:11-28 (1999).

Shapiro et al., "l-chTNT-1/B mAb" tumour necrosis therapy for malignant astrocytic glioma, Expert Opinion in Biological Therapy, 6(5):539-545 (2006).

Shirayama et al.; "Brain-derived neurotrophic factor produces antidepressant effects in behavioral models of depression"; J. Neurosci. 22: 3251-3261 (Apr. 15, 2002).

Thoenen; "The changing scene of neurotrophic factors"; Trends Neurosci. 14:165-170 (1991).

Triguero, et al.; "Blood-brain barrier transport of cationized immunoglobulin G: enhanced delivery compared to native protein"; Proc. Natl. Acad. Sci. USA 86: 4761-4765 (1989).

Volosin, et al. "Interaction of survival and death signaling in basal forebrain neurons: roles of neurotrophin and proneurotrophins." The Journal of Neuroscience 26(29):7756-7766 (2006).

Beattie, M. S. et al., Oct. 24 2002, ProNGF Induces p75-Mediated Death of Oligodendrocytes following Spinal Cord Injury, Neuron, 36(3):375-86.

Bronfman F. C. and Fainzilber M., 2004, Multi-tasking by the p75 neurotrophin receptor: sortilin things out?, EMBO Reports, 5(9):867-871 (2004).

Harrington, A. W. et al., Apr. 20, 2004, Secreted proNGF is a pathophysiological death-inducing ligand after adult CNS injury, PNAS; 101(16): 6226-6230.

Pelaprat, D., 2006, Interactions between neurotensin receptors and G proteins, Peptides, 27(10):2476-2487.

Al-Shawi, R. et al. (2007) "*ProNGF, Sortilin, and Age-related Neurodegeneration*," Ann. N.Y. Acad. Sci. 1119:208-215.

Angelo, M.F. (2009) "*p75 NTR Expression is Induced in Isolated Neurons of the Penumbra After Ischemia by Cortical Devascularization*," J. Neurosci. Res. 87(8):1892-1903.

Arévalo, J.C. et al. (2006) "*Neurotrophin Signaling: Many Exciting Surprises!*" Cell. Mol. Life Sci. 63:1523-1537.

Arnett, M.G. et al. (2007) "*Pro-NGF, Sortilin, and P75ntr: Potential Mediators of Injury-Induced Apoptosis in the Mouse Dorsal Root Ganglion*," Brain Res. 1183:32-42.

Chen, L.W. et al. (2008) "*The ProNGF-P75ntr-Sortilin Signalling Complex As New Target for the Therapeutic Treatment of Parkinson's Disease*," CNS Neurol. Disord. Drug Targets. 7(6):512-523.

Diarra, A. et al. (2009) "*Signaling of the Neurotrophin Receptor P75 in Relation to Alzheimer's Disease*," Biochem. Biophys. Res. Commun. 390:352-356.

Kitabgi, P. (2002) "*Target Neurotensin Receptors With Agonists and Antagonists for Therapeutic Purposes*", Curr. Opin. Drug Discovery & Development 5(5):764-776.

Longo, F.M. et al. (2004) "*Neurotrophin-Based Strategies for Neuroprotection*," J. Alzheimers Dis. 6(6 Suppl):S13-S17.

Longo, F.M. et al. (2005) "*Neurotrophin Receptor-Based Strategies for Alzheimer's Disease*," Curr. Alzheimer Res. 2(2):167-169.

(56) References Cited

OTHER PUBLICATIONS

Masoudi, R. et al. (2009) "*Biological Activity of Nerve Growth Factor Precursor Is Dependent Upon Relative Levels of Its Receptors*," J. Biol. Chem. 284(27):18424-18433.

Massa, S.M. et al. (2003) "*Alzheimer's Therapeutics*'," J. Molec. Neurosci. 20:323-326.

Miller, F.D. et al. (2001) "Neurotrophin signaling pathways regulating neuronal apoptosis" Cell. Mol. Life Sci. 58, 1045-1053.

Mufson, E.J. et al. (2010) "*Preservation of Cortical Sortilin Protein Levels in MCI and Alzheimer's Disease*," Neurosci. Lett. 471(3):129-133).

Nykjaer, A. et al. (2012) "*Sortilin: A Receptor to Regulate Neuronal Viability and Function*," Trends in Neurosciences 35(4):261-270.

Prabakaran, T. et al. (2011) "*Receptor-Mediated Endocytosis of A-Galactosidase A in Human Podocytes in Fabry Disease*," PLoS One. 2011;6(9):e25065:1-11.

Provenzano, M.J. et al. (2011) "*p75 (NTR) Expression and Nuclear Localization of p75(NTR) Intracellular Domain in Spiral Ganglion Schwann Cells Following Deafness Correlate With Cell Proliferation*," Mol. Cell. Neurosci. 47(4):306-315.

Tauris, J. et al. (2011) "*Proneurotrophin-3 May Induce Sortilin-Dependent Death in Inner Ear Neurons*," Eur. J. Neurosci. 33(4):622-631.

Vincent, J.-P., et al. (1999) "*Neurotensin and Neurotensin Receptors*"; TiPS. 20(7):302-309.

Wiesmann, C. et al. (2001) "*Nerve Growth Factor: Structure and Function*" Cell. Mol. Life Sci. 58:758-759.

Wilcox, et al. (2003) "*Intracranially Administered Anti-Aβ Antibodies Reduce B-Amyloid Deposition by Mechanisms Both Independent of and Associated With Microglial Activation*" J. Neuroscience 23(9):3745-3751.

Yano, et al. (2000) "*Neurotrophin Receptor Structure and Interactions*" Pharmaceutica Acta Helvetiae 74:253-260.

Prabakaran, T. et al. (2012) "*Uptake of A-Galactosidase A in Human Glomerular Podocytes Is Mediated by Various Receptors in Fabry Disease*," Clin. Ther. 34(4S):e28 (1 page).

Hill, R.J. (2002) "*Double Patenting Simplified*" www.cabic.com/ejc/BCPCP100802/RHill_DP.ppt pp. 1-66.

\* cited by examiner

Fig. 2
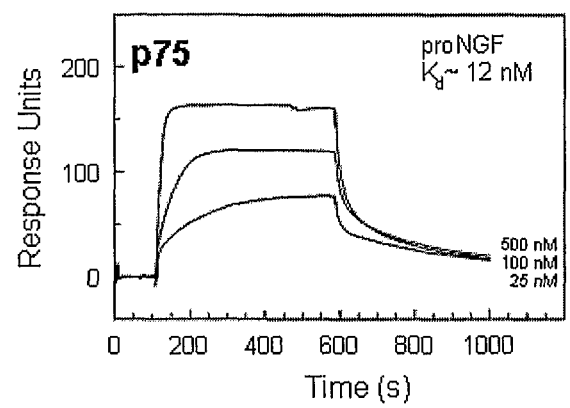
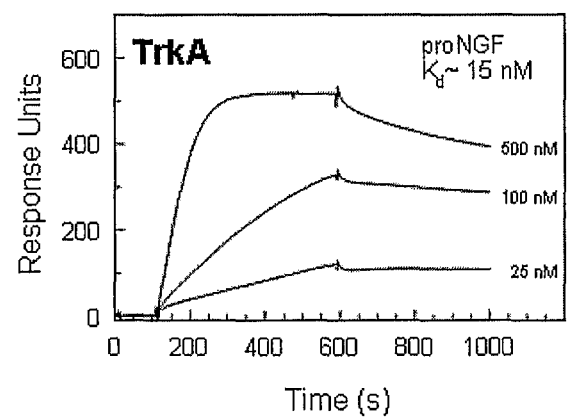
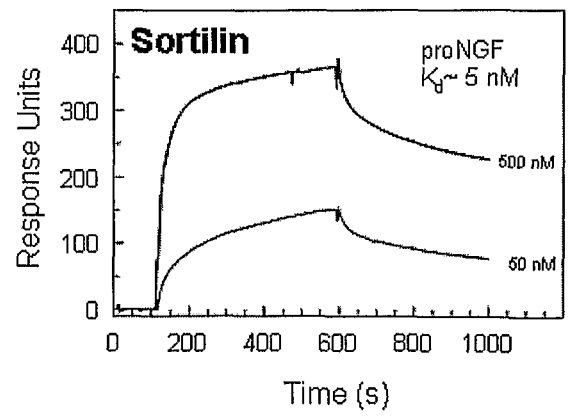

Fig. 3
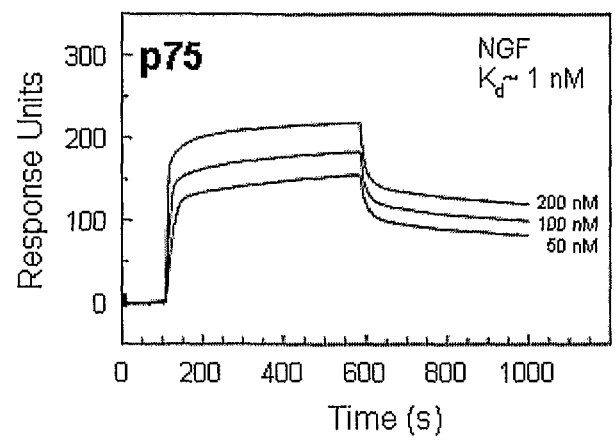
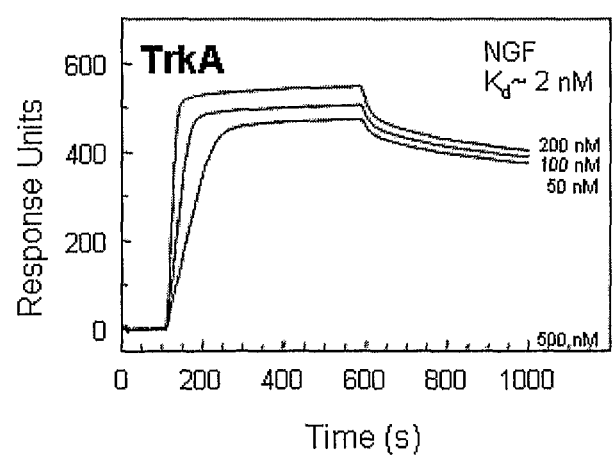
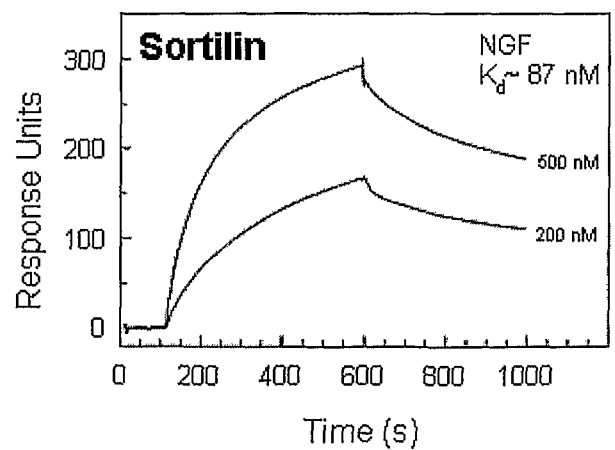

Fig. 4
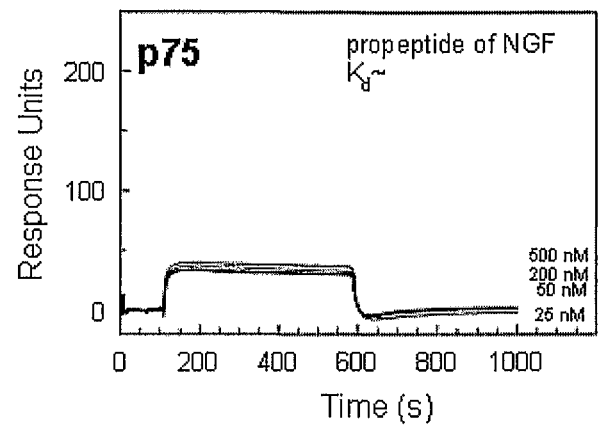
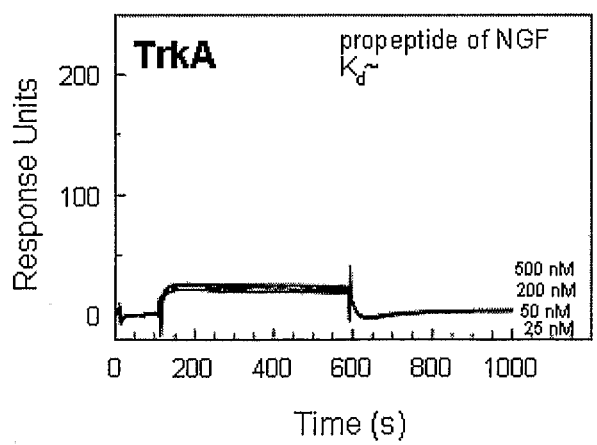
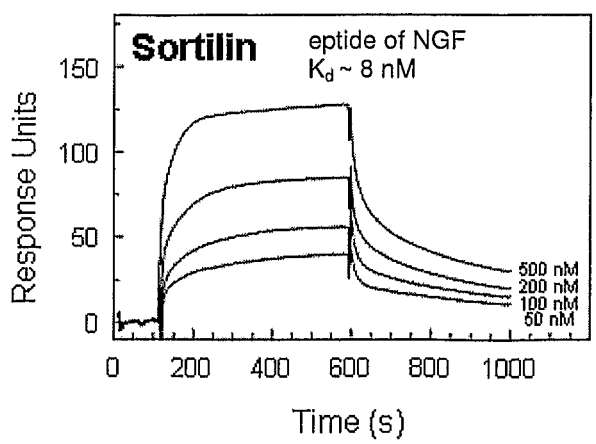

Fig. 6
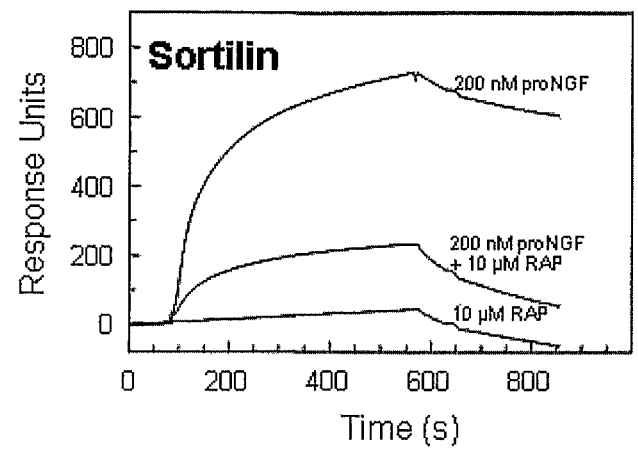
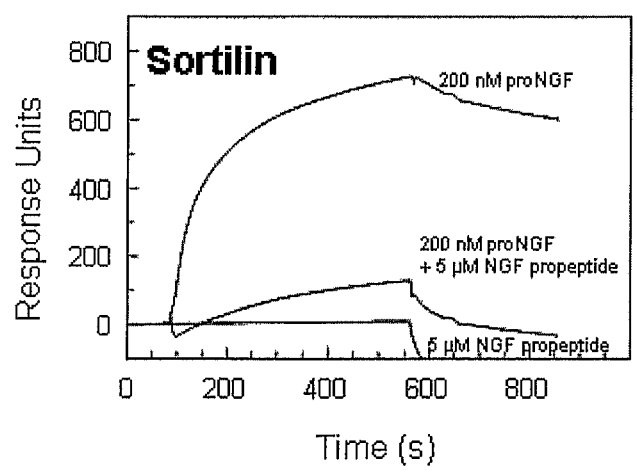
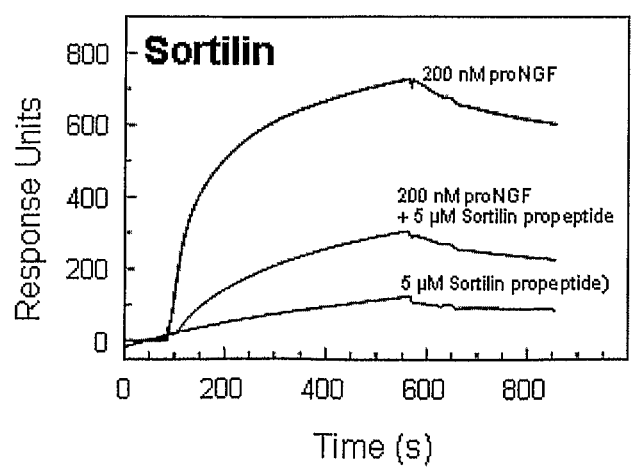

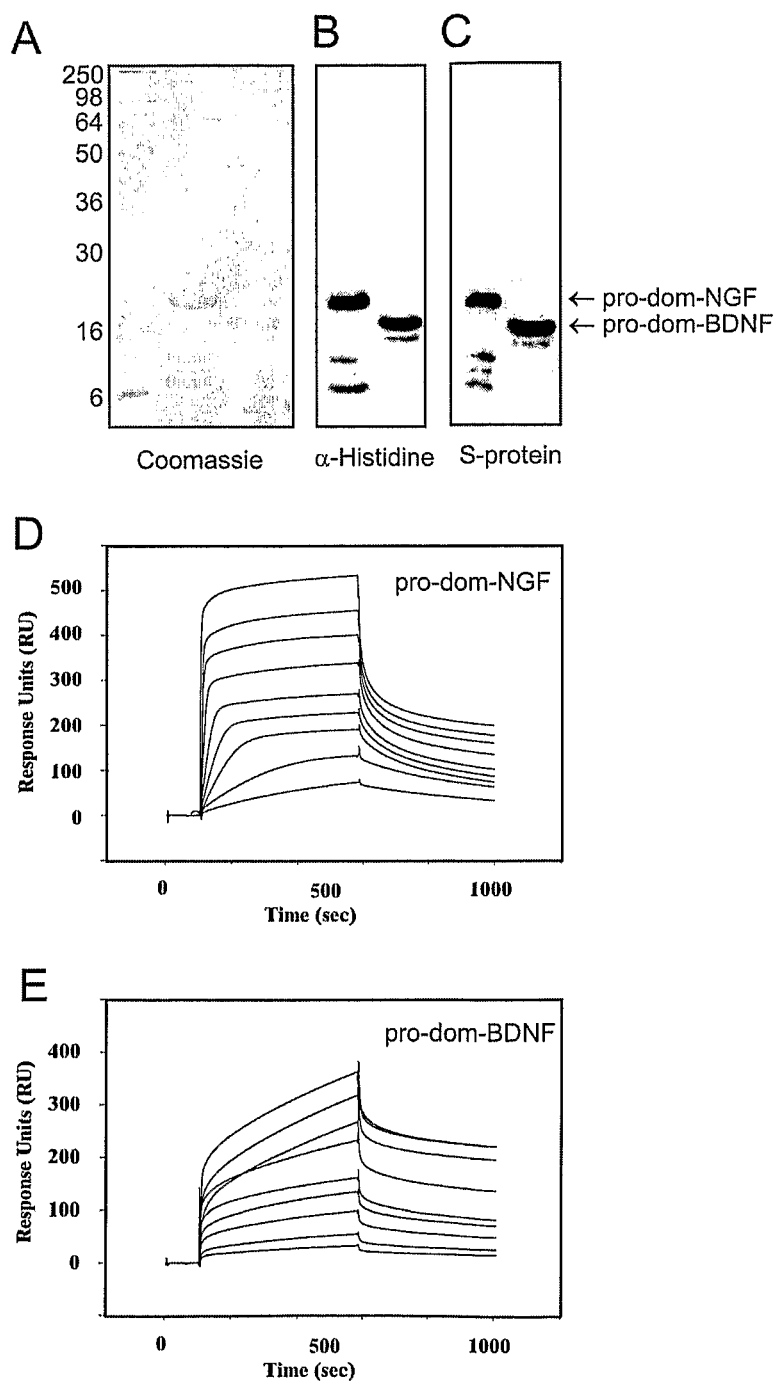

Fig. 9

Pro-domains/immature regions

| SEQ ID NO. | | | | | | | |
|---|---|---|---|---|---|---|---|
| NGF | 6 | 1 | .......... | .......... | .......... | .EPHSESN.V | PAGH..IIPQ AHWTKLQHSL DTALRRARSA PAAA...... 40 |
| BDGF | 7 | 1 | .......... | .......... | .......... | APMKEAN.I | RGQGGLAYPG VRTHGTLESV NGPKAGSRGL TSLADTEHV 48 |
| NT3 | 8 | 1 | NNMDQRSLPE | DSINSLIIKL | IQADILKNKL | SKQMVDVKEN | YQSTLPKAEA PREPERGGPA .KSAFQPVIA 69 |
| NT4/5 | 9 | 1 | .......... | .......... | .......... | .......... | ..........Q PF.PSTLPPF 10 |
| NGF | 6 | 41 | IAA..RVAGQ | TRNITVDPRL | FKKRRLRSPR | VLFSTPQRE | AADTQDLDFE VGGAAPFNRT HRSKR..... 103 |
| BDGF | 7 | 49 | IE.ELL..DE | DQKVRPNEEN | NKDADLYTSR | VMLSQVPLE | PPLFLFEEY KNYLDAANMS MRVRR..... 110 |
| NT3 | 8 | 70 | MDTELLRQQR | R......... | .......YNSPR | VILSDSTPLE | PPPYTMEDY VGSPVVANRT SRRKR..... 120 |
| NT4/5 | 9 | 11 | LAPEWD.... | .......... | .......LLSPR | VLLSRGAPAG | PPLFLFLEAG AFRESAGAPA NRGRR..... 56 |

Mature Regions

| | | | | | | | |
|---|---|---|---|---|---|---|---|
| NGF | 6 | RSKR.. | SSSHPIFHRGEFSVCDSVSV | WVGDKTTATDIKGKEV | .LGEV.NINNSVFKQYFFETKCR......... |
| BDGF | 7 | RVRR... | HSDPARRGELSVCDSISE | WVTAADKKTAVDMSGTVTVLEKVPLSKGQLKQYFYETKCN........ |
| NT3 | 8 | RRKR.. | YAEHKSHRGEYSVCDSES | LWVTDKSSAIDIRGHQVTVLGEI.KTGNSPVKQYFYETRCK....... |
| NT4/5 | 9 | RSRRGVSETAPASRRGELAVCDAVSG | WVTDRTAVDLRGREVEV | LGEVPAAGGSPLRQYFFETRCKADNAEEG |
| NGF | 6 | DPNPVDS | GCRGIDSKHWNSY | CTTTHTFVKALTMD.GKQAAWRFIRIDTAGVGVTVLEKVPLSKGQLKCR.. |
| BDGF | 7 | PMGYTKE | GCRGIDKRHWNSQ | CRTTQSYVRALTMDSKKRIGWRFIRIDTSGVSVCTLTIKRGR.. |
| NT3 | 8 | EARPVKNGGCRGIDDKHWNSQ | CKTSQTYVRALTSENNKLVG | WRWIRIDTSGVAPSRKIGRT. |
| NT4/5 | 9 | GPGAGGGGCRGVDRRHWVSE | CKAKQSYVRALTADAQGRVG | WRWIRIDTACVCTLLSRTGRA. |

Fig. 12
+pro-dom-BDNF
+HRP-S-protein
A                                1min exposure
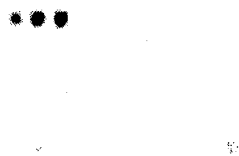
B                                5min exposure
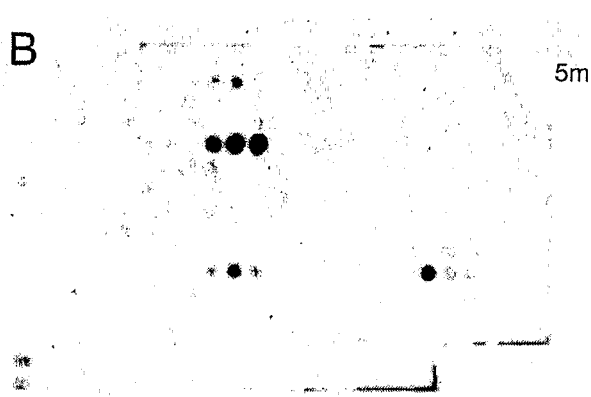

Fig. 13

|     |                  | SEQ ID NO: | Residues: |
|-----|------------------|------------|-----------|
| 64. | GGSRGGRIFRSSDFAK | 1 | 114-129 |
| 65. | RGGRIFRSSDFAKNFV | 1 | 117-132 |
| 66. | RIFRSSDFAKNFVQTD | 1 | 120-135 |
| 67. | RSSDFAKNFVQTDLPF | 1 | 123-138 |
| 68. | DFAKNFVQTDLPFHPL | 1 | 126-141 |
| 69. | KNFVQTDLPFHPLTQM | 1 | 129-144 |

Fig. 14

```
SEQ ID
NO:1
Residue
 57-91  ..PL..TTG Q..........  ..........  ..........  ..SK..S.Y .KN.K.H.D INTTIR....  ..........
 92-150 THEGMAAGPE NSER..TAE VSGGSRG...  ..........  .GR..PS.F ARM.VQT.D PHHPTQMY SPQN......
151-225 SD.LLA.SE N.E..SKN FGGKWEEIHK AVCLAKWGSD NTLL..YAN ESCKA...D GALELWRTSD LGKSEKTIGV
226-271 KI.SFG.G.. ..ER..A.V MADKDTT...  ..........  .RR.HVST.Q .DL.SM.A.Q PSVGQ.....  ..........
272-324 EQ.YSH.AAN ..ED..MMV DEPCDTGF..  ..........  .GT.TED.R .IV.SK...S DRHL.YTTSG  ..........
325-398 ETIFIN.TSL .Re.....TSV LSE.DNS...  ..........  .IQT.IH.Q .GR.THRKP ENSECDATAK NRNECSLHIH ASYSISQKLNV
399-445 PMAPLSEPNA V.E..AHG SVG.DAISVM .V........  .PD.ISD.G .EYS.TK.M .G........
446-489 PH.VTT.DSG ..E..A.I EHSSRPI...  ..........  .NV.KEST.E .QQ.QTY.T TRD.......
490-503 PI.FTG.ASE PGAR
                              *  *         *  *     *  *     *
```

Legend:
Identical at min 6 of 9 - white on black
Similar at min 6 of 8 white on grey
Similar at min 4 of 8 - black on grey
Rest - black SEQ ID NO: 1
(Residues 7-14)

SEQ ID NO: 1
(Residues 14-22)

SEQ ID NO: 1
(Residues 14-27)

Fig. 17

| Dots | BLU-His | BLU-Sprotein | SEQ ID NO: 1 Residues | Sequences | Dots | BLU-His | BLU-Sprotein | SEQ ID NO: 1 Residues | Sequences |
|---|---|---|---|---|---|---|---|---|---|
| 1 | 57033 | 136873 | 7-22 | RIFRSSDFAKNFVQTD | 46 | 20203 | 21459 | 7-13 | RIFRSSD |
| 2 | 112561 | 205984 | 7-21 | RIFRSSDFAKNFVQT | 47 | 24353 | 27779 | 8-14 | IFRSSDF |
| 3 | 23821 | 76169 | 8-22 | IFRSSDFAKNFVQTD | 48 | 16645 | 17213 | 9-15 | RSSDFA |
| 4 | 141157 | 172483 | 7-20 | RIFRSSDFAKNFVQ | 49 | 17289 | 16419 | 10-16 | RSSDFAK |
| 5 | 53378 | 190127 | 8-21 | IFRSSDFAKNFVQT | 50 | 16658 | 15919 | 11-17 | SSDFAKN |
| 6 | 18834 | 38091 | 9-22 | FRSSDFAKNFVQTD | 51 | 17173 | 17207 | 12-18 | SDFAKNF |
| 7 | 101606 | 168124 | 7-19 | RIFRSSDFAKNFV | 52 | 17262 | 17406 | 13-19 | DFAKNFV |
| 8 | 41614 | 126272 | 8-20 | IFRSSDFAKNFVQ | 53 | 69598 | 20345 | 14-20 | FAKNFVQ |
| 9 | 19707 | 222616 | 9-21 | FRSSDFAKNFVQT | 54 | 17266 | 16673 | 15-21 | AKNFVQT |
| 10 | 19772 | 20741 | 10-22 | RSSDFAKNFVQTD | 55 | 18257 | 17837 | 16-22 | KNFVQTD |
| 11 | 100124 | 165681 | 7-18 | RIFRSSDFAKNF | 56 | 121674 | 94377 | 7-12 | RIFRSS |
| 12 | 45066 | 198884 | 8-19 | IFRSSDFAKNFV | 57 | 17878 | 18126 | 8-13 | IFRSSD |
| 13 | 25753 | 198846 | 9-20 | FRSSDFAKNFVQ | 58 | 17525 | 16887 | 9-14 | FRSSDF |
| 14 | 24711 | 24619 | 10-21 | RSSDFAKNFVQT | 59 | 18259 | 15871 | 10-15 | RSSDFA |
| 15 | 19170 | 22393 | 11-22 | SSDFAKNFVQTD | 60 | 16095 | 15909 | 11-16 | SSDFAK |
| 16 | 32995 | 63638 | 7-17 | RIFRSSDFAKN | 61 | 15086 | 15553 | 12-17 | SDFAKN |
| 17 | 40690 | 126753 | 8-18 | IFRSSDFAKNF | 62 | 15201 | 15198 | 13-18 | DFAKNF |
| 18 | 19439 | 447934 | 9-19 | FRSSDFAKNFV | 63 | 141914 | 29586 | 14-19 | FAKNFV |
| 19 | 25985 | 22395 | 10-20 | RSSDFAKNFVQ | 64 | 15606 | 14136 | 15-20 | AKNFVQ |
| 20 | 16700 | 18447 | 11-21 | SSDFAKNFVQT | 65 | 15371 | 14323 | 16-21 | KNFVQT |
| 21 | 15709 | 16864 | 12-22 | SDFAKNFVQTD | 66 | 15350 | 14523 | 17-22 | NFVQTD |
| 22 | 45457 | 60543 | 7-16 | RIFRSSDFAK | 67 | 115400 | 137336 | 7-11 | RIFRS |
| 23 | 19745 | 29780 | 8-17 | IFRSSDFAKN | 68 | 25341 | 38497 | 8-12 | IFRSS |
| 24 | 20102 | 70449 | 9-18 | FRSSDFAKNF | 69 | 15834 | 14955 | 9-13 | FRSSD |
| 25 | 22980 | 25435 | 10-19 | RSSDFAKNFV | 70 | 16070 | 15484 | 10-14 | RSSDF |
| 26 | 17754 | 18541 | 11-20 | SSDFAKNFVQ | 71 | 15782 | 14686 | 11-15 | SSDFA |
| 27 | 17465 | 19075 | 12-21 | SDFAKNFVQT | 72 | 15032 | 14764 | 12-16 | SDFAK |
| 28 | 17435 | 19018 | 13-22 | DFAKNFVQTD | 73 | 17815 | 15617 | 13-17 | DFAKN |
| 29 | 43394 | 60918 | 7-15 | RIFRSSDFA | 74 | 31948 | 17524 | 14-18 | FAKNF |
| 30 | 20765 | 25725 | 8-16 | IFRSSDFAK | 75 | 17531 | 15909 | 15-19 | AKNFV |
| 31 | 20401 | 20344 | 9-17 | FRSSDFAKN | 76 | 18188 | 15706 | 16-20 | KNFVQ |
| 32 | 21053 | 19504 | 10-18 | RSSDFAKNF | 77 | 17263 | 16569 | 17-21 | NFVQT |
| 33 | 18907 | 19030 | 11-19 | SSDFAKNFV | 78 | 22397 | 15081 | 18-22 | FVQTD |
| 34 | 18437 | 18871 | 12-20 | SDFAKNFVQ | 79 | 127485 | 166402 | 7-10 | RIFR |
| 35 | 19065 | 19535 | 13-21 | DFAKNFVQT | 80 | 51082 | 110577 | 8-11 | IFRS |
| 36 | 30763 | 18814 | 14-22 | FAKNFVQTD | 81 | 20096 | 36968 | 9-12 | FRSS |
| 37 | 115934 | 113637 | 7-14 | RIFRSSDF | 82 | 15042 | 14900 | 10-13 | RSSD |
| 38 | 21437 | 24448 | 8-15 | IFRSSDFA | 83 | 14115 | 13955 | 11-14 | SSDF |
| 39 | 19039 | 19242 | 9-16 | FRSSDFAK | 84 | 14230 | 13295 | 12-15 | SDFA |
| 40 | 18657 | 17161 | 10-17 | RSSDFAKN | 85 | 14364 | 13313 | 13-16 | DFAK |
| 41 | 15462 | 16281 | 11-18 | SSDFAKNF | 86 | 15232 | 13746 | 14-17 | FAKN |
| 42 | 16309 | 15533 | 12-19 | SDFAKNFV | 87 | 14585 | 13670 | 15-18 | AKNF |
| 43 | 15508 | 14653 | 13-20 | DFAKNFVQ | 88 | 14866 | 13825 | 16-19 | KNFV |
| 44 | 60377 | 23561 | 14-21 | FAKNFVQT | 89 | 14735 | 13447 | 17-20 | NFVQ |
| 45 | 15952 | 15291 | 15-22 | AKNFVQTD | 90 | 15556 | 13599 | 18-21 | FVQT |
|  |  |  |  |  | 91 | 15081 | 13820 | 19-22 | VQTD |

Fig. 18
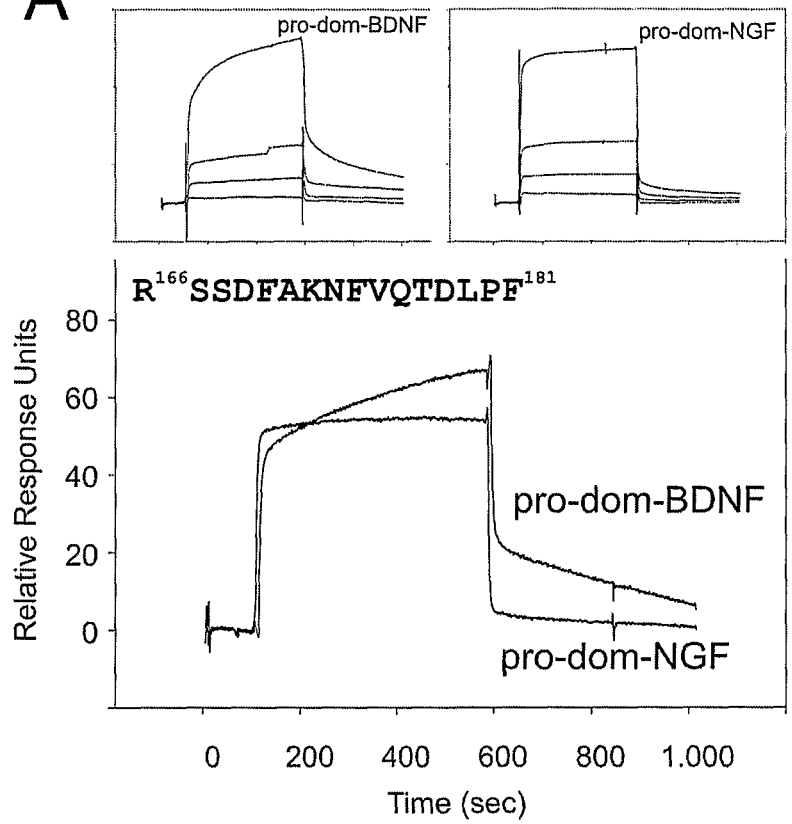
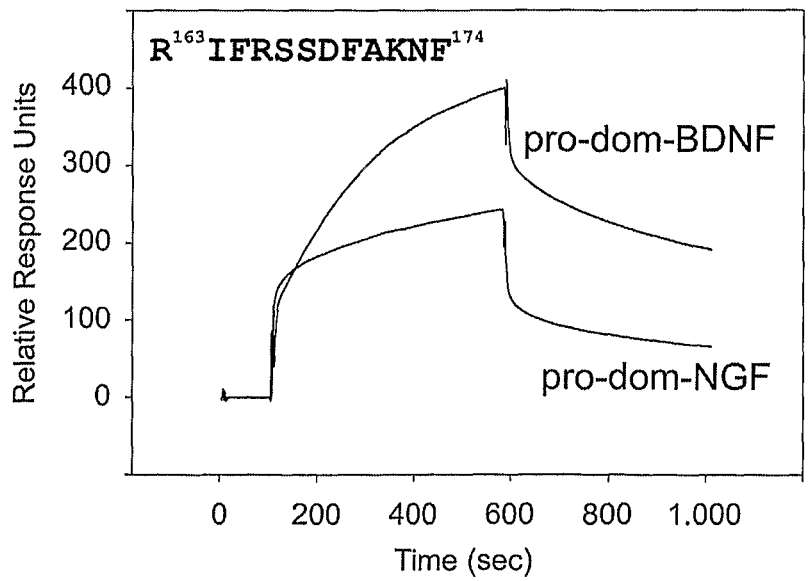

```
                        SEQUENCE LISTING

<160> NUMBER OF SEQ ID NOS: 57

<210> SEQ ID NO 1
<211> LENGTH: 798
<212> TYPE: PRT
<213> ORGANISM: Homo Sapiens
<220> FEATURE:
<221> NAME/KEY: MISC_FEATURE
<222> LOCATION: (1)..(798)
<223> OTHER INFORMATION: pro-Sortilin
<220> FEATURE:
<221> NAME/KEY: PROPEP
<222> LOCATION: (1)..(43)
<223> OTHER INFORMATION: Sortilin
<220> FEATURE:
<221> NAME/KEY: MISC_FEATURE
<222> LOCATION: (35)..(712)
<223> OTHER INFORMATION: Extracellular part of Sortilin
<220> FEATURE:
<221> NAME/KEY: mat_peptide
<222> LOCATION: (44)..(798)
<223> OTHER INFORMATION: Sortilin
<220> FEATURE:
<221> NAME/KEY: TRANSMEM
<222> LOCATION: (713)..(735)
<223> OTHER INFORMATION: Sortilin
<220> FEATURE:
<221> NAME/KEY: MISC_FEATURE
<222> LOCATION: (736)..(788)
<223> OTHER INFORMATION: Intracellular part of Sortilin

<400> SEQUENCE: 1

Gln Asp Arg Leu Asp Ala Pro Pro Pro Pro Ala Ala Pro Leu Pro Arg
        -40                 -35                 -30
```

```
Trp Ser Gly Pro Ile Gly Val Ser Trp Gly Leu Arg Ala Ala Ala
        -25                 -20                 -15
Gly Gly Ala Phe Pro Arg Gly Arg Trp Arg Arg Ser Ala Pro Gly
        -10                  -5              -1   1               5
Glu Asp Glu Glu Cys Gly Arg Val Arg Asp Phe Val Ala Lys Leu Ala
                     10                  15                  20
Asn Asn Thr His Gln His Val Phe Asp Asp Leu Arg Gly Ser Val Ser
                 25                  30                  35
Leu Ser Trp Val Gly Asp Ser Thr Gly Val Ile Leu Val Leu Thr Thr
             40                  45                  50
Phe His Val Pro Leu Val Ile Met Thr Phe Gly Gln Ser Lys Leu Tyr
             55                  60                  65
Arg Ser Glu Asp Tyr Gly Lys Asn Phe Lys Asp Ile Thr Asp Leu Ile
70                  75                  80                  85
Asn Asn Thr Phe Ile Arg Thr Glu Phe Gly Met Ala Ile Gly Pro Glu
                 90                  95                 100
Asn Ser Gly Lys Val Val Leu Thr Ala Glu Val Ser Gly Gly Ser Arg
            105                 110                 115
Gly Gly Arg Ile Phe Arg Ser Ser Asp Phe Ala Lys Asn Phe Val Gln
            120                 125                 130
Thr Asp Leu Pro Phe His Pro Leu Thr Gln Met Met Tyr Ser Pro Gln
135                 140                 145
Asn Ser Asp Tyr Leu Leu Ala Leu Ser Thr Glu Asn Gly Leu Trp Val
150                 155                 160                 165
Ser Lys Asn Phe Gly Gly Lys Trp Glu Glu Ile His Lys Ala Val Cys
                170                 175                 180
Leu Ala Lys Trp Gly Ser Asp Asn Thr Ile Phe Phe Thr Thr Tyr Ala
                185                 190                 195
Asn Gly Ser Cys Lys Ala Asp Leu Gly Ala Leu Glu Leu Trp Arg Thr
                200                 205                 210
Ser Asp Leu Gly Lys Ser Phe Lys Thr Ile Gly Val Lys Ile Tyr Ser
            215                 220                 225
Phe Gly Leu Gly Gly Arg Phe Leu Phe Ala Ser Val Met Ala Asp Lys
230                 235                 240                 245
Asp Thr Thr Arg Arg Ile His Val Ser Thr Asp Gln Gly Asp Thr Trp
                250                 255                 260
Ser Met Ala Gln Leu Pro Ser Val Gly Gln Glu Gln Phe Tyr Ser Ile
                265                 270                 275
Leu Ala Ala Asn Asp Asp Met Val Phe Met His Val Asp Glu Pro Gly
                280                 285                 290
Asp Thr Gly Phe Gly Thr Ile Phe Thr Ser Asp Asp Arg Gly Ile Val
            295                 300                 305
Tyr Ser Lys Ser Leu Asp Arg His Leu Tyr Thr Thr Thr Gly Gly Glu
310                 315                 320                 325
Thr Asp Phe Thr Asn Val Thr Ser Leu Arg Gly Val Tyr Ile Thr Ser
                330                 335                 340
Val Leu Ser Glu Asp Asn Ser Ile Gln Thr Met Ile Thr Phe Asp Gln
            345                 350                 355
Gly Gly Arg Trp Thr His Leu Arg Lys Pro Glu Asn Ser Glu Cys Asp
            360                 365                 370
Ala Thr Ala Lys Asn Lys Asn Glu Cys Ser Leu His Ile His Ala Ser
375                 380                 385
Tyr Ser Ile Ser Gln Lys Leu Asn Val Pro Met Ala Pro Leu Ser Glu
390                 395                 400                 405
```

```
Pro Asn Ala Val Gly Ile Val Ala His Gly Ser Val Gly Asp Ala
                410                 415                 420
Ile Ser Val Met Val Pro Asp Val Tyr Ile Ser Asp Asp Gly Gly Tyr
                425                 430                 435
Ser Trp Thr Lys Met Leu Glu Gly Pro His Tyr Tyr Thr Ile Leu Asp
                440                 445                 450
Ser Gly Gly Ile Ile Val Ala Ile Glu His Ser Ser Arg Pro Ile Asn
                455                 460                 465
Val Ile Lys Phe Ser Thr Asp Glu Gly Gln Cys Trp Gln Thr Tyr Thr
470                 475                 480                 485
Phe Thr Arg Asp Pro Ile Tyr Phe Thr Gly Leu Ala Ser Glu Pro Gly
                490                 495                 500
Ala Arg Ser Met Asn Ile Ser Ile Trp Gly Phe Thr Glu Ser Phe Leu
                505                 510                 515
Thr Ser Gln Trp Val Ser Tyr Thr Ile Asp Phe Lys Asp Ile Leu Glu
                520                 525                 530
Arg Asn Cys Glu Glu Lys Asp Tyr Thr Ile Trp Leu Ala His Ser Thr
                535                 540                 545
Asp Pro Glu Asp Tyr Glu Asp Gly Cys Ile Leu Gly Tyr Lys Glu Gln
550                 555                 560                 565
Phe Leu Arg Leu Arg Lys Ser Ser Met Cys Gln Asn Gly Arg Asp Tyr
                570                 575                 580
Val Val Thr Lys Gln Pro Ser Ile Cys Leu Cys Ser Leu Glu Asp Phe
                585                 590                 595
Leu Cys Asp Phe Gly Tyr Tyr Arg Pro Glu Asn Asp Ser Lys Cys Val
                600                 605                 610
Glu Gln Pro Glu Leu Lys Gly His Asp Leu Glu Phe Cys Leu Tyr Gly
                615                 620                 625
Arg Glu Glu His Leu Thr Thr Asn Gly Tyr Arg Lys Ile Pro Gly Asp
630                 635                 640                 645
Lys Cys Gln Gly Gly Val Asn Pro Val Arg Glu Val Lys Asp Leu Lys
                650                 655                 660
Lys Lys Cys Thr Ser Asn Phe Leu Ser Pro Glu Lys Gln Asn Ser Lys
                665                 670                 675
Ser Asn Ser Val Pro Ile Ile Leu Ala Ile Val Gly Leu Met Leu Val
                680                 685                 690
Thr Val Val Ala Gly Val Leu Ile Val Lys Lys Tyr Val Cys Gly Gly
                695                 700                 705
Arg Phe Leu Val His Arg Tyr Ser Val Leu Gln Gln His Ala Glu Ala
710                 715                 720                 725
Asn Gly Val Asp Gly Val Asp Ala Leu Asp Thr Ala Ser His Thr Asn
                730                 735                 740
Lys Ser Gly Tyr His Asp Asp Ser Asp Glu Asp Leu Leu Glu
                745                 750                 755

<210> SEQ ID NO 2
<211> LENGTH: 2214
<212> TYPE: PRT
<213> ORGANISM: Homo Sapiens
<220> FEATURE:
<221> NAME/KEY: SIGNAL
<222> LOCATION: (1)..(28)
<223> OTHER INFORMATION: SorLA
<220> FEATURE:
<221> NAME/KEY: PROPEP
<222> LOCATION: (29)..(81)
<223> OTHER INFORMATION: SorLA
```

-continued

```
<220> FEATURE:
<221> NAME/KEY: MISC_FEATURE
<222> LOCATION: (29)..(2214)
<223> OTHER INFORMATION: pro-SorLA
<220> FEATURE:
<221> NAME/KEY: mat_peptide
<222> LOCATION: (82)..(2214)
<223> OTHER INFORMATION: SorLA
<220> FEATURE:
<221> NAME/KEY: MISC_FEATURE
<222> LOCATION: (82)..(2137)
<223> OTHER INFORMATION: Extracellular part of SorLA
<220> FEATURE:
<221> NAME/KEY: TRANSMEM
<222> LOCATION: (2138)..(2158)
<223> OTHER INFORMATION: SorLA
<220> FEATURE:
<221> NAME/KEY: MISC_FEATURE
<222> LOCATION: (2159)..(2214)
<223> OTHER INFORMATION: Intracellular part of SorLA

<400> SEQUENCE: 2

Met Ala Thr Arg Ser Ser Arg Arg Glu Ser Arg Leu Pro Phe Leu Phe
    -80                 -75                 -70

Thr Leu Val Ala Leu Leu Pro Pro Gly Ala Leu Cys Glu Val Trp Thr
-65                 -60                 -55                 -50

Gln Arg Leu His Gly Gly Ser Ala Pro Leu Pro Gln Asp Arg Gly Phe
                -45                 -40                 -35

Leu Val Val Gln Gly Asp Pro Arg Glu Leu Arg Leu Trp Ala Arg Gly
            -30                 -25                 -20

Asp Ala Arg Gly Ala Ser Arg Ala Asp Glu Lys Pro Leu Arg Arg Lys
        -15                 -10                  -5

Arg Ser Ala Ala Leu Gln Pro Glu Pro Ile Lys Val Tyr Gly Gln Val
 -1   1                  5                  10                 15

Ser Leu Asn Asp Ser His Asn Gln Met Val Val His Trp Ala Gly Glu
                20                  25                  30

Lys Ser Asn Val Ile Val Ala Leu Ala Arg Asp Ser Leu Ala Leu Ala
                35                  40                  45

Arg Pro Lys Ser Ser Asp Val Tyr Val Ser Tyr Asp Tyr Gly Lys Ser
            50                  55                  60

Phe Lys Lys Ile Ser Asp Lys Leu Asn Phe Gly Leu Gly Asn Arg Ser
        65                  70                  75

Glu Ala Val Ile Ala Gln Phe Tyr His Ser Pro Ala Asp Asn Lys Arg
 80                  85                  90                  95

Tyr Ile Phe Ala Asp Ala Tyr Ala Gln Tyr Leu Trp Ile Thr Phe Asp
                100                 105                 110

Phe Cys Asn Thr Leu Gln Gly Phe Ser Ile Pro Phe Arg Ala Ala Asp
                115                 120                 125

Leu Leu Leu His Ser Lys Ala Ser Asn Leu Leu Gly Phe Asp Arg
                130                 135                 140

Ser His Pro Asn Lys Gln Leu Trp Lys Ser Asp Phe Gly Gln Thr
            145                 150                 155

Trp Ile Met Ile Gln Glu His Val Lys Ser Phe Ser Trp Gly Ile Asp
160                 165                 170                 175

Pro Tyr Asp Lys Pro Asn Thr Ile Tyr Ile Glu Arg His Glu Pro Ser
                180                 185                 190

Gly Tyr Ser Thr Val Phe Arg Ser Thr Asp Phe Phe Gln Ser Arg Glu
            195                 200                 205

Asn Gln Glu Val Ile Leu Glu Glu Val Arg Asp Phe Gln Leu Arg Asp
            210                 215                 220
```

-continued

```
Lys Tyr Met Phe Ala Thr Lys Val His Leu Leu Gly Ser Glu Gln
225                 230                 235
Gln Ser Ser Val Gln Leu Trp Val Ser Phe Gly Arg Lys Pro Met Arg
240                 245                 250                 255
Ala Ala Gln Phe Val Thr Arg His Pro Ile Asn Glu Tyr Tyr Ile Ala
                    260                 265                 270
Asp Ala Ser Glu Asp Gln Val Phe Val Cys Val Ser His Ser Asn Asn
                275                 280                 285
Arg Thr Asn Leu Tyr Ile Ser Glu Ala Glu Gly Leu Lys Phe Ser Leu
            290                 295                 300
Ser Leu Glu Asn Val Leu Tyr Tyr Ser Pro Gly Ala Gly Ser Asp
305                 310                 315
Thr Leu Val Arg Tyr Phe Ala Asn Glu Pro Phe Ala Asp Phe His Arg
320                 325                 330                 335
Val Glu Gly Leu Gln Gly Val Tyr Ile Ala Thr Leu Ile Asn Gly Ser
                    340                 345                 350
Met Asn Glu Glu Asn Met Arg Ser Val Ile Thr Phe Asp Lys Gly Gly
                355                 360                 365
Thr Trp Glu Phe Leu Gln Ala Pro Ala Phe Thr Gly Tyr Gly Glu Lys
            370                 375                 380
Ile Asn Cys Glu Leu Ser Gln Gly Cys Ser Leu His Leu Ala Gln Arg
385                 390                 395
Leu Ser Gln Leu Leu Asn Leu Gln Leu Arg Arg Met Pro Ile Leu Ser
400                 405                 410                 415
Lys Glu Ser Ala Pro Gly Leu Ile Ile Ala Thr Gly Ser Val Gly Lys
                    420                 425                 430
Asn Leu Ala Ser Lys Thr Asn Val Tyr Ile Ser Ser Ala Gly Ala
                435                 440                 445
Arg Trp Arg Glu Ala Leu Pro Gly Pro His Tyr Tyr Thr Trp Gly Asp
            450                 455                 460
His Gly Gly Ile Ile Thr Ala Ile Ala Gln Gly Met Glu Thr Asn Glu
465                 470                 475
Leu Lys Tyr Ser Thr Asn Glu Gly Glu Thr Trp Lys Thr Phe Ile Phe
480                 485                 490                 495
Ser Glu Lys Pro Val Phe Val Tyr Gly Leu Leu Thr Glu Pro Gly Glu
                    500                 505                 510
Lys Ser Thr Val Phe Thr Ile Phe Gly Ser Asn Lys Glu Asn Val His
                515                 520                 525
Ser Trp Leu Ile Leu Gln Val Asn Ala Thr Asp Ala Leu Gly Val Pro
            530                 535                 540
Cys Thr Glu Asn Asp Tyr Lys Leu Trp Ser Pro Ser Asp Glu Arg Gly
545                 550                 555
Asn Glu Cys Leu Leu Gly His Lys Thr Val Phe Lys Arg Arg Thr Pro
560                 565                 570                 575
His Ala Thr Cys Phe Asn Gly Glu Asp Phe Asp Arg Pro Val Val Val
                    580                 585                 590
Ser Asn Cys Ser Cys Thr Arg Glu Asp Tyr Glu Cys Asp Phe Gly Phe
                595                 600                 605
Lys Met Ser Glu Asp Leu Ser Leu Glu Val Cys Val Pro Asp Pro Glu
            610                 615                 620
Phe Ser Gly Lys Ser Tyr Ser Pro Val Pro Cys Pro Val Gly Ser
625                 630                 635
Thr Tyr Arg Arg Thr Arg Gly Tyr Arg Lys Ile Ser Gly Asp Thr Cys
640                 645                 650                 655
```

-continued

```
Ser Gly Gly Asp Val Glu Ala Arg Leu Glu Gly Glu Leu Val Pro Cys
            660                 665                 670

Pro Leu Ala Glu Glu Asn Glu Phe Ile Leu Tyr Ala Val Arg Lys Ser
            675                 680                 685

Ile Tyr Arg Tyr Asp Leu Ala Ser Gly Ala Thr Glu Gln Leu Pro Leu
            690                 695                 700

Thr Gly Leu Arg Ala Ala Val Ala Leu Asp Phe Asp Tyr Glu His Asn
            705                 710                 715

Cys Leu Tyr Trp Ser Asp Leu Ala Leu Asp Val Ile Gln Arg Leu Cys
720                 725                 730                 735

Leu Asn Gly Ser Thr Gly Gln Glu Val Ile Ile Asn Ser Gly Leu Glu
            740                 745                 750

Thr Val Glu Ala Leu Ala Phe Glu Pro Leu Ser Gln Leu Leu Tyr Trp
            755                 760                 765

Val Asp Ala Gly Phe Lys Lys Ile Glu Val Ala Asn Pro Asp Gly Asp
            770                 775                 780

Phe Arg Leu Thr Ile Val Asn Ser Ser Val Leu Asp Arg Pro Arg Ala
            785                 790                 795

Leu Val Leu Val Pro Gln Glu Gly Val Met Phe Trp Thr Asp Trp Gly
800                 805                 810                 815

Asp Leu Lys Pro Gly Ile Tyr Arg Ser Asn Met Asp Gly Ser Ala Ala
            820                 825                 830

Tyr His Leu Val Ser Glu Asp Val Lys Trp Pro Asn Gly Ile Ser Val
            835                 840                 845

Asp Asp Gln Trp Ile Tyr Trp Thr Asp Ala Tyr Leu Glu Cys Ile Glu
            850                 855                 860

Arg Ile Thr Phe Ser Gly Gln Gln Arg Ser Val Ile Leu Asp Asn Leu
865                 870                 875

Pro His Pro Tyr Ala Ile Ala Val Phe Lys Asn Glu Ile Tyr Trp Asp
880                 885                 890                 895

Asp Trp Ser Gln Leu Ser Ile Phe Arg Ala Ser Lys Tyr Ser Gly Ser
            900                 905                 910

Gln Met Glu Ile Leu Ala Asn Gln Leu Thr Gly Leu Met Asp Met Lys
            915                 920                 925

Ile Phe Tyr Lys Gly Lys Asn Thr Gly Ser Asn Ala Cys Val Pro Arg
            930                 935                 940

Pro Cys Ser Leu Leu Cys Leu Pro Lys Ala Asn Asn Ser Arg Ser Cys
945                 950                 955

Arg Cys Pro Glu Asp Val Ser Ser Ser Val Leu Pro Ser Gly Asp Leu
960                 965                 970                 975

Met Cys Asp Cys Pro Gln Gly Tyr Gln Leu Lys Asn Asn Thr Cys Val
            980                 985                 990

Lys Glu Glu Asn Thr Cys Leu Arg Asn Gln Tyr Arg Cys Ser Asn Gly
            995                 1000                1005

Asn Cys Ile Asn Ser Ile Trp Trp Cys Asp Phe Asp Asn Asp Cys
            1010                1015                1020

Gly Asp Met Ser Asp Glu Arg Asn Cys Pro Thr Thr Ile Cys Asp
            1025                1030                1035

Leu Asp Thr Gln Phe Arg Cys Gln Glu Ser Gly Thr Cys Ile Pro
            1040                1045                1050

Leu Ser Tyr Lys Cys Asp Leu Glu Asp Asp Cys Gly Asp Asn Ser
            1055                1060                1065
```

```
Asp Glu Ser His Cys Glu Met His Gln Cys Arg Ser Asp Glu Tyr
         1070                1075                1080

Asn Cys Ser Ser Gly Met Cys Ile Arg Ser Ser Trp Val Cys Asp
         1085                1090                1095

Gly Asp Asn Asp Cys Arg Asp Trp Ser Asp Glu Ala Asn Cys Thr
         1100                1105                1110

Ala Ile Tyr His Thr Cys Glu Ala Ser Asn Phe Gln Cys Arg Asn
         1115                1120                1125

Gly His Cys Ile Pro Gln Arg Trp Ala Cys Asp Gly Asp Thr Asp
         1130                1135                1140

Cys Gln Asp Gly Ser Asp Glu Asp Pro Val Asn Cys Glu Lys Lys
         1145                1150                1155

Cys Asn Gly Phe Arg Cys Pro Asn Gly Thr Cys Ile Pro Ser Ser
         1160                1165                1170

Lys His Cys Asp Gly Leu Arg Asp Cys Ser Asp Gly Ser Asp Glu
         1175                1180                1185

Gln His Cys Glu Pro Leu Cys Thr His Phe Met Asp Phe Val Cys
         1190                1195                1200

Lys Asn Arg Gln Gln Cys Leu Phe His Ser Met Val Cys Asp Gly
         1205                1210                1215

Ile Ile Gln Cys Arg Asp Gly Ser Asp Glu Asp Ala Ala Phe Ala
         1220                1225                1230

Gly Cys Ser Gln Asp Pro Glu Phe His Lys Val Cys Asp Glu Phe
         1235                1240                1245

Gly Phe Gln Cys Gln Asn Gly Val Cys Ile Ser Leu Ile Trp Lys
         1250                1255                1260

Cys Asp Gly Met Asp Asp Cys Gly Asp Tyr Ser Asp Glu Ala Asn
         1265                1270                1275

Cys Glu Asn Pro Thr Glu Ala Pro Asn Cys Ser Arg Tyr Phe Gln
         1280                1285                1290

Phe Arg Cys Glu Asn Gly His Cys Ile Pro Asn Arg Trp Lys Cys
         1295                1300                1305

Asp Arg Glu Asn Asp Cys Gly Asp Trp Ser Asp Glu Lys Asp Cys
         1310                1315                1320

Gly Asp Ser His Ile Leu Pro Phe Ser Thr Pro Gly Pro Ser Thr
         1325                1330                1335

Cys Leu Pro Asn Tyr Tyr Arg Cys Ser Ser Gly Thr Cys Val Met
         1340                1345                1350

Asp Thr Trp Val Cys Asp Gly Tyr Arg Asp Cys Ala Asp Gly Ser
         1355                1360                1365

Asp Glu Glu Ala Cys Pro Leu Leu Ala Asn Val Thr Ala Ala Ser
         1370                1375                1380

Thr Pro Thr Gln Leu Gly Arg Cys Asp Arg Phe Glu Phe Glu Cys
         1385                1390                1395

His Gln Pro Lys Thr Cys Ile Pro Asn Trp Lys Arg Cys Asp Gly
         1400                1405                1410

His Gln Asp Cys Gln Asp Gly Arg Asp Glu Ala Asn Cys Pro Thr
         1415                1420                1425

His Ser Thr Leu Thr Cys Met Ser Arg Glu Phe Gln Cys Glu Asp
         1430                1435                1440

Gly Glu Ala Cys Ile Val Leu Ser Glu Arg Cys Asp Gly Phe Leu
         1445                1450                1455

Asp Cys Ser Asp Glu Ser Asp Glu Lys Ala Cys Ser Asp Glu Leu
         1460                1465                1470
```

-continued

```
Thr Val Tyr Lys Val Gln Asn Leu Gln Trp Thr Ala Asp Phe Ser
    1475            1480                1485

Gly Asp Val Thr Leu Thr Trp Met Arg Pro Lys Lys Met Pro Ser
    1490            1495                1500

Ala Ser Cys Val Tyr Asn Val Tyr Tyr Arg Val Val Gly Glu Ser
    1505            1510                1515

Ile Trp Lys Thr Leu Glu Thr His Ser Asn Lys Thr Asn Thr Val
    1520            1525                1530

Leu Lys Val Leu Lys Pro Asp Thr Thr Tyr Gln Val Lys Val Gln
    1535            1540                1545

Val Gln Cys Leu Ser Lys Ala His Asn Thr Asn Asp Phe Val Thr
    1550            1555                1560

Leu Arg Thr Pro Glu Gly Leu Pro Asp Ala Pro Arg Asn Leu Gln
    1565            1570                1575

Leu Ser Leu Pro Arg Glu Ala Glu Gly Val Ile Val Gly His Trp
    1580            1585                1590

Ala Pro Pro Ile His Thr His Gly Leu Ile Arg Glu Tyr Ile Val
    1595            1600                1605

Glu Tyr Ser Arg Ser Gly Ser Lys Met Trp Ala Ser Gln Arg Ala
    1610            1615                1620

Ala Ser Asn Phe Thr Glu Ile Lys Asn Leu Leu Val Asn Thr Leu
    1625            1630                1635

Tyr Thr Val Arg Val Ala Ala Val Thr Ser Arg Gly Ile Gly Asn
    1640            1645                1650

Trp Ser Asp Ser Lys Ser Ile Thr Thr Ile Lys Gly Lys Val Ile
    1655            1660                1665

Pro Pro Pro Asp Ile His Ile Asp Ser Tyr Gly Glu Asn Tyr Leu
    1670            1675                1680

Ser Phe Thr Leu Thr Met Glu Ser Asp Ile Lys Val Asn Gly Tyr
    1685            1690                1695

Val Val Asn Leu Phe Trp Ala Phe Asp Thr His Lys Gln Glu Arg
    1700            1705                1710

Arg Thr Leu Asn Phe Arg Gly Ser Ile Leu Ser His Lys Val Gly
    1715            1720                1725

Asn Leu Thr Ala His Thr Ser Tyr Glu Ile Ser Ala Trp Ala Lys
    1730            1735                1740

Thr Asp Leu Gly Asp Ser Pro Leu Ala Phe Glu His Val Met Thr
    1745            1750                1755

Arg Gly Val Arg Pro Pro Ala Pro Ser Leu Lys Ala Lys Ala Ile
    1760            1765                1770

Asn Gln Thr Ala Val Glu Cys Thr Trp Thr Gly Pro Arg Asn Val
    1775            1780                1785

Val Tyr Gly Ile Phe Tyr Ala Thr Ser Phe Leu Asp Leu Tyr Arg
    1790            1795                1800

Asn Pro Lys Ser Leu Thr Thr Ser Leu His Asn Lys Thr Val Ile
    1805            1810                1815

Val Ser Lys Asp Glu Gln Tyr Leu Phe Leu Val Arg Val Val Val
    1820            1825                1830

Pro Tyr Gln Gly Pro Ser Ser Asp Tyr Val Val Lys Met Ile
    1835            1840                1845

Pro Asp Ser Arg Leu Pro Pro Arg His Leu His Val Val His Thr
    1850            1855                1860
```

-continued

Gly Lys Thr Ser Val Val Ile Lys Trp Glu Ser Pro Tyr Asp Ser
    1865                1870                1875

Pro Asp Gln Asp Leu Leu Tyr Ala Ile Ala Val Lys Asp Leu Ile
    1880                1885                1890

Arg Lys Thr Asp Arg Ser Tyr Lys Val Lys Ser Arg Asn Ser Thr
    1895                1900                1905

Val Glu Tyr Thr Leu Asn Lys Leu Glu Pro Gly Gly Lys Tyr His
    1910                1915                1920

Ile Ile Val Gln Leu Gly Asn Met Ser Lys Asp Ser Ser Ile Lys
    1925                1930                1935

Ile Thr Thr Val Ser Leu Ser Ala Pro Asp Ala Leu Lys Ile Ile
    1940                1945                1950

Thr Glu Asn Asp His Val Leu Leu Phe Trp Lys Ser Leu Ala Leu
    1955                1960                1965

Lys Glu Lys His Phe Asn Glu Ser Arg Gly Tyr Glu Ile His Met
    1970                1975                1980

Phe Asp Ser Ala Met Asn Ile Thr Ala Tyr Leu Gly Asn Thr Thr
    1985                1990                1995

Asp Asn Phe Phe Lys Ile Ser Asn Leu Lys Met Gly His Asn Tyr
    2000                2005                2010

Thr Phe Thr Val Gln Ala Arg Cys Leu Phe Gly Asn Gln Ile Cys
    2015                2020                2025

Gly Glu Pro Ala Ile Leu Leu Tyr Asp Glu Leu Gly Ser Gly Ala
    2030                2035                2040

Asp Ala Ser Ala Thr Gln Ala Ala Arg Ser Thr Asp Val Ala Ala
    2045                2050                2055

Val Val Val Pro Ile Leu Phe Leu Ile Leu Leu Ser Leu Gly Val
    2060                2065                2070

Gly Phe Ala Ile Leu Tyr Thr Lys His Arg Arg Leu Gln Ser Ser
    2075                2080                2085

Phe Thr Ala Phe Ala Asn Ser His Tyr Ser Ser Arg Leu Gly Ser
    2090                2095                2100

Ala Ile Phe Ser Ser Gly Asp Asp Leu Gly Glu Asp Asp Glu Asp
    2105                2110                2115

Ala Pro Met Ile Thr Gly Phe Ser Asp Asp Val Pro Met Val Ile
    2120                2125                2130

Ala

<210> SEQ ID NO 3
<211> LENGTH: 1168
<212> TYPE: PRT
<213> ORGANISM: Homo Sapiens

<400> SEQUENCE: 3

Met Gly Lys Val Gly Ala Gly Gly Ser Gln Ala Arg Leu Ser Ala
1               5                   10                  15

Leu Leu Ala Gly Ala Gly Leu Leu Ile Leu Cys Ala Pro Gly Val Cys
            20                  25                  30

Gly Gly Gly Ser Cys Cys Pro Ser Pro His Pro Ser Ser Ala Pro Arg
            35                  40                  45

Ser Ala Ser Thr Pro Arg Gly Phe Ser His Gln Gly Arg Pro Gly Arg
            50                  55                  60

Ala Pro Ala Thr Pro Leu Pro Leu Val Val Arg Pro Leu Phe Ser Val
65                  70                  75                  80

```
Ala Pro Gly Asp Arg Ala Leu Ser Leu Glu Arg Ala Arg Gly Thr Gly
             85                  90                  95
Ala Ser Met Ala Val Ala Ala Arg Ser Gly Arg Arg Arg Ser Gly
            100                 105                 110
Ala Asp Gln Glu Lys Ala Glu Arg Gly Glu Gly Ala Ser Arg Ser Pro
            115                 120                 125
Arg Gly Val Leu Arg Asp Gly Gln Gln Glu Pro Gly Thr Arg Glu
            130                 135                 140
Arg Asp Pro Asp Lys Ala Thr Arg Phe Arg Met Glu Glu Leu Arg Leu
145                 150                 155                 160
Thr Ser Thr Thr Phe Ala Leu Thr Gly Asp Ser Ala His Asn Gln Ala
                165                 170                 175
Met Val His Trp Ser Gly His Asn Ser Ser Val Ile Leu Ile Leu Thr
                180                 185                 190
Lys Leu Tyr Asp Tyr Asn Leu Gly Ser Ile Thr Glu Ser Ser Leu Trp
                195                 200                 205
Arg Ser Thr Asp Tyr Gly Thr Thr Tyr Glu Lys Leu Asn Asp Lys Val
            210                 215                 220
Gly Leu Lys Thr Ile Leu Gly Tyr Leu Val Cys Pro Thr Asn Lys
225                 230                 235                 240
Arg Lys Ile Met Leu Leu Thr Asp Pro Glu Ile Glu Ser Ser Leu Leu
                245                 250                 255
Ile Ser Ser Asp Glu Gly Ala Thr Tyr Gln Lys Tyr Arg Leu Asn Phe
                260                 265                 270
Tyr Ile Gln Ser Leu Leu Phe His Pro Lys Glu Asp Trp Ile Leu
                275                 280                 285
Ala Tyr Ser Gln Asp Gln Lys Leu Tyr Ser Ser Ala Glu Phe Gly Arg
            290                 295                 300
Arg Trp Gln Leu Ile Gln Glu Gly Val Val Pro Asn Arg Phe Tyr Trp
305                 310                 315                 320
Ser Val Met Gly Ser Asn Lys Glu Pro Asp Leu Val His Leu Glu Ala
                325                 330                 335
Arg Thr Val Asp Gly His Ser His Tyr Leu Thr Cys Arg Met Gln Asn
                340                 345                 350
Cys Thr Glu Ala Asn Arg Asn Gln Pro Phe Pro Gly Tyr Ile Asp Pro
                355                 360                 365
Asp Ser Leu Ile Val Gln Asp His Tyr Val Phe Val Gln Leu Thr Ser
            370                 375                 380
Gly Gly Arg Pro His Tyr Tyr Val Ser Tyr Arg Arg Asn Ala Phe Ala
385                 390                 395                 400
Gln Met Lys Leu Pro Lys Tyr Ala Leu Pro Lys Asp Met His Val Ile
                405                 410                 415
Ser Thr Asp Glu Asn Gln Val Phe Ala Ala Val Gln Glu Trp Asn Gln
            420                 425                 430
Asn Asp Thr Tyr Asn Leu Tyr Ile Ser Asp Thr Arg Gly Val Tyr Phe
            435                 440                 445
Thr Leu Ala Leu Glu Asn Val Gln Ser Ser Arg Gly Pro Glu Gly Asn
            450                 455                 460
Ile Met Ile Asp Leu Tyr Glu Val Ala Gly Ile Lys Gly Met Phe Leu
465                 470                 475                 480
Ala Asn Lys Lys Ile Asp Tyr Gln Val Lys Thr Phe Ile Thr Tyr Asn
                485                 490                 495
Lys Gly Arg Asp Trp Arg Leu Leu Gln Ala Pro Asp Thr Asp Leu Arg
            500                 505                 510
```

```
Gly Asp Pro Val His Cys Leu Leu Pro Tyr Cys Ser Leu His Leu His
            515                 520                 525

Leu Lys Val Ser Glu Asn Pro Tyr Thr Ser Gly Ile Ile Ala Ser Lys
        530                 535                 540

Asp Thr Ala Pro Ser Ile Ile Val Ala Ser Gly Asn Ile Gly Ser Glu
545                 550                 555                 560

Leu Ser Asp Thr Asp Ile Ser Met Phe Val Ser Ser Asp Ala Gly Asn
                565                 570                 575

Thr Trp Arg Gln Ile Phe Glu Glu His Ser Val Leu Tyr Leu Asp
            580                 585                 590

Gln Gly Gly Val Leu Val Ala Met Lys His Thr Ser Leu Pro Ile Arg
        595                 600                 605

His Leu Trp Leu Ser Phe Asp Glu Gly Arg Ser Trp Ser Lys Tyr Ser
    610                 615                 620

Phe Thr Ser Ile Pro Leu Phe Val Asp Gly Val Leu Gly Glu Pro Gly
625                 630                 635                 640

Glu Glu Thr Leu Ile Met Thr Val Phe Gly His Phe Ser His Arg Ser
                645                 650                 655

Glu Trp Gln Leu Val Lys Val Asp Tyr Lys Ser Ile Phe Asp Arg Arg
            660                 665                 670

Cys Ala Glu Glu Asp Tyr Arg Pro Trp Gln Leu His Ser Gln Gly Glu
        675                 680                 685

Ala Cys Ile Met Gly Ala Lys Arg Ile Tyr Lys Lys Arg Lys Ser Glu
        690                 695                 700

Arg Lys Cys Met Gln Gly Lys Tyr Ala Gly Ala Met Glu Ser Glu Pro
705                 710                 715                 720

Cys Val Cys Thr Glu Ala Asp Phe Asp Cys Asp Tyr Gly Tyr Glu Arg
                725                 730                 735

His Ser Asn Gly Gln Cys Leu Pro Ala Phe Trp Phe Asn Pro Ser Ser
            740                 745                 750

Leu Ser Lys Asp Cys Ser Leu Gly Gln Ser Tyr Leu Asn Ser Thr Gly
        755                 760                 765

Tyr Arg Lys Val Val Ser Asn Asn Cys Thr Asp Gly Val Arg Glu Gln
        770                 775                 780

Tyr Thr Ala Lys Pro Gln Lys Cys Pro Gly Lys Ala Pro Arg Gly Leu
785                 790                 795                 800

Arg Ile Val Thr Ala Asp Gly Lys Leu Thr Ala Glu Gln Gly His Asn
                805                 810                 815

Val Thr Leu Met Val Gln Leu Glu Glu Gly Asp Val Gln Arg Thr Leu
            820                 825                 830

Ile Gln Val Asp Phe Gly Asp Gly Ile Ala Val Ser Tyr Val Asn Leu
        835                 840                 845

Ser Ser Met Glu Asp Gly Ile Lys His Val Tyr Gln Asn Val Gly Ile
        850                 855                 860

Phe Arg Val Thr Val Gln Val Asp Asn Ser Leu Gly Ser Asp Ser Ala
865                 870                 875                 880

Val Leu Tyr Leu His Val Thr Cys Pro Leu Glu His Val His Leu Ser
                885                 890                 895

Leu Pro Phe Val Thr Thr Lys Asn Lys Glu Val Asn Ala Thr Ala Val
            900                 905                 910

Leu Trp Pro Ser Gln Val Gly Thr Leu Thr Tyr Val Trp Trp Tyr Gly
        915                 920                 925
```

```
Asn Asn Thr Glu Pro Leu Ile Thr Leu Glu Gly Ser Ile Ser Phe Arg
        930                 935                 940

Phe Thr Ser Glu Gly Met Asn Thr Ile Thr Val Gln Val Ser Ala Gly
945                 950                 955                 960

Asn Ala Ile Leu Gln Asp Thr Lys Thr Ile Ala Val Tyr Glu Phe
                965                 970                 975

Arg Ser Leu Arg Leu Ser Phe Ser Pro Asn Leu Asp Asp Tyr Asn Pro
        980                 985                 990

Asp Ile Pro Glu Trp Arg Arg Asp Ile Gly Arg Val Ile Lys Lys Ser
        995                 1000                1005

Leu Val Glu Ala Thr Gly Val Pro Gly Gln His Ile Leu Val Ala
    1010                1015                1020

Val Leu Pro Gly Leu Pro Thr Thr Ala Glu Leu Phe Val Leu Pro
    1025                1030                1035

Tyr Gln Asp Pro Ala Gly Glu Asn Lys Arg Ser Thr Asp Asp Leu
    1040                1045                1050

Glu Gln Ile Ser Glu Leu Leu Ile His Thr Leu Asn Gln Asn Ser
    1055                1060                1065

Val His Phe Glu Leu Lys Pro Gly Val Arg Val Leu Val His Ala
    1070                1075                1080

Ala His Leu Thr Ala Ala Pro Leu Val Asp Leu Thr Pro Thr His
    1085                1090                1095

Ser Gly Ser Ala Met Leu Met Leu Leu Ser Val Val Phe Val Gly
    1100                1105                1110

Leu Ala Val Phe Val Ile Tyr Lys Phe Lys Arg Arg Val Ala Leu
    1115                1120                1125

Pro Ser Pro Pro Ser Pro Ser Thr Gln Pro Gly Asp Ser Ser Leu
    1130                1135                1140

Arg Leu Gln Arg Ala Arg His Ala Thr Pro Ser Thr Pro Lys
    1145                1150                1155

Arg Gly Ser Ala Gly Ala Gln Tyr Ala Ile
    1160                1165

<210> SEQ ID NO 4
<211> LENGTH: 907
<212> TYPE: PRT
<213> ORGANISM: Homo Sapiens

<400> SEQUENCE: 4

Leu Ile Phe His Pro Lys Glu Asp Lys Val Leu Ala Tyr Thr Lys
1               5                   10                  15

Glu Ser Lys Leu Tyr Val Ser Ser Asp Leu Gly Lys Lys Trp Thr Leu
            20                  25                  30

Leu Gln Glu Arg Val Thr Lys Asp His Val Phe Trp Ser Val Ser Gly
        35                  40                  45

Val Asp Ala Asp Pro Asp Leu Val His Val Glu Ala Gln Asp Leu Gly
    50                  55                  60

Gly Asp Phe Arg Tyr Val Thr Cys Ala Ile His Asn Cys Ser Glu Lys
65                  70                  75                  80

Met Leu Thr Ala Pro Phe Ala Gly Pro Ile Asp His Gly Ser Leu Thr
                85                  90                  95

Val Gln Asp Asp Tyr Ile Phe Phe Lys Ala Thr Ser Ala Asn Gln Thr
            100                 105                 110

Lys Tyr Tyr Val Ser Tyr Arg Arg Asn Glu Phe Val Leu Met Lys Leu
        115                 120                 125
```

-continued

```
Pro Lys Tyr Ala Leu Pro Lys Asp Leu Gln Ile Ile Ser Thr Asp Glu
    130                 135                 140
Ser Gln Val Phe Val Ala Val Gln Glu Trp Tyr Gln Met Asp Thr Tyr
145                 150                 155                 160
Asn Leu Tyr Gln Ser Asp Pro Arg Gly Val Arg Tyr Ala Leu Val Leu
                165                 170                 175
Gln Asp Val Arg Ser Arg Gln Ala Glu Glu Ser Val Leu Ile Asp
            180                 185                 190
Ile Leu Glu Val Arg Gly Val Lys Gly Val Phe Leu Ala Asn Gln Lys
        195                 200                 205
Ile Asp Gly Lys Val Met Thr Leu Ile Thr Tyr Asn Lys Gly Arg Asp
210                 215                 220
Trp Asp Tyr Leu Arg Pro Pro Ser Met Asp Met Asn Gly Lys Pro Thr
225                 230                 235                 240
Asn Cys Lys Pro Pro Asp Cys His Leu His Leu His Leu Arg Trp Ala
                245                 250                 255
Asp Asn Pro Tyr Val Ser Gly Thr Val His Thr Lys Asp Thr Ala Pro
            260                 265                 270
Gly Leu Ile Met Gly Ala Gly Asn Leu Gly Ser Gln Leu Val Glu Tyr
        275                 280                 285
Lys Glu Glu Met Tyr Ile Thr Ser Asp Cys Gly His Thr Trp Arg Gln
290                 295                 300
Val Phe Glu Glu Glu His His Ile Leu Tyr Leu Asp His Gly Gly Val
305                 310                 315                 320
Ile Val Ala Ile Lys Asp Thr Ser Ile Pro Leu Lys Ile Leu Lys Phe
                325                 330                 335
Ser Val Asp Glu Gly Leu Thr Trp Ser Thr His Asn Phe Thr Ser Thr
            340                 345                 350
Ser Val Phe Val Asp Gly Leu Leu Ser Glu Pro Gly Asp Glu Thr Leu
        355                 360                 365
Val Met Thr Val Phe Gly His Ile Ser Phe Arg Ser Asp Trp Glu Leu
370                 375                 380
Val Lys Val Asp Phe Arg Pro Ser Phe Ser Arg Gln Cys Gly Glu Glu
385                 390                 395                 400
Asp Tyr Ser Ser Trp Glu Leu Ser Asn Leu Gln Gly Asp Arg Cys Ile
                405                 410                 415
Met Gly Gln Gln Arg Ser Phe Arg Lys Arg Lys Ser Thr Ser Trp Cys
            420                 425                 430
Ile Lys Gly Arg Ser Phe Thr Ser Ala Leu Thr Ser Arg Val Cys Glu
        435                 440                 445
Cys Arg Asp Ser Asp Phe Leu Cys Asp Tyr Gly Phe Glu Arg Ser Pro
450                 455                 460
Ser Ser Glu Ser Ser Thr Asn Lys Cys Ser Ala Asn Phe Trp Phe Asn
465                 470                 475                 480
Pro Leu Ser Pro Pro Asp Asp Cys Ala Leu Gly Gln Thr Tyr Thr Ser
                485                 490                 495
Ser Leu Gly Tyr Arg Lys Val Val Ser Asn Val Cys Glu Gly Gly Val
            500                 505                 510
Asp Met Gln Gln Ser Gln Val Gln Leu Gln Cys Pro Leu Thr Pro Pro
        515                 520                 525
Arg Gly Leu Gln Val Ser Ile Gln Gly Glu Ala Val Ala Val Arg Pro
530                 535                 540
Gly Glu Asp Val Leu Phe Val Val Arg Gln Glu Gln Gly Asp Val Leu
545                 550                 555                 560
```

```
Thr Thr Lys Tyr Gln Val Asp Leu Gly Asp Gly Phe Lys Ala Met Tyr
            565                 570                 575

Val Asn Leu Thr Leu Thr Gly Glu Pro Ile Arg His Arg Tyr Glu Ser
            580                 585                 590

Pro Gly Ile Tyr Arg Val Ser Val Arg Ala Glu Asn Thr Ala Gly His
            595                 600                 605

Asp Glu Ala Val Leu Phe Val Gln Val Asn Ser Pro Leu Gln Ala Leu
610                 615                 620

Tyr Leu Glu Val Val Pro Val Ile Gly Leu Asn Gln Glu Val Asn Leu
625                 630                 635                 640

Thr Ala Val Leu Leu Pro Leu Asn Pro Asn Leu Thr Val Phe Tyr Trp
            645                 650                 655

Trp Ile Gly His Ser Leu Gln Pro Leu Leu Ser Leu Asp Asn Ser Val
            660                 665                 670

Thr Thr Arg Phe Ser Asp Thr Gly Asp Val Arg Val Thr Val Gln Ala
            675                 680                 685

Ala Cys Gly Asn Ser Val Leu Gln Asp Ser Arg Val Leu Arg Val Leu
690                 695                 700

Asp Gln Phe Gln Val Met Pro Leu Gln Phe Ser Lys Glu Leu Asp Ala
705                 710                 715                 720

Tyr Asn Pro Asn Thr Pro Glu Trp Arg Glu Asp Val Gly Leu Val Val
            725                 730                 735

Thr Arg Leu Leu Ser Lys Glu Thr Ser Val Pro Gln Glu Leu Leu Val
            740                 745                 750

Thr Val Val Lys Pro Gly Leu Pro Thr Leu Ala Asp Leu Tyr Val Leu
            755                 760                 765

Leu Pro Pro Pro Arg Pro Thr Arg Lys Arg Ser Leu Ser Ser Asp Lys
770                 775                 780

Arg Leu Ala Ala Ile Gln Gln Val Leu Asn Ala Gln Lys Ile Ser Phe
785                 790                 795                 800

Leu Leu Arg Gly Gly Val Arg Val Leu Ala Leu Arg Asp Thr Gly
            805                 810                 815

Thr Gly Ala Glu Gln Leu Gly Gly Gly Gly Tyr Trp Ala Val Val
            820                 825                 830

Val Leu Phe Val Ile Gly Leu Phe Ala Ala Gly Ala Phe Ile Leu Tyr
            835                 840                 845

Lys Phe Lys Arg Lys Arg Pro Gly Arg Thr Val Tyr Ala Gln Met His
850                 855                 860

Asn Glu Lys Glu Gln Glu Met Thr Ser Pro Val Ser His Ser Glu Asp
865                 870                 875                 880

Val Gln Gly Ala Val Gln Gly Asn His Ser Gly Val Val Leu Ser Ile
            885                 890                 895

Asn Ser Arg Glu Met His Ser Tyr Leu Val Ser
            900                 905

<210> SEQ ID NO 5
<211> LENGTH: 1222
<212> TYPE: PRT
<213> ORGANISM: Homo Sapiens

<400> SEQUENCE: 5

Met Glu Ala Ala Arg Thr Glu Arg Pro Ala Gly Arg Pro Gly Ala Pro
1               5                   10                  15

Leu Val Arg Thr Gly Leu Leu Leu Leu Ser Thr Trp Val Leu Ala Gly
            20                  25                  30
```

```
Ala Glu Ile Thr Trp Asp Ala Thr Gly Gly Pro Gly Arg Pro Ala Ala
         35                  40                  45

Pro Ala Ser Arg Pro Pro Ala Leu Ser Pro Leu Ser Pro Arg Ala Val
     50                  55                  60

Ala Ser Gln Trp Pro Glu Glu Leu Ala Ser Arg Arg Ala Ala Val
 65                  70                  75                  80

Leu Gly Arg Arg Ala Gly Pro Glu Leu Leu Pro Gln Gln Gly Gly Gly
                 85                  90                  95

Arg Gly Gly Glu Met Gln Val Glu Ala Gly Gly Thr Ser Pro Ala Gly
             100                 105                 110

Glu Arg Arg Gly Arg Gly Ile Pro Ala Pro Ala Lys Leu Gly Gly Ala
         115                 120                 125

Arg Arg Ser Arg Arg Ala Gln Pro Pro Ile Thr Gln Glu Arg Gly Asp
         130                 135                 140

Ala Trp Ala Thr Ala Pro Ala Asp Gly Ser Arg Gly Ser Arg Pro Leu
145                 150                 155                 160

Ala Lys Gly Ser Arg Glu Val Lys Ala Pro Arg Ala Gly Gly Ser
                 165                 170                 175

Ala Ala Glu Asp Leu Arg Leu Pro Ser Thr Ser Phe Ala Leu Thr Gly
             180                 185                 190

Asp Ser Ala His Asn Gln Ala Met Val His Trp Ser Gly His Asn Ser
         195                 200                 205

Ser Val Ile Leu Ile Leu Thr Lys Leu Tyr Asp Phe Asn Leu Gly Ser
     210                 215                 220

Val Thr Glu Ser Ser Leu Trp Arg Ser Thr Asp Tyr Gly Thr Thr Tyr
225                 230                 235                 240

Glu Lys Leu Asn Asp Lys Val Gly Leu Lys Thr Val Leu Ser Tyr Leu
                 245                 250                 255

Tyr Val Asn Pro Thr Asn Lys Arg Lys Ile Met Leu Leu Ser Asp Pro
             260                 265                 270

Glu Met Glu Ser Ser Ile Leu Ile Ser Ser Asp Glu Gly Ala Thr Tyr
         275                 280                 285

Gln Lys Tyr Arg Leu Thr Phe Tyr Ile Gln Ser Leu Leu Phe His Pro
         290                 295                 300

Lys Gln Glu Asp Trp Val Leu Ala Tyr Ser Leu Asp Gln Lys Leu Tyr
305                 310                 315                 320

Ser Ser Met Asp Phe Gly Arg Arg Trp Gln Leu Met His Glu Arg Ile
                 325                 330                 335

Thr Pro Asn Arg Phe Tyr Trp Ser Val Ala Gly Leu Asp Lys Glu Ala
             340                 345                 350

Asp Leu Val His Met Glu Val Arg Thr Thr Asp Gly Tyr Ala His Tyr
         355                 360                 365

Leu Thr Cys Arg Ile Gln Glu Cys Ala Glu Thr Thr Arg Ser Gly Pro
     370                 375                 380

Phe Ala Arg Ser Ile Asp Ile Ser Ser Leu Val Val Gln Asp Glu Tyr
385                 390                 395                 400

Ile Phe Ile Gln Val Thr Thr Ser Gly Arg Ala Ser Tyr Tyr Val Ser
                 405                 410                 415

Tyr Arg Arg Glu Ala Phe Ala Gln Ile Lys Leu Pro Lys Tyr Ser Leu
             420                 425                 430

Pro Lys Asp Met His Ile Ile Ser Thr Asp Glu Asn Gln Val Phe Ala
         435                 440                 445
```

```
Ala Val Gln Glu Trp Asn Gln Asn Asp Thr Tyr Asn Leu Tyr Ile Ser
    450                 455                 460

Asp Thr Arg Gly Ile Tyr Phe Thr Leu Ala Met Glu Asn Ile Lys Ser
465                 470                 475                 480

Ser Arg Gly Leu Met Gly Asn Ile Ile Glu Leu Tyr Glu Val Ala
                485                 490                 495

Gly Ile Lys Gly Ile Phe Leu Ala Asn Lys Lys Val Asp Asp Gln Val
                500                 505                 510

Lys Thr Tyr Ile Thr Tyr Asn Lys Gly Arg Asp Trp Arg Leu Leu Gln
        515                 520                 525

Ala Pro Asp Val Asp Leu Arg Gly Ser Pro Val His Cys Leu Leu Pro
    530                 535                 540

Phe Cys Ser Leu His Leu His Leu Gln Leu Ser Glu Asn Pro Tyr Ser
545                 550                 555                 560

Ser Gly Arg Ile Ser Ser Lys Glu Thr Ala Pro Gly Leu Val Val Ala
                565                 570                 575

Thr Gly Asn Ile Gly Pro Glu Leu Ser Tyr Thr Asp Ile Gly Val Phe
                580                 585                 590

Ile Ser Ser Asp Gly Gly Asn Thr Trp Arg Gln Ile Phe Asp Glu Glu
        595                 600                 605

Tyr Asn Val Trp Phe Leu Asp Trp Gly Gly Ala Leu Val Ala Met Lys
    610                 615                 620

His Thr Pro Leu Pro Val Arg His Leu Trp Val Ser Phe Asp Glu Gly
625                 630                 635                 640

His Ser Trp Asp Lys Tyr Gly Phe Thr Ser Val Pro Leu Phe Val Asp
                645                 650                 655

Gly Ala Leu Val Glu Ala Gly Met Glu Thr His Ile Met Thr Val Phe
                660                 665                 670

Gly His Phe Ser Leu Arg Ser Glu Trp Gln Leu Val Lys Val Asp Tyr
        675                 680                 685

Lys Ser Ile Phe Ser Arg His Cys Thr Lys Glu Asp Tyr Gln Thr Trp
    690                 695                 700

His Leu Leu Asn Gln Gly Glu Pro Cys Val Met Gly Glu Arg Lys Ile
705                 710                 715                 720

Phe Lys Lys Arg Lys Pro Gly Ala Gln Cys Ala Leu Gly Arg Asp His
                725                 730                 735

Ser Gly Ser Val Val Ser Glu Pro Cys Val Cys Ala Asn Trp Asp Phe
                740                 745                 750

Glu Cys Asp Tyr Gly Tyr Glu Arg His Gly Glu Ser Gln Cys Val Pro
        755                 760                 765

Ala Phe Trp Tyr Asn Pro Ala Ser Pro Ser Lys Asp Cys Ser Leu Gly
    770                 775                 780

Gln Ser Tyr Leu Asn Ser Thr Gly Tyr Arg Arg Ile Val Ser Asn Asn
785                 790                 795                 800

Cys Thr Asp Gly Leu Arg Glu Lys Tyr Thr Ala Lys Ala Gln Met Cys
                805                 810                 815

Pro Gly Lys Ala Pro Arg Gly Leu His Val Val Thr Thr Asp Gly Arg
                820                 825                 830

Leu Val Ala Glu Gln Gly His Asn Ala Thr Phe Ile Ile Leu Met Glu
        835                 840                 845

Glu Gly Asp Leu Gln Arg Thr Asn Ile Gln Leu Asp Phe Gly Asp Gly
    850                 855                 860

Ile Ala Val Ser Tyr Ala Asn Phe Ser Pro Ile Glu Asp Gly Ile Lys
865                 870                 875                 880
```

```
His Val Tyr Lys Ser Ala Gly Ile Phe Gln Val Thr Ala Tyr Ala Glu
            885                 890                 895

Asn Asn Leu Gly Ser Asp Thr Ala Val Leu Phe Leu His Val Val Cys
            900                 905                 910

Pro Val Glu His Val His Leu Arg Val Pro Phe Val Ala Ile Arg Asn
            915                 920                 925

Lys Glu Val Asn Ile Ser Ala Val Val Trp Pro Ser Gln Leu Gly Thr
930                 935                 940

Leu Thr Tyr Phe Trp Trp Phe Gly Asn Ser Thr Lys Pro Leu Ile Thr
945                 950                 955                 960

Leu Asp Ser Ser Ile Ser Phe Thr Phe Leu Ala Gly Thr Asp Thr
            965                 970                 975

Ile Thr Val Gln Val Ala Ala Gly Asn Ala Leu Ile Gln Asp Thr Lys
            980                 985                 990

Glu Ile Ala Val His Glu Tyr Phe  Gln Ser Gln Leu Leu  Ser Phe Ser
            995                 1000                1005

Pro Asn  Leu Asp Tyr His Asn  Pro Asp Ile Pro Glu  Trp Arg Lys
    1010                1015                1020

Asp Ile  Gly Asn Val Ile Lys  Arg Ala Leu Val Lys  Val Thr Ser
    1025                1030                1035

Val Pro  Glu Asp Gln Ile Leu  Ile Ala Val Phe Pro  Gly Leu Pro
    1040                1045                1050

Thr Ser  Ala Glu Leu Phe Ile  Leu Pro Pro Lys Asn  Leu Thr Glu
    1055                1060                1065

Arg Arg  Lys Gly Asn Glu Gly  Asp Leu Glu Gln Ile  Val Glu Thr
    1070                1075                1080

Leu Phe  Asn Ala Leu Asn Gln  Asn Leu Val Gln Phe  Glu Leu Lys
    1085                1090                1095

Pro Gly  Val Gln Val Ile Val  Tyr Val Thr Gln Leu  Thr Leu Ala
    1100                1105                1110

Pro Leu  Val Asp Ser Ser Ala  Gly His Ser Ser Ser  Ala Met Leu
    1115                1120                1125

Met Leu  Leu Ser Val Val Phe  Val Gly Leu Ala Val  Phe Leu Ile
    1130                1135                1140

Tyr Lys  Phe Lys Arg Lys Ile  Pro Trp Ile Asn Ile  Tyr Ala Gln
    1145                1150                1155

Val Gln  His Asp Lys Glu Gln  Glu Met Ile Gly Ser  Val Ser Gln
    1160                1165                1170

Ser Glu  Asn Ala Pro Lys Ile  Thr Leu Ser Asp Phe  Thr Glu Pro
    1175                1180                1185

Glu Glu  Leu Leu Asp Lys Glu  Leu Asp Thr Arg Val  Ile Gly Gly
    1190                1195                1200

Ile Ala  Thr Ile Ala Asn Ser  Glu Ser Thr Lys Glu  Ile Pro Asn
    1205                1210                1215

Cys Thr  Ser Val
    1220

<210> SEQ ID NO 6
<211> LENGTH: 241
<212> TYPE: PRT
<213> ORGANISM: Homo Sapiens
<220> FEATURE:
<221> NAME/KEY: SIGNAL
<222> LOCATION: (1)..(18)
<223> OTHER INFORMATION: NGF
<220> FEATURE:
```

```
<221> NAME/KEY: PROPEP
<222> LOCATION: (19)..(121)
<223> OTHER INFORMATION: NGF
<220> FEATURE:
<221> NAME/KEY: mat_peptide
<222> LOCATION: (122)..(241)
<223> OTHER INFORMATION: NGF

<400> SEQUENCE: 6
```

Met Ser Met Leu Phe Tyr Thr Leu Ile Thr Ala Phe Leu Ile Gly
    -120                -115                -110

Ile Gln Ala Glu Pro His Ser Glu Ser Asn Val Pro Ala Gly His Thr
    -105                -100                -95

Ile Pro Gln Val His Trp Thr Lys Leu Gln His Ser Leu Asp Thr Ala
-90                 -85                 -80                 -75

Leu Arg Arg Ala Arg Ser Ala Pro Ala Ala Ile Ala Ala Arg Val
                -70                 -65                 -60

Ala Gly Gln Thr Arg Asn Ile Thr Val Asp Pro Arg Leu Phe Lys Lys
                -55                 -50                 -45

Arg Arg Leu Arg Ser Pro Arg Val Leu Phe Ser Thr Gln Pro Pro Arg
            -40                 -35                 -30

Glu Ala Ala Asp Thr Gln Asp Leu Asp Phe Glu Val Gly Gly Ala Ala
        -25                 -20                 -15

Pro Phe Asn Arg Thr His Arg Ser Lys Arg Ser Ser His Pro Ile
-10                 -5                  -1  1               5

Phe His Arg Gly Glu Phe Ser Val Cys Asp Ser Val Ser Val Trp Val
                10                  15                  20

Gly Asp Lys Thr Thr Ala Thr Asp Ile Lys Gly Lys Glu Val Met Val
        25                  30                  35

Leu Gly Glu Val Asn Ile Asn Asn Ser Val Phe Lys Gln Tyr Phe Phe
        40                  45                  50

Glu Thr Lys Cys Arg Asp Pro Asn Pro Val Asp Ser Gly Cys Arg Gly
55                  60                  65                  70

Ile Asp Ser Lys His Trp Asn Ser Tyr Cys Thr Thr Thr His Thr Phe
                75                  80                  85

Val Lys Ala Leu Thr Met Asp Gly Lys Gln Ala Ala Trp Arg Phe Ile
                90                  95                  100

Arg Ile Asp Thr Ala Cys Val Cys Val Leu Ser Arg Lys Ala Val Arg
            105                 110                 115

Arg Ala
    120

```
<210> SEQ ID NO 7
<211> LENGTH: 246
<212> TYPE: PRT
<213> ORGANISM: Homo Sapiens
<220> FEATURE:
<221> NAME/KEY: SIGNAL
<222> LOCATION: (1)..(18)
<223> OTHER INFORMATION: BDNF
<220> FEATURE:
<221> NAME/KEY: PROPEP
<222> LOCATION: (19)..(127)
<220> FEATURE:
<221> NAME/KEY: mat_peptide
<222> LOCATION: (128)..(246)
<223> OTHER INFORMATION: BDNF

<400> SEQUENCE: 7
```

Met Thr Ile Leu Phe Leu Thr Met Val Ile Ser Tyr Phe Gly Cys
    -125                -120                -115

```
Met Lys Ala Ala Pro Met Lys Glu Ala Asn Ile Arg Gly Gln Gly
    -110              -105                 -100

Gly Leu Ala Tyr Pro Gly Val Arg Thr His Gly Thr Leu Glu Ser Val
         -95              -90              -85

Asn Gly Pro Lys Ala Gly Ser Gly Leu Thr Ser Leu Ala Asp Thr Phe
    -80              -75                  -70

Glu His Val Ile Glu Glu Leu Leu Asp Glu Asp Gln Lys Val Arg Pro
-65              -60              -55              -50

Asn Glu Glu Asn Asn Lys Asp Ala Asp Leu Tyr Thr Ser Arg Val Met
             -45              -40              -35

Leu Ser Ser Gln Val Pro Leu Glu Pro Pro Leu Leu Phe Leu Leu Glu
            -30              -25              -20

Glu Tyr Lys Asn Tyr Leu Asp Ala Ala Asn Met Ser Met Arg Val Arg
        -15              -10               -5

Arg His Ser Asp Pro Ala Arg Arg Gly Glu Leu Ser Val Cys Asp Ser
 -1   1             5                 10                  15

Ile Ser Glu Trp Val Thr Ala Ala Asp Lys Lys Thr Ala Val Asp Met
                20              25              30

Ser Gly Gly Thr Val Thr Val Leu Glu Lys Val Pro Val Ser Lys Gly
            35              40              45

Gln Leu Lys Gln Tyr Phe Tyr Glu Thr Lys Cys Asn Pro Met Gly Tyr
        50              55              60

Thr Lys Glu Gly Cys Arg Gly Ile Asp Lys Arg His Trp Asn Ser Gln
    65              70              75

Cys Arg Thr Thr Gln Ser Tyr Val Arg Ala Leu Thr Met Asp Ser Lys
80              85              90              95

Lys Arg Ile Gly Trp Arg Phe Ile Arg Ile Asp Thr Ser Cys Val Cys
            100             105             110

Thr Leu Thr Ile Lys Arg Gly Arg
            115

<210> SEQ ID NO 8
<211> LENGTH: 257
<212> TYPE: PRT
<213> ORGANISM: Homo Sapiens
<220> FEATURE:
<221> NAME/KEY: SIGNAL
<222> LOCATION: (1)..(16)
<220> FEATURE:
<221> NAME/KEY: PROPEP
<222> LOCATION: (17)..(140)
<220> FEATURE:
<221> NAME/KEY: mat_peptide
<222> LOCATION: (141)..(257)
<223> OTHER INFORMATION: NT3

<400> SEQUENCE: 8

Met Ser Ile Leu Phe Tyr Val Ile Phe Leu Ala Tyr Leu Arg Gly
-140             -135             -130

Ile Gln Gly Asn Asn Met Asp Gln Arg Ser Leu Pro Glu Asp Ser
-125             -120             -115

Leu Asn Ser Leu Ile Ile Lys Leu Ile Gln Ala Asp Ile Leu Lys
-110             -105             -100

Asn Lys Leu Ser Lys Gln Met Val Asp Val Lys Glu Asn Tyr Gln Ser
-95              -90              -85              -80

Thr Leu Pro Lys Ala Glu Ala Pro Arg Glu Pro Glu Arg Gly Gly Pro
            -75              -70              -65

Ala Lys Ser Ala Phe Gln Pro Val Ile Ala Met Asp Thr Glu Leu Leu
            -60              -55              -50
```

```
Arg Gln Gln Arg Arg Tyr Asn Ser Pro Arg Val Leu Leu Ser Asp Ser
        -45                 -40                 -35

Thr Pro Leu Glu Pro Pro Leu Tyr Leu Met Glu Asp Tyr Val Gly
        -30                 -25                 -20

Ser Pro Val Val Ala Asn Arg Thr Ser Arg Arg Lys Arg Tyr Ala Glu
-15                 -10                  -5                  -1   1

His Lys Ser His Arg Gly Glu Tyr Ser Val Cys Asp Ser Glu Ser Leu
         5                  10                  15

Trp Val Thr Asp Lys Ser Ser Ala Ile Asp Ile Arg Gly His Gln Val
         20                  25                  30

Thr Val Leu Gly Glu Ile Lys Thr Gly Asn Ser Pro Val Lys Gln Tyr
         35                  40                  45

Phe Tyr Glu Thr Arg Cys Lys Glu Ala Arg Pro Val Lys Asn Gly Cys
 50                  55                  60                  65

Arg Gly Ile Asp Asp Lys His Trp Asn Ser Gln Cys Lys Thr Ser Gln
         70                  75                  80

Thr Tyr Val Arg Ala Leu Thr Ser Glu Asn Asn Lys Leu Val Gly Trp
         85                  90                  95

Arg Trp Ile Arg Ile Asp Thr Ser Cys Val Cys Ala Leu Ser Arg Lys
        100                 105                 110

Ile Gly Arg Thr
        115

<210> SEQ ID NO 9
<211> LENGTH: 210
<212> TYPE: PRT
<213> ORGANISM: Homo Sapiens
<220> FEATURE:
<221> NAME/KEY: SIGNAL
<222> LOCATION: (1)..(24)
<220> FEATURE:
<221> NAME/KEY: PROPEP
<222> LOCATION: (25)..(80)
<220> FEATURE:
<221> NAME/KEY: mat_peptide
<222> LOCATION: (81)..(210)

<400> SEQUENCE: 9

Met Leu Pro Leu Pro Ser Cys Ser Leu Pro Ile Leu Leu Phe Leu
-80                 -75                 -70                 -65

Leu Pro Ser Val Pro Ile Glu Ser Gln Pro Pro Ser Thr Leu Pro
        -60                 -55                 -50

Pro Phe Leu Ala Pro Glu Trp Asp Leu Ser Pro Arg Val Val Leu
        -45                 -40                 -35

Ser Arg Gly Ala Pro Ala Gly Pro Leu Leu Phe Leu Leu Glu Ala
        -30                 -25                 -20

Gly Ala Phe Arg Glu Ser Ala Gly Ala Pro Ala Asn Arg Ser Arg Arg
-15                 -10                  -5                  -1

Gly Val Ser Glu Thr Ala Pro Ala Ser Arg Arg Gly Glu Leu Ala Val
 1                   5                  10                  15

Cys Asp Ala Val Ser Gly Trp Val Thr Asp Arg Arg Thr Ala Val Asp
         20                  25                  30

Leu Arg Gly Arg Glu Val Glu Val Leu Gly Glu Val Pro Ala Ala Gly
         35                  40                  45

Gly Ser Pro Leu Arg Gln Tyr Phe Phe Glu Thr Arg Cys Lys Ala Asp
         50                  55                  60

Asn Ala Glu Glu Gly Gly Pro Gly Ala Gly Gly Gly Gly Cys Arg Gly
 65                  70                  75                  80
```

```
Val Asp Arg Arg His Trp Val Ser Glu Cys Lys Ala Lys Gln Ser Tyr
             85                  90                  95

Val Arg Ala Leu Thr Ala Asp Ala Gln Gly Arg Val Gly Trp Arg Trp
            100                 105                 110

Ile Arg Ile Asp Thr Ala Cys Val Cys Thr Leu Leu Ser Arg Thr Gly
        115                 120                 125

Arg Ala
    130

<210> SEQ ID NO 10
<211> LENGTH: 13
<212> TYPE: PRT
<213> ORGANISM: Homo Sapiens

<400> SEQUENCE: 10

Gln Leu Tyr Glu Asn Lys Pro Arg Arg Pro Tyr Ile Leu
1               5                   10

<210> SEQ ID NO 11
<211> LENGTH: 5
<212> TYPE: PRT
<213> ORGANISM: Homo Sapiens

<400> SEQUENCE: 11

Ile Pro Tyr Ile Leu
1               5

<210> SEQ ID NO 12
<211> LENGTH: 357
<212> TYPE: PRT
<213> ORGANISM: Homo Sapiens

<400> SEQUENCE: 12

Met Ala Pro Arg Arg Val Arg Ser Phe Leu Arg Gly Leu Pro Ala Leu
1               5                   10                  15

Leu Leu Leu Leu Leu Phe Leu Gly Pro Trp Pro Ala Ala Ser His Gly
            20                  25                  30

Gly Lys Tyr Ser Arg Glu Lys Asn Gln Pro Lys Pro Ser Pro Lys Arg
        35                  40                  45

Glu Ser Gly Glu Glu Phe Arg Met Glu Lys Leu Asn Gln Leu Trp Glu
    50                  55                  60

Lys Ala Gln Arg Leu His Leu Pro Pro Val Arg Leu Ala Glu Leu His
65                  70                  75                  80

Ala Asp Leu Lys Ile Gln Glu Arg Asp Glu Leu Ala Trp Lys Lys Leu
                85                  90                  95

Lys Leu Asp Gly Leu Asp Glu Asp Gly Glu Lys Glu Ala Arg Leu Ile
            100                 105                 110

Arg Asn Leu Asn Val Ile Leu Ala Lys Tyr Gly Leu Asp Gly Lys Lys
        115                 120                 125

Asp Ala Arg Gln Val Thr Ser Asn Ser Leu Ser Gly Thr Gln Glu Asp
    130                 135                 140

Gly Leu Asp Asp Pro Arg Leu Glu Lys Leu Trp His Lys Ala Lys Thr
145                 150                 155                 160

Ser Gly Lys Phe Ser Gly Glu Glu Leu Asp Lys Leu Trp Arg Glu Phe
                165                 170                 175

Leu His His Lys Glu Lys Val His Glu Tyr Asn Val Leu Leu Glu Thr
            180                 185                 190
```

```
Leu Ser Arg Thr Glu Glu Ile His Glu Asn Val Ile Ser Pro Ser Asp
            195                 200                 205

Leu Ser Asp Ile Lys Gly Ser Val Leu His Ser Arg His Thr Glu Leu
        210                 215                 220

Lys Glu Lys Leu Arg Ser Ile Asn Gln Gly Leu Asp Arg Leu Arg Arg
225                 230                 235                 240

Val Ser His Gln Gly Tyr Ser Thr Glu Ala Glu Phe Glu Pro Arg
                245                 250                 255

Val Ile Asp Leu Trp Asp Leu Ala Gln Ser Ala Asn Leu Thr Asp Lys
                260                 265                 270

Glu Leu Glu Ala Phe Arg Glu Glu Leu Lys His Phe Glu Ala Lys Ile
            275                 280                 285

Glu Lys His Asn His Tyr Gln Lys Gln Leu Glu Ile Ala His Glu Lys
        290                 295                 300

Leu Arg His Ala Glu Ser Val Gly Asp Gly Glu Arg Val Ser Arg Ser
305                 310                 315                 320

Arg Glu Lys His Ala Leu Leu Glu Gly Arg Thr Lys Glu Leu Gly Tyr
                325                 330                 335

Thr Val Lys Lys His Leu Gln Asp Leu Ser Gly Arg Ile Ser Arg Ala
                340                 345                 350

Arg His Asn Glu Leu
        355

<210> SEQ ID NO 13
<211> LENGTH: 170
<212> TYPE: PRT
<213> ORGANISM: Homo Sapiens

<400> SEQUENCE: 13

Met Met Ala Gly Met Lys Ile Gln Leu Val Cys Met Leu Leu Leu Ala
1               5                   10                  15

Phe Ser Ser Trp Ser Leu Cys Ser Asp Ser Glu Glu Met Lys Ala
                20                  25                  30

Leu Glu Ala Asp Phe Leu Thr Asn Met His Thr Ser Lys Ile Ser Lys
            35                  40                  45

Ala His Val Pro Ser Trp Lys Met Thr Leu Leu Asn Val Cys Ser Leu
        50                  55                  60

Val Asn Asn Leu Asn Ser Pro Ala Glu Glu Thr Gly Glu Val His Glu
65                  70                  75                  80

Glu Glu Leu Val Ala Arg Arg Lys Leu Pro Thr Ala Leu Asp Gly Phe
                85                  90                  95

Ser Leu Glu Ala Met Leu Thr Ile Tyr Gln Leu His Lys Ile Cys His
            100                 105                 110

Ser Arg Ala Phe Gln His Trp Glu Leu Ile Gln Glu Asp Ile Leu Asp
        115                 120                 125

Thr Gly Asn Asp Lys Asn Gly Lys Glu Val Ile Lys Arg Lys Ile
130                 135                 140

Pro Tyr Ile Leu Lys Arg Gln Leu Tyr Glu Asn Lys Pro Arg Arg Pro
145                 150                 155                 160

Tyr Ile Leu Lys Arg Asp Ser Tyr Tyr Tyr
                165                 170

<210> SEQ ID NO 14
<211> LENGTH: 6
<212> TYPE: PRT
<213> ORGANISM: Homo Sapiens
```

```
<400> SEQUENCE: 14

Arg Arg Pro Tyr Ile Leu
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa = D-Lys
<220> FEATURE:
<221> NAME/KEY: VARIANT
<222> LOCATION: (4)..(4)
<223> OTHER INFORMATION: Xaa = L-neo-Trp
<220> FEATURE:
<221> NAME/KEY: VARIANT
<222> LOCATION: (5)..(5)
<223> OTHER INFORMATION: Xaa = tert-Leu

<400> SEQUENCE: 15

Xaa Arg Pro Xaa Xaa Leu
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa = D-Lys
<220> FEATURE:
<221> NAME/KEY: VARIANT
<222> LOCATION: (4)..(4)
<223> OTHER INFORMATION: Xaa = L-neo-Trp

<400> SEQUENCE: 16

Xaa Arg Pro Xaa Ile Leu
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa = N-methyl-Arg
<220> FEATURE:
<221> NAME/KEY: VARIANT
<222> LOCATION: (4)..(4)
<223> OTHER INFORMATION: Xaa = L-neo-Trp
<220> FEATURE:
<221> NAME/KEY: VARIANT
<222> LOCATION: (5)..(5)
<223> OTHER INFORMATION: Xaa = tert-Leu

<400> SEQUENCE: 17

Xaa Lys Pro Xaa Xaa Leu
1               5

<210> SEQ ID NO 18
<211> LENGTH: 6
<212> TYPE: PRT
```

```
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa = N-methyl-Arg
<220> FEATURE:
<221> NAME/KEY: VARIANT
<222> LOCATION: (5)..(5)
<223> OTHER INFORMATION: Xaa = tert-Leu

<400> SEQUENCE: 18

Xaa Lys Pro Trp Xaa Leu
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa = H-Lys-psi-(CH2NH)
<220> FEATURE:
<221> NAME/KEY: VARIANT
<222> LOCATION: (6)..(6)
<223> OTHER INFORMATION: Xaa = Leu-OH

<400> SEQUENCE: 19

Xaa Lys Pro Tyr Ile Xaa
1               5

<210> SEQ ID NO 20
<211> LENGTH: 0
<212> TYPE: PRT
<213> ORGANISM: Artificial sequence
<220> FEATURE:
<223> OTHER INFORMATION: Synthetically generated peptide

<400> SEQUENCE: 20

000

<210> SEQ ID NO 21
<211> LENGTH: 0
<212> TYPE: PRT
<213> ORGANISM: Artificial sequence
<220> FEATURE:
<223> OTHER INFORMATION: Synthetically generated peptide

<400> SEQUENCE: 21

000

<210> SEQ ID NO 22
<211> LENGTH: 0
<212> TYPE: PRT
<213> ORGANISM: Artificial sequence
<220> FEATURE:
<223> OTHER INFORMATION: Synthetically generated peptide

<400> SEQUENCE: 22

000

<210> SEQ ID NO 23
<211> LENGTH: 0
<212> TYPE: PRT
<213> ORGANISM: Artificial sequence
<220> FEATURE:
```

<223> OTHER INFORMATION: Synthetically generated peptide

<400> SEQUENCE: 23

000

<210> SEQ ID NO 24
<211> LENGTH: 76
<212> TYPE: PRT
<213> ORGANISM: Conus geographus

<400> SEQUENCE: 24

Met Gln Thr Ala Tyr Trp Val Met Val Met Met Val Trp Ile Ala
1               5                   10                  15

Ala Pro Leu Ser Glu Gly Gly Lys Leu Asn Asp Val Ile Arg Gly Leu
                20                  25                  30

Val Pro Asp Asp Ile Thr Pro Gln Leu Ile Leu Gly Ser Leu Ile Ser
                35                  40                  45

Arg Arg Gln Ser Glu Gly Gly Ser Asn Ala Thr Lys Lys Pro Tyr
50                  55                  60

Ile Leu Arg Ala Ser Asp Gln Val Ala Ser Gly Pro
65                  70                  75

<210> SEQ ID NO 25
<211> LENGTH: 31
<212> TYPE: PRT
<213> ORGANISM: Homo Sapiens

<400> SEQUENCE: 25

Gly Gly Ser Arg Gly Gly Arg Ile Phe Arg Ser Ser Asp Phe Ala Lys
1               5                   10                  15

Asn Phe Val Gln Thr Asp Leu Pro Phe His Pro Leu Thr Gln Met
                20                  25                  30

<210> SEQ ID NO 26
<211> LENGTH: 12
<212> TYPE: PRT
<213> ORGANISM: Homo Sapiens

<400> SEQUENCE: 26

Arg Ile Phe Arg Ser Ser Asp Phe Ala Lys Asn Phe
1               5                   10

<210> SEQ ID NO 27
<211> LENGTH: 4
<212> TYPE: PRT
<213> ORGANISM: Homo Sapiens

<400> SEQUENCE: 27

Arg Ile Phe Arg
1

<210> SEQ ID NO 28
<211> LENGTH: 5
<212> TYPE: PRT
<213> ORGANISM: Homo Sapiens

<400> SEQUENCE: 28

Phe Ala Lys Asn Phe
1               5

<210> SEQ ID NO 29
<211> LENGTH: 0
<212> TYPE: PRT

```
<213> ORGANISM: Unknown
<220> FEATURE:
<223> OTHER INFORMATION: Synthetically generated peptide

<400> SEQUENCE: 29

000

<210> SEQ ID NO 30
<211> LENGTH: 0
<212> TYPE: PRT
<213> ORGANISM: Unknown
<220> FEATURE:
<223> OTHER INFORMATION: Synthetically generated peptide

<400> SEQUENCE: 30

000

<210> SEQ ID NO 31
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (4)..(4)
<223> OTHER INFORMATION: Xaa = D-neo-Trp

<400> SEQUENCE: 31

Arg Arg Pro Xaa Ile Leu
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (4)..(4)
<223> OTHER INFORMATION: Xaa = L-neo-Trp

<400> SEQUENCE: 32

Arg Arg Pro Xaa Ile Leu
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 33

Arg Arg Pro Xaa Leu Leu
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
```

```
<222> LOCATION: (1)..(1)
<223> OTHER INFORMATION: Xaa = D-Lys
<220> FEATURE:
<221> NAME/KEY: VARIANT
<222> LOCATION: (4)..(4)
<223> OTHER INFORMATION: Xaa = D-neo-Trp
<220> FEATURE:
<221> NAME/KEY: VARIANT
<222> LOCATION: (5)..(5)
<223> OTHER INFORMATION: Xaa = tert-Leu

<400> SEQUENCE: 34

Xaa Arg Pro Xaa Xaa Leu
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa = N-methyl-Arg
<220> FEATURE:
<221> NAME/KEY: VARIANT
<222> LOCATION: (4)..(4)
<223> OTHER INFORMATION: Xaa = L-neo-Trp
<220> FEATURE:
<221> NAME/KEY: VARIANT
<222> LOCATION: (5)..(5)
<223> OTHER INFORMATION: Xaa = tert-Leu

<400> SEQUENCE: 35

Xaa Arg Pro Xaa Xaa Leu
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa = N-methyl-Arg
<220> FEATURE:
<221> NAME/KEY: VARIANT
<222> LOCATION: (2)..(2)
<223> OTHER INFORMATION: Xaa = Diaminobutyric acid
<220> FEATURE:
<221> NAME/KEY: VARIANT
<222> LOCATION: (4)..(4)
<223> OTHER INFORMATION: Xaa = L-neo-Trp
<220> FEATURE:
<221> NAME/KEY: VARIANT
<222> LOCATION: (5)..(5)
<223> OTHER INFORMATION: Xaa = tert-Leu

<400> SEQUENCE: 36

Xaa Xaa Pro Xaa Xaa Leu
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
```

```
<223> OTHER INFORMATION: Xaa = D-Lys
<220> FEATURE:
<221> NAME/KEY: VARIANT
<222> LOCATION: (3)..(3)
<223> OTHER INFORMATION: Xaa = L-neo-Trp
<220> FEATURE:
<221> NAME/KEY: VARIANT
<222> LOCATION: (4)..(4)
<223> OTHER INFORMATION: Xaa = tert-Leu

<400> SEQUENCE: 37

Xaa Pro Xaa Xaa Leu
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa = D-Lys
<220> FEATURE:
<221> NAME/KEY: VARIANT
<222> LOCATION: (3)..(3)
<223> OTHER INFORMATION: Xaa = L-neo-Trp

<400> SEQUENCE: 38

Xaa Pro Xaa Ile Leu
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa = Diaminobutyric acid
<220> FEATURE:
<221> NAME/KEY: VARIANT
<222> LOCATION: (3)..(3)
<223> OTHER INFORMATION: Xaa = L-neo-Trp
<220> FEATURE:
<221> NAME/KEY: VARIANT
<222> LOCATION: (4)..(4)
<223> OTHER INFORMATION: Xaa = tert-Leu

<400> SEQUENCE: 39

Xaa Pro Xaa Xaa Leu
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: Dbu
<220> FEATURE:
<221> NAME/KEY: VARIANT
<222> LOCATION: (3)..(3)
<223> OTHER INFORMATION: Xaa = L-neo-Trp

<400> SEQUENCE: 40

Xaa Pro Xaa Ile Leu
```

<210> SEQ ID NO 41
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (2)..(2)
<223> OTHER INFORMATION: Xaa = D-Orn
<220> FEATURE:
<221> NAME/KEY: VARIANT
<222> LOCATION: (4)..(4)
<223> OTHER INFORMATION: Xaa = L-neo-Trp

<400> SEQUENCE: 41

Arg Xaa Pro Xaa Ile Leu
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (2)..(2)
<223> OTHER INFORMATION: D-Orn
<220> FEATURE:
<221> NAME/KEY: VARIANT
<222> LOCATION: (4)..(4)
<223> OTHER INFORMATION: Xaa = L-neo-Trp
<220> FEATURE:
<221> NAME/KEY: VARIANT
<222> LOCATION: (5)..(5)
<223> OTHER INFORMATION: Xaa = tert-Leu

<400> SEQUENCE: 42

Arg Xaa Pro Xaa Xaa Leu
1               5

<210> SEQ ID NO 43
<211> LENGTH: 33
<212> TYPE: PRT
<213> ORGANISM: Homo sapiens
<220> FEATURE:
<221> NAME/KEY: SIGNAL
<222> LOCATION: (1)..(33)
<223> OTHER INFORMATION: Signal peptide of Sortilin

<400> SEQUENCE: 43

Met Glu Arg Pro Trp Gly Ala Ala Asp Gly Leu Ser Arg Trp Pro His
1               5                   10                  15

Gly Leu Gly Leu Leu Leu Leu Gln Leu Leu Pro Pro Ser Thr Leu
            20                  25                  30

Ser

<210> SEQ ID NO 44
<211> LENGTH: 12
<212> TYPE: PRT
<213> ORGANISM: Homo Sapiens

<400> SEQUENCE: 44

```
Ser Leu Phe Leu Ser Ala Asp Glu Gly Ala Thr Phe
1               5                   10
```

<210> SEQ ID NO 45
<211> LENGTH: 41
<212> TYPE: DNA
<213> ORGANISM: Artificial Sequence
<220> FEATURE:
<223> OTHER INFORMATION: Primer

<400> SEQUENCE: 45
ggtattgagg gtcgcgaacc acactcagag agcaatgtcc c          41

<210> SEQ ID NO 46
<211> LENGTH: 52
<212> TYPE: DNA
<213> ORGANISM: Artificial Sequence
<220> FEATURE:
<223> OTHER INFORMATION: Primer

<400> SEQUENCE: 46
agaggagagt tagagcctca ccgcttgctc ctgtgagtcc tgttgaaggg gg          52

<210> SEQ ID NO 47
<211> LENGTH: 44
<212> TYPE: DNA
<213> ORGANISM: Artificial Sequence
<220> FEATURE:
<223> OTHER INFORMATION: Primer

<400> SEQUENCE: 47
ggtattgagg gtcgcgcccc catgaaagaa gcaaacatcc gagg          44

<210> SEQ ID NO 48
<211> LENGTH: 49
<212> TYPE: DNA
<213> ORGANISM: Artificial Sequence
<220> FEATURE:
<223> OTHER INFORMATION: Primer

<400> SEQUENCE: 48
agaggagagt tagagcctca gcgccggacc ctcatggaca tgtttgcac          49

<210> SEQ ID NO 49
<211> LENGTH: 15
<212> TYPE: PRT
<213> ORGANISM: Artificial Sequence
<220> FEATURE:
<223> OTHER INFORMATION: Linker

<400> SEQUENCE: 49

```
Ala Met Ile Glu Gly Arg Gly Val Gly His His His His His His
1               5                   10                  15
```

<210> SEQ ID NO 50
<211> LENGTH: 15
<212> TYPE: PRT
<213> ORGANISM: Artificial Sequence
<220> FEATURE:
<223> OTHER INFORMATION: Site-directed PCR Clones

<400> SEQUENCE: 50

```
Ala Gly Gly Arg Ile Phe Arg Ser Ser Asp Phe Ala Lys Asn Phe
1               5                   10                  15
```

<210> SEQ ID NO 51
<211> LENGTH: 15

```
<212> TYPE: PRT
<213> ORGANISM: Artificial Sequence
<220> FEATURE:
<223> OTHER INFORMATION: Site-Directed PCR Clone

<400> SEQUENCE: 51

Arg Gly Gly Ala Ile Phe Arg Ser Ser Asp Phe Ala Lys Asn Phe
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Site-Deirected PCR Clone

<400> SEQUENCE: 52

Arg Gly Gly Arg Ile Ala Arg Ser Ser Asp Phe Ala Lys Asn Phe
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Site-Directed PCR Clone

<400> SEQUENCE: 53

Arg Gly Gly Arg Ile Phe Ala Ser Ser Asp Phe Ala Lys Asn Phe
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Site-Directed PCR Clone

<400> SEQUENCE: 54

Arg Gly Gly Arg Ile Phe Arg Ser Ser Asp Ala Ala Lys Asn Phe
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Site-Directed PCR Clone

<400> SEQUENCE: 55

Arg Gly Gly Arg Ile Phe Arg Ser Ser Asp Phe Ala Ala Asn Phe
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Site-Directed PCR Clone

<400> SEQUENCE: 56

Arg Gly Gly Arg Ile Phe Arg Ser Ser Asp Phe Ala Lys Asn Ala
1               5                   10                  15

<210> SEQ ID NO 57
<211> LENGTH: 15
<212> TYPE: PRT
<213> ORGANISM: Artificial Sequence
```

```
<220> FEATURE:
<223> OTHER INFORMATION: Site-Directed PCR Clone

<400> SEQUENCE: 57

Arg Gly Gly Ala Ile Ala Ala Ser Ser Asp Ala Ala Lys Asn Phe
1               5                   10                  15
```

MODULATION OF ACTIVITY OF PRONEUROTROPHINS

CROSS-REFERENCE TO RELATED APPLICATIONS

The present application is a §371 U.S. National Stage Application of PCT International Application No. PCT/DK2007/000567 filed Dec. 21, 2007, which claims the benefit of priority under 35 U.S.C. §119(e) of U.S. Provisional Application No. 60/880,771, filed Jan. 16, 2007, and which claims the benefit of priority under 35 U.S.C. §119(a-d) of Danish Application No. PA200601692, filed Dec. 21, 2006. Each of these applications is hereby incorporated by reference in its entirety.

All patent and non-patent references cited in the application, or in the present application, are also hereby incorporated by reference in their entirety.

FIELD OF INVENTION

The present invention relates to compositions which are useful in inhibiting pro-neurotrophin activity, as well as methods for the preparation and use thereof. Methods are also provided for screening for agents for use in said compositions.

BACKGROUND OF INVENTION

The Neurotrophin Family

Neurotrophins are dimeric peptide hormones. The first member of the neurotrophin family to be discovered was nerve growth factor (NGF), which plays an important role in processes such as the development of sensory and sympathetic neurons of the peripheral nervous system (Levi-Montalcini, R. and Angeleeti, P. U, Physiol. Rev. 48, 534-569 (1968)). The next member of the neurotrophin family to be isolated was brain-derived neurotrophic factor (BDNF), also referred to as neurotrophin-2 (NT-2), the sequence of which was published by Leibrock, J. et al. in 1989 (Nature 341, 149-152). In 1990 several groups identified a neurotrophic factor originally called neuronal factor (NF), now referred to as neurotrophin-3 (NT-3) (Ernfors et al., Proc. Natl: Acad. Sci. USA 87, 5454-5458 (1990); Hohn et al., Nature 344, 339; Maisonpierre et al., Science 247, 1446; Rosenthal et al., Neuron 4, 767; Jones and Reichardt, Proc. Natl. Acad. Sci. USA 87, 8060-8064; Kaisho et al., FEBS Lett. 266, 187). Neurotrophins-4 and -5 were then added to the family (Neuron 6, 845-858 (1991); Berkmeier, L. R. et al., Neuron 7, 857-866 (1991); Ip et al., Proc. Natl. Acad. Sci. USA 89, 3060-3064 (1992)). The effects of neurotrophins depend upon their levels of availability, their affinity of binding to transmembrane receptors and the downstream signalling cascades that are stimulated after receptor activation.

Receptors for the Neurotrophin Family

In a similar way to other polypeptide growth factors, neurotrophins affect their target cells through interactions with cell surface receptors. According to current knowledge, neurotrophins bind to two discrete receptor types which can be distinguished pharmacologically: the Trk and $p75^{NTR}$ neurotrophin receptors. $p75^{NTR}$ is a member of the Fas/tumour necrosis factor (TNF) receptor family, and can interact with all the mammalian members of the neurotrophin family with equal affinities (Rodriguez-Tebar et al. 1990, Neuron 4:487-492; Barker and Murphy, 1992, Mol. Cell. Biochem. 100:1-15). Cells expressing TrkA, a tyrosine kinase receptor originally identified as a human oncogene (Mltin-Zanca et al, Nature 319:743-748) bind solely to NGF and exhibit significantly slower dissociation kinetics (Jing et al. 1992, Neurol. 9:1067-1079; Loeb and Greene, 1993, Neuroscience 13:2919-2929). BDNF binds the TrkB receptor only, but NT-3 can bind all three Trk (A, B and C) receptors, with a preference for TrkC. NT-4/5 can bind both TrkA and TrkB (Ip et al. PNAS 89:3060-3064; Klein et al. Neuron 9:947-956). NT-7 does not interact with TrkB or TrkC but can however induce tyrosine phosphorylation of TrkA, indicating a similar receptor specificity as NGF (Nilsson et al., FEBS Lett (1998) March 13; 424(3):285-90). Recombinant purified NT-6 also has a spectrum of actions similar to NGF but with a lower potency (Gotz et al., Nature (1994) November 17; 372(6503): 266-9).

The Neurotrophin Family: Precursor Proteins

The biology of the neurotrophin family is complex: the neurotrophins are synthesised intracellularly as 30-35 kDa precursor proteins, containing a signal peptide a pro-domain and glycosylation sites. During processing precursor proteins are also cleaved at a dibasic cleavage site by the calcium-dependent serine protease furin and other members of the prohormone convertase family, within the Golgi apparatus. The 12-14 kDa C-terminal product of this cleavage is the mature, biologically active neurotrophin (Seidah et al, Biochem. J. (1996) 314:951-960).

Clinically Relevant Roles of the Neurotrophin Family

Neurotrophins are of clinical interest as they play an important role in neuronal cell survival and differentiation (Thoenen 1991, Trends Neurosci. 14: 165-170; Raffioni et al. 1991, Ann. Rev. Biochem. 62:823-850; Chao, 1992, Neuron 9:583-593; Barbacid 1993, Oncogene 8:2033-2042). Trk receptors transmit signals promoting neuronal survival, whereas $p75^{NTR}$ can induce neuronal apoptosis as well as neuronal survival depending on co-expression of Trk (Miller et al., Cell. Mol. Life. Sci. 58:1045-1053 (2001)). Certainly, it has been demonstrated that activation of TrkA receptors can negate the proapoptotic effect of $p75^{NTR}$ in some but not all tissues (Yoon et al., J. Neurosci. (1998) 18:3273-3281; Volosin et al., J. Neurosci. (2006) 26:7756-7766).

It has been demonstrated that the propeptides of neurotrophins play important biological roles: at least three neurotrophin precursor proteins, proNGF, pro-BDNF and proNT-3 and their proteolytically processed and mature counterpart, NGF, BDNF, NT-3 products differentially activate pro- and anti-apoptotic cellular responses through preferential activation of $p75^{NTR}$ and Trk receptors, respectively—pro-NGF having enhanced affinity for $p75^{NTR}$ receptors and a reduced affinity for Trk receptors relative to the mature forms of NGF. Indeed, it has been demonstrated that pro-NGF induces $p75^{NTR}$-dependent apoptosis in cultured neurons with minimal activation of TrkA-mediated differentiation or survival (Lee et al., Science (2001), 294:1945-1948).

Furthermore, neurotrophins are of clinical interest as it is known that both up-regulation of neurotrophins and increased $p75^{NTR}$ expression occur under pathological and inflammatory conditions, especially after nerve injury and damage to the vascular system. Indeed, Soilu-Hanninen et al. have demonstrated that the proapoptotic functions of $p75^{NTR}$ are directly implicated in injury-induced apoptosis (Soilu-Hanninen et al., J. Neurosci. 19:4824-4838 (1999)). Recently, it was also demonstrated that proNGF induces p75 mediated death of oligodendrocytes and corticospinal neurons following spinal cord injury (Beatty et al., Neuron (2002), vol. 36, pp. 375-386; Giehl et al, Proc. Natl. Acad. Sci USA (2004), vol. 101, pp 6226-30) and death of basal forebrain neurons in response to kainic acid-induced seizures (Volosin et al, J. Neuroscience (2006), vol. 26, pp 7756-7766).

It has been hypothesized that an imbalance between the precursor and mature form of neurotrophic factors is responsible for the degeneration of selective neuronal populations as it occurs in Parkinson's disease, Alzheimer's disease and amyotrophic lateral sclerosis, and that application of corresponding neurotrophic factor might prevent neuronal degeneration [Appel, S. H., "A unifying hypothesis for the cause of amyotrophic lateral sclerosis, parkinsonism, and Alzheimer's disease," Ann. Neurol. 10:499-505 (1981), Cunello C and Bruno M. A., Neurochem. Res. (2007) 32:1041-45].

Another reason for interest in targeting neurotrophin pathways for therapy is that studies have provided supporting evidence for the involvement of neurotrophins in depression and antidepressant action (Duman et al. Arch Gen Psychiatry (1997) 54:597-606); for instance infusion of BDNF into the hippocampus has produced an antidepressant effect in two behavioural models of depression (Shirayama et al. (2002), J Neurosci 22(8): 3251-3261). Moreover, a single nucleotide polymorphism in the bdnf gene leading to a valine (Val) to methionine (Met) substitution at codon 66 in the pro-domain ($BDNF_{Met}$) was found to be associated with increased susceptibility in humans heterozygous for the polymorphism to neuropsychiatric disorders including Alzheimer's disease, Parkinson's disease, depression, and bipolar disorder (Chen et al, J. Neuroscience (2005), vol. 25:6156-6166; Kuipers and Bramham Curr. Opin. Drug Discov. Devel. (2006) 9(5):580-6; Bath and Lee, Cogn. Affect. Behav. Neurosci (2006) 1:79-85). In addition, humans heterozygous for $BDNF_{Met}$ were shown to have memory impairments (Egan et al, Cell (2003)1 vol. 112, pp 257-269).

The Vps10p-Domain Receptor Family

Sortilin (or NTR-3 or GP95), (SEQ ID NO. 1) is a type I membrane receptor expressed in a number of tissues, including the brain, spinal cord, testis and skeletal muscle (Petersen et al., J. Biol. Chem., 272:3599-3605 (1997); Herman-Borgmeyer et al., Mol. Brain. Res., 65:216-219 (1999)). Sortilin belongs to a family of receptors comprising Sortilin, SorLA (Jacobsen et al., J. Biol. Chem., 271:31379-31383 (1996)), SorCS1, SorCS2 and SorCS3. All the receptors in this family share the structural feature of an approximately 600-amino acid N-terminal domain with a strong resemblance to each of the two domains which constitute the luminal portion of the yeast sorting receptor Vps10p (Marcusson, E. G., et al., Cell, 77:579-586 (1994)). The Vps10p-domain includes a C-terminal segment containing 10 conserved cysteines and an N-terminal propeptide of 40-80 amino acids.

In Sortilin, the propeptide exhibits high affinity binding to the fully processed receptor. Prevention of propeptide cleavage essentially inhibits ligand binding to Sortilin, indicating that the propeptide sterically hinders ligands from gaining access to their binding sites on the receptor (Petersen et al., EMBO J., 18:595-604, 1999).

Some progress has been made as to an understanding of the role of this family: there is evidence suggesting that Sortilin at least contains YXXϕ and dileucine motifs, conforming to potent signals for Golgi-endosome sorting (Nielsen et al., EMBO 20(9):2180-2190). It is probable that the other members of the family may also fulfil a similar "sorting" function, not least because they all exhibit homology to Vps10p, the sorting receptor for carboxypeptidase Y (CPY) in yeast. Only a small proportion of Sortilin receptors are present on the cell surface (Mazella et al. J. Biol. Chem. (1998) 273, 26273-26276; Morris et al. J. Biol. Chem. (1998) 273:3582-3587), although expression on the surface membrane can be upregulated by stimuli including insulin in 3T3-L1 adipocytes (Morris et al. J. Biol. Chem. (1998) 273:3582-3587) and neurotensin in embryonic neurons (Chabry et al., J. Biol. Chem. (1993), 286:17138-17144).

Inhibiting Proneurotrophin Activity: the Current State of the Art

Certainly, current understanding of the biological roles of neurotrophins makes the neurotrophin family an attractive target for therapeutic intervention, and some methods for modulation of neurotrophin activity are known:

Mehar M et al., Eur. J. Neruosci. (2006) 24:1575-1580 and Massa S. M. et al, J. Neurosci. (2006), 26:5288-5300 describe how p75 can be used as a drug target to interfere with death-induction following ligand (e.g. proNGF) binding to p75.

WO 2004/056385 discloses general methods for inhibiting binding between Vps10-p domain receptors and neurotrophins/pro-neurotrophins but fails to teach the specific binding site.

SUMMARY OF INVENTION

The present inventors have now identified the binding site on the Sortilin receptor for pro-neurotrophins.

The present invention provides at least one agent capable of inhibiting binding of a pro-neurotrophin to a binding site of a Sortilin receptor, wherein said pro-neurotrophin binds to a binding site on Sortilin comprising an amino acid sequence being at least 70% identical to SEQ ID NO. 25, and wherein said agent either binds to said binding site, or comprises an amino acid sequence being at least 70% identical to SEQ ID NO. 25 or a fragment thereof, in the manufacture of a medicament, for treating and/or preventing and/or ameliorating neurological, neuropsychiatric, and/or ocular diseases, disorders and degeneration, obesity, diabetes, pain and/or nociception in an animal.

In a further aspect, the present invention the at least one agent binds to an amino acid sequence having at least 70% sequence identity to SEQ ID NO. 26 and/or SEQ ID NO. 27 and/or SEQ ID NO. 28, thereby inhibiting binding of a pro-neurotrophin to a Sortilin receptor.

In a further aspect, the at least one agent binds to an amino acid sequence having at least 70% sequence identity to the pro-domain of a pro-neurotrophin, thereby inhibiting binding of said pro-neurotrophin to a Sortilin receptor In yet another aspect the present invention provides at least one agent capable of inhibiting binding of a pro-neurotrophin to a Sortilin receptor, said at least one agent having at least 90% sequence identity to any of SEQ ID NO. 14, SEQ ID NO. 15, SEQ ID NO. 16, SEQ ID NO. 17, SEQ ID NO. 18, SEQ ID NO. 19, SEQ ID NO. 24, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, SEQ ID NO. 40, SEQ ID NO. 41 and SEQ ID NO. 42, in the manufacture of a medicament, for treating and/or preventing and/or ameliorating neurological, neuropsychiatric, and/or ocular diseases, disorders and degeneration, obesity, diabetes, pain and/or nociception in an animal.

In another aspect the agents of the present invention are capable of inhibiting the activity of one or more proneurotrophins in an animal and methods for treatment of a disease or disorder in an individual by inhibition of neurotrophin activity. Accordingly, in one aspect the present invention relates to a method for inhibiting the activity of at least one pro-neurotrophin in an animal comprising administering to said animal a sufficient amount of an agent capable of (i) binding to a receptor of the Vps10p-domain receptor family and/or
(ii) interfering with binding between a receptor of the Vps10p-domain receptor family and a pro-neurotrophin and/or
(iii) decreasing the expression of a receptor of the Vps10p-domain receptor family In a further aspect agents of the present invention provides agents preventing physical interaction between $p75^{NTR}$ and Sortilin.

Another aspect of the present invention relates to a method or use of at least one agent capable of decreasing the activity of Vps10p-domain receptors in the manufacture of a medicament for treating and/or preventing and/or ameliorating neurological, neuropsychiatric and/or ocular diseases, disorders, degeneration, obesity, diabetes, pain and/or nociception in an animal.

Methods for screening for agents capable of modulating proneurotrophin activity and agents selected using these screening methods are also disclosed, as are methods for determining the effect of an agent on one or more pro-neurotrophins in cells. The present invention also pertains to methods for modulating the transport of one or more pro-neurotrophins.

Pharmaceutical compositions comprising the agents of the invention and their use for preventing, treating and/or ameliorating proneurotrophin related diseases are also disclosed.

DETAILED DESCRIPTION OF THE INVENTION

Definitions

The term inhibiting as used herein refers to the prevention of binding between two or more components. In the present invention agents capable of inhibiting binding between a Vps10p-domain receptor and a pro-neurotrophin are provided.

The term "binding" as used herein refers to the transient or longer lasting attraction or binding of two or more moieties to one another, mediated by physical forces such as e.g. electrostatic interactions, hydrophobic interactions, dipole-dipole interactions and hydrogen bonds. The term "hydrophobic interaction" as used herein refers to any interaction occurring between essentially non-polar (hydrophobic) components located within attraction range of one another in a polar environment (e.g. water). As used herein, attraction range is on the scale of about 100 nm. A particular type of hydrophobic interaction is exerted by "Van der Waal's forces", i.e. the attractive forces between non-polar molecules that are accounted for by quantum mechanics. Van der Waal's forces are generally associated with momentary dipole moments which are induced by neighbouring molecules and which involve changes in electron distribution. The term "hydrogen bond" as used herein refers to an attractive force, or bridge, which may occur between a hydrogen atom which is bonded covalently to an electronegative atom, for example, oxygen, sulphur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding). The term "electrostatic interaction" as used herein refers to any interaction occurring between charged components, molecules or ions, due to attractive forces when components of opposite electric charge are attracted to each other. Examples include, but are not limited to: ionic interactions, covalent interactions, interactions between a ion and a dipole (ion and polar molecule), interactions between two dipoles (partial charges of polar molecules), hydrogen bonds and London dispersion bonds (induced dipoles of polarizable molecules). Thus, for example, "ionic interaction" or "electrostatic interaction" refers to the attraction between a first, positively charged molecule and a second, negatively charged molecule. Ionic or electrostatic interactions include, for example, the attraction between a negatively charged bioactive agent (input examples relevant to this invention). The term "dipole-dipole interaction" as used herein refers to the attraction which can occur among two or more polar molecules. Thus, "dipole-dipole interaction" refers to the attraction of the uncharged, partial positive end of a first polar molecule to the uncharged, partial negative end of a second polar molecule. "Dipole-dipole interaction" also refers to intermolecular hydrogen bonding.

Functional equivalents and variants of polynucleotides encoding a pro-neurotrophin activity modulator and polypeptides comprising such a proneurotrophin activity modulator: "functional equivalents" and "variants" are used interchangeably herein. In one preferred embodiment of the invention there is also provided variants of proneurotrophin activity modulator and variants of fragments thereof. When being polypeptides, variants are determined on the basis of their degree of identity or their homology with a predetermined amino acid sequence, said predetermined amino acid sequence being one of SEQ ID NO: proneurotrophin activity modulator, or, when the variant is a fragment, a fragment of any of the aforementioned amino acid sequences, respectively.

The term inhibiting binding between a proneurotrophin and a Sortilin receptor as used herein refer to a method of providing an agent capable of preventing the binding of a proneurotrophin to a Sortilin receptor and in particular binding to a part of the Sortilin receptor comprising any of the SEQ ID NO. 25 to 28 or any fragment or variant thereof or binding of said agent to said proneurotrophin, thus preventing binding of said pro-neurotrophin to SEQ ID NO. 25, SEQ ID NO. 26, SEQ ID NO. 27 or SEQ ID NO. 28 or any fragment or variant thereof.

Accordingly, variants preferably have at least 70% sequence identity, for example at least 72% sequence identity, for example at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with any of the predetermined sequences.

Sequence identity is determined in one embodiment by utilising fragments of proneurotrophin activity modulator peptides comprising at least 25 contiguous amino acids and having an amino acid sequence which is at least 80%, such as 85%, for example 90%, such as 95%, for example 99% identical to the amino acid sequence of any of SEQ ID NO: 1, SEQ ID NO: 2, SEQ ID NO: 3, SEQ ID NO: 4, SEQ ID NO: 5, SEQ ID NO: 25, SEQ ID NO: 26, SEQ ID NO: 27 AND SEQ ID NO: 28 respectively, wherein the percent identity is determined with the algorithm GAP, BESTFIT, or FASTA in the Wisconsin Genetics Software Package Release 7.0, using default gap weights.

The following terms are used to describe the sequence relationships between two or more polynucleotides: "predetermined sequence", "comparison window", "sequence identity", "percentage of sequence identity", and "substantial identity".

A "predetermined sequence" is a defined sequence used as a basis for a sequence comparison; a predetermined sequence may be a subset of a larger sequence, for example, as a segment of a full-length DNA or gene sequence given in a sequence listing, such as a polynucleotide sequence of SEQ ID NO:1, or may comprise a complete DNA or gene sequence. Generally, a predetermined sequence is at least 20 nucleotides in length, frequently at least 25 nucleotides in length, and often at least 50 nucleotides in length.

Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a predetermined sequence of at least 20 contiguous nucleotides and wherein the portion of the polynucleotide sequence in the comparison window may comprise additions or deletions (i.e., gaps) of 20 percent or less as compared to the predetermined sequence (which does not comprise additions or deletions) for optimal alignment of the two sequences.

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a predetermined sequence over a comparison window of at least 20 nucleotide positions, frequently over a window of at least 25-50 nucleotides, wherein the percentage of sequence identity is calculated by comparing the predetermined sequence to the polynucleotide sequence which may include deletions or additions which total 20 percent or less of the predetermined sequence over the window of comparison. The predetermined sequence may be a subset of a larger sequence, for example, as a segment of the full-length SEQ ID NO:1 polynucleotide sequence illustrated herein.

As applied to polypeptides, a degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences.

An "unrelated" or "non-homologous" sequence shares less than 40% identity, though preferably less than 25% identity, with one of the proneurotrophin activity modulator polypeptide sequences of the present invention. The term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine.

Additionally, variants are also determined based on a predetermined number of conservative amino acid substitutions as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:

i) Amino acids having polar side chains (Asp, Glu, Lys, Arg, H is, Asn, Gln, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, H is, Pro)
v) Amino acids having aromatic side chains (Phe, Tyr, Trp)
vi) Amino acids having acidic side chains (Asp, Glu)
vii) Amino acids having basic side chains (Lys, Arg, H is)
viii) Amino acids having amide side chains (Asn, Gln)
ix) Amino acids having hydroxy side chains (Ser, Thr)
x) Amino acids having sulphur-containing side chains (Cys, Met),
xi) Neutral, weakly hydrophobic amino acids (Pro, Ala, Gly, Ser, Thr)

xii) Hydrophilic, acidic amino acids (Gln, Asn, Glu, Asp), and xiii) Hydrophobic amino acids (Leu, Ile, Val)

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

The addition or deletion of at least one amino acid may be an addition or deletion of from preferably 2 to 250 amino acids, such as from 10 to 20 amino acids, for example from 20 to 30 amino acids, such as from 40 to 50 amino acids. However, additions or deletions of more than 50 amino acids, such as additions from 50 to 100 amino acids, addition of 100 to 150 amino acids, addition of 150-250 amino acids, are also comprised within the present invention. The deletion and/or the addition may—independently of one another—be a deletion and/or an addition within a sequence and/or at the end of a sequence.

The polypeptide fragments according to the present invention, including any functional equivalents thereof, may in one embodiment comprise less than 250 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues.

"Functional equivalency" as used in the present invention is, according to one preferred embodiment, established by means of reference to the corresponding functionality of a predetermined fragment of the sequence.

Functional equivalents or variants of a proneurotrophin activity modulator will be understood to exhibit amino acid sequences gradually differing from the preferred predetermined proneurotrophin activity modulator sequence, as the number and scope of insertions, deletions and substitutions including conservative substitutions increase. This difference is measured as a reduction in homology between the preferred predetermined sequence and the fragment or functional equivalent.

All fragments or functional equivalents of SEQ ID NO: proneurotrophin activity modulator are included within the scope of this invention, regardless of the degree of homology that they show to the respective, predetermined proneurotrophin activity modulator sequences disclosed herein. The reason for this is that some regions of the proneurotrophin activity modulator are most likely readily mutatable, or capable of being completely deleted, without any significant effect on the binding activity of the resulting fragment.

A functional variant obtained by substitution may well exhibit some form or degree of native proneurotrophin activity modulator activity, and yet be less homologous, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of identity is not a principal measure of a fragment being a variant or functional equivalent of a preferred predetermined fragment according to the present invention.

The homology between amino acid sequences may be calculated using well known scoring matrices such as any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90.

Fragments sharing homology with fragments of SEQ ID NO:1 to 42, respectively, are to be considered as falling within the scope of the present invention when they are preferably at least about 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with said predetermined fragment sequences, respectively. According to one embodiment of the invention, the homology percentages refer to identity percentages.

Additional factors that may be taken into consideration when determining functional equivalence according to the meaning used herein are i) the ability of antisera to detect a proneurotrophin activity modulator fragment according to the present invention, or ii) the ability of the functionally equivalent proneurotrophin activity modulator fragment to compete with the corresponding proneurotrophin activity modulator in an assay. One method of determining a sequence of immunogenically active amino acids within a known amino acid sequence has been described by Geysen in U.S. Pat. No. 5,595,915 and is incorporated herein by reference.

A further suitably adaptable method for determining structure and function relationships of peptide fragments is described in U.S. Pat. No. 6,013,478, which is herein incorporated by reference. Also, methods of assaying the binding of an amino acid sequence to a receptor moiety are known to the skilled artisan.

In addition to conservative substitutions introduced into any position of a preferred predetermined proneurotrophin activity modulator, or a fragment thereof, it may also be desirable to introduce non-conservative substitutions in any one or more positions of such a proneurotrophin activity modulator.

A non-conservative substitution leading to the formation of a functionally equivalent fragment of proneurotrophin activity modulator would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Variants obtained by substitution of amino acids may in one preferred embodiment be made based upon the hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In addition to the variants described herein, sterically similar variants may be formulated to mimic the key portions of the variant structure and that such compounds may also be used in the same manner as the variants of the invention. This may be achieved by techniques of modelling and chemical designing known to those of skill in the art. It will be understood that all such sterically similar constructs fall within the scope of the present invention.

In a further embodiment the present invention relates to functional variants comprising substituted amino acids having hydrophilic values or hydropathic indices that are within +/−4.9, for example within +/−4.7, such as within +/−4.5, for example within +/−4.3, such as within +/−4.1, for example within +/−3.9, such as within +/−3.7, for example within +/−3.5, such as within +/−3.3, for example within +/−3.1, such as within +/−2.9, for example within +/−2.7, such as within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference).

The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

The amino acid hydrophilicity values are: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

In addition to the peptidyl compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same or other proneurotrophin activity modulator fragments and/or proneurotrophin activity modulator molecules, including dimers or unrelated chemical moieties. Such functional equivalents are prepared by linkage of functionalities to groups which are found in fragment including at any one or both of the N- and C-termini, by means known in the art.

Functional equivalents may thus comprise fragments conjugated to aliphatic or acyl esters or amides of the carboxyl terminus, alkylamines or residues containing carboxyl side chains, e.g., conjugates to alkylamines at aspartic acid residues; O-acyl derivatives of hydroxyl group-containing residues and N-acyl derivatives of the amino terminal amino acid or amino-group containing residues, e.g. conjugates with fMet-Leu-Phe or immunogenic proteins. Derivatives of the acyl groups are selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups.

Covalent or aggregative functional equivalents and derivatives thereof are useful as reagents in immunoassays or for affinity purification procedures. For example, a fragment of proneurotrophin activity modulator according to the present invention may be insolubilized by covalent bonding to cyanogen bromide-activated Sepharose by methods known per se or adsorbed to polyolefin surfaces, either with or without glutaraldehyde cross-linking, for use in an assay or purification of anti-neurotrophin activity modulator antibodies or cell surface receptors. Fragments may also be labelled with a detectable group, e.g., radioiodinated by the chloramine T procedure, covalently bound to rare earth chelates or conjugated to another fluorescent moiety for use in e.g. diagnostic assays.

Mutagenesis of a preferred predetermined fragment of proneurotrophin activity modulator can be conducted by making amino acid insertions, usually on the order of about from 1 to 10 amino acid residues, preferably from about 1 to 5 amino acid residues, or deletions of from about from 1 to 10 residues, such as from about 2 to 5 residues.

In one embodiment the fragment of proneurotrophin activity modulator is synthesised by automated synthesis. Any of the commercially available solid-phase techniques may be employed, such as the Merrifield solid phase synthesis method, in which amino acids are sequentially added to a growing amino acid chain (see Merrifield, J. Am. Chem. Soc. 85:2149-2146, 1963).

Equipment for automated synthesis of polypeptides is commercially available from suppliers such as Applied Biosystems, Inc. of Foster City, Calif., and may generally be operated according to the manufacturer's instructions. Solid phase synthesis will enable the incorporation of desirable amino acid substitutions into any fragment of proneurotrophin activity modulator according to the present invention. It will be understood that substitutions, deletions, insertions or any subcombination thereof may be combined to arrive at a final sequence of a functional equivalent. Insertions shall be understood to include amino-terminal and/or carboxyl-terminal fusions, e.g. with a hydrophobic or immunogenic protein or a carrier such as any polypeptide or scaffold structure capable as serving as a carrier.

Oligomers including dimers including homodimers and heterodimers of fragments of proneurotrophin activity modulator according to the invention are also provided and fall under the scope of the invention. Proneurotrophin activity modulator functional equivalents and variants can be produced as homodimers or heterodimers with other amino acid sequences or with native proneurotrophin activity modulator sequences. Heterodimers include dimers containing immunoreactive pro-neurotrophin activity modulator fragments as well as proneurotrophin activity modulator fragments that need not have or exert any biological activity.

Neurotrophin activity modulator fragments according to the invention may be synthesised both in vitro and in vivo. Method for in vitro synthesis are well known, and methods being suitable or suitably adaptable to the synthesis in vivo of pro-neurotrophin activity modulator are also described in the prior art. When synthesized in vivo, a host cell is transformed with vectors containing DNA encoding pro-neurotrophin activity modulator or a fragment thereof. A vector is defined as a replicable nucleic acid construct. Vectors are used to mediate expression of proneurotrophin activity modulator. An expression vector is a replicable DNA construct in which a nucleic acid sequence encoding the predetermined proneurotrophin activity modulator fragment, or any functional equivalent thereof that can be expressed in vivo, is operably linked to suitable control sequences capable of effecting the expression of the fragment or equivalent in a suitable host. Such control sequences are well known in the art.

Cultures of cells derived from multicellular organisms represent preferred host cells. In principle, any higher eukaryotic cell culture is workable, whether from vertebrate or invertebrate culture. Examples of useful host cell lines are VERO and HeLa cells, Chinese hamster ovary (CHO) cell lines, and WI38, BHK, COS-7, 293 and MDCK cell lines. Preferred host cells are eukaryotic cells known to synthesize endogenous proneurotrophin activity modulator. Cultures of such host cells may be isolated and used as a source of the fragment, or used in therapeutic methods of treatment, including therapeutic methods aimed at promoting or inhibiting a growth state, or diagnostic methods carried out on the human or animal body.

Pharmaceutical agent: the terms "pharmaceutical agent" or "drug" or "medicament" refer to any therapeutic or prophylactic agent which may be used in the treatment (including the prevention, diagnosis, alleviation, or cure) of a malady, affliction, condition, disease or injury in a patient. Therapeutically useful genetic determinants, peptides, polypeptides and polynucleotides may be included within the meaning of the term pharmaceutical or drug. As defined herein, a "therapeutic agent," "pharmaceutical agent" or "drug" or "medicament" is a type of bioactive agent.

The term "bioactive agent" as used herein refers to any a substance which may be used in connection with an application that is therapeutic or diagnostic, such as, for example, in methods for diagnosing the presence or absence of a disease in a patient and/or methods for the treatment of a disease in a patient. "Bioactive agent" refers to substances, which are capable of exerting a biological effect in vitro and/or in vivo. The bioactive agents may be neutral, positively or negatively charged. Suitable bioactive agents include, for example, prodrugs, diagnostic agents, therapeutic agents, pharmaceutical agents, drugs, oxygen delivery agents, blood substitutes, synthetic organic molecules, polypeptides, peptides, vitamins, steroids, steroid analogues and genetic determinants, including nucleosides, nucleotides and polynucleotides.

Treatment: the term "treatment" as used herein refers to a method involving therapy including surgery of a clinical condition in an individual including a human or animal body. The therapy may be ameliorating, curative or prophylactic, i.e. reducing the risk of acquiring a disease.

antisense-RNA: an RNA molecule capable of causing gene silencing by specifically binding to an mRNA molecule of interest.

antisense-DNA: a DNA molecule capable of causing gene silencing by specifically binding to an mRNA molecule of interest.

siRNA: "small interfering RNA" (siRNA) is a short (often, but not restricted to, less than 30 nucleotides long) double-stranded RNA molecule capable of causing gene-specific silencing in mammalian cells Gene "silencing": a process leading to reduced expression of endogenous genes. Gene silencing is preferably the result of post-transcriptional reduction of gene expression.

Up-regulation of expression: a process leading to increased expression of genes, preferably of endogenous genes.

In vitro/in vivo: the terms are used in their normal meaning.

Polypeptide: The term "polypeptide" as used herein refers to a molecule comprising at least two amino acids. The amino acids may be natural or synthetic. "Oligopeptides" are defined herein as being polypeptides of length not more than 100 amino acids. The term "polypeptide" is also intended to include proteins, i.e. functional biomolecules comprising at least one polypeptide; when comprising at least two polypeptides, these may form complexes, be covalently linked or may be non-covalently linked. The polypeptides in a protein can be glycosylated and/or lipidated and/or comprise prosthetic groups.

"Polynucleotide" as used herein refers to a molecule comprising at least two nucleic acids. The nucleic acids may be naturally occurring or modified, such as locked nucleic acids (LNA), or peptide nucleic acids (PNA). Polynucleotide as used herein generally pertains to i) a polynucleotide comprising a predetermined coding sequence, or i) a polynucleotide encoding a predetermined amino acid sequence, or iii) a polynucleotide encoding a fragment of a polypeptide encoded by polynucleotides (i) or (ii), wherein said fragment has at least one predetermined activity as specified herein; and iv) a polynucleotide the complementary strand of which hybridizes under stringent conditions with a polynucleotide as defined in any one of (i), (ii) and (iii), and encodes a polypeptide, or a fragment thereof, having at least one predetermined activity as specified herein; and v) a polynucleotide comprising a nucleotide sequence which is degenerate to the nucleotide sequence of polynucleotides (iii) or (iv); or the complementary strand of such a polynucleotide.

A "purified antibody" is an antibody at least 60 weight percent of which is free from the polypeptides and naturally-occurring organic molecules with which it is naturally associated. Preferably, the preparation comprises antibody in an amount of at least 75 weight percent, more preferably at least 90 weight percent, and most preferably at least 99 weight percent.

DETAILED DESCRIPTION

The present inventors have identified that proneurotrophins bind to the Sortilin receptor of the Vps10p-domain receptor family which results in apoptosis when a ternery complex is formed by the co-binding of $p75^{NTR}$.

Accordingly, the present invention relates to modulation of the activity of at least one proneurotrophin.

Without being bound by theory it is believed that Vps10p-domain receptor family is involved in one or more of the following mechanisms in relation to proneurotrophins:

Retrograde transport, including uptake of proneurotrophin and p75$^{NTR}$

Transport within biosynthetic pathways, including sorting of proneurotrophin and transport from the Golgi network Release of proneurotrophins Signalling, including modulation of cellular transport and signalling by formation of ternary complexes with p75 and pro-neurotrophin Thus, one aspect of the present invention is a method for modulating the activity of at least one pro-neurotrophin in a single cell or an organism, including an animal, comprising administering to said animal a sufficient amount of an agent capable of binding to a receptor of the Vps10p-domain receptor family or capable of interfering with binding between a receptor of the Vps10p-domain receptor family and a pro-neurotrophin.

Receptors of the Vps10p-Domain Receptor Family

The term "receptor of the Vps10p family" refers to a family of receptors characterised by having an N-terminal Vps10p domain; said Vpsp10p domain family comprises SorLA, Sortilin, SorCS1, SorCS2, or SorCS3, see FIG. 1. In one embodiment of the present invention, any of the receptors of the Vps10p domain family may be used; more preferably, the receptor comprises the Vps10p domain, the 10 CC module, a transmembrane segment as well as a cytoplasmic segment mediating cellular sorting and internalization as well as mediating binding to cytoplasmic adaptors affecting cellular signalling. In particular the receptor used is Sortilin.

Neurotrophins/Pro-Neurotrophins

The term "neurotrophin" as used herein refers to any member of the neurotrophin family, said neurotrophin family comprising nerve growth factor (NGF), brain-derived neurotrophic factor (BDNF), neurotrophin-3 (NT-3) and neurotrophin-4/5 (NT-4/5). In one embodiment of the present invention, any member of the neurotrophin family may be used; however, it is preferred that the neurotrophin is NGF or BDNF.

The term "pro-neurotrophin" as used herein may refer to any pro-neurotrophin family comprising a pro-domain operatively linked to the corresponding mature neurotrophin, said family of pro-neurotrophins comprising pro-NGF, pro-BDNF, pro-NT-3 and pro-NT-4/5. In one embodiment of the present invention, any pro-neurotrophin may be used, however it is preferred that the pro-neurotrophin is pro-NGF or pro-BDNF.

Inhibition of Proneurotrophin Activity

The terms "proneurotrophin-mediated" activity, "activity of a proneurotrophin" or "proneurotrophin activity" refer to a biological activity that is normally promoted, either directly or indirectly, in the presence of a proneurotrophin or neurotrophin. Pro-neurotrophin activities include, but are not restricted to differentially activating both pro- and anti-apoptotic cellular responses, through preferential activation of p75$^{NTR}$ or TrkA receptors respectively. It has been hypothesized that the lack of neurotrophic factors is responsible for the degeneration of selective neuronal populations as it occurs in Parkinson's disease, Alzheimer's disease and amyotrophic lateral sclerosis.

In preferred embodiments of the present invention, one or more of these activities of proneurotrophin(s) are inhibited directly or indirectly by the administration of an agent to an animal.

The terms inhibition or inhibited refer to any decrease in the biological activity of a bioactive agent, for example a proneurotrophin. In one embodiment of the present invention, such an inhibition refer to a decrease in the binding of a proneurotrophin to a Vps10p-domain receptor, especially the binding of a pro-NGF or a pro-BDNF to a Sortilin receptor. The efficiency of inhibiting effect of agents of the present invention may be measured by competitive inhibitory experiments using BIAcore (surface plasmon resonance).

Agents Capable of Inhibiting Binding of a Proneurotrophin to a Vps10p-Domain Receptor In one preferred embodiment of the present invention, an agent is administered to the animal, said agent being capable of inhibiting the binding between a receptor of the Vps10p-domain receptor family and a proneurotrophin.

In another, equally preferred embodiment, the agent is capable of binding to a receptor of the Vps10p-domain receptor family and/or pro-neurotrophin thereby interfering with the activity of a proneurotrophin, either directly or indirectly.

The agent capable of exhibiting one or more of the above mentioned effects may be any type of agent, for example the agent may be selected from the group comprising proteins, peptides, polypeptides or organic molecules. In a preferred embodiment the agent is an antibody, a compound or a polypeptide, and the agent is most preferably a polypeptide or an organic molecule. Said agents may bind to either of the following sequences:

```
Sortilin:
RIFRSSDFAKNF    (Residues 120-131 of SEQ ID NO: 1)

SorLA:
YLWITFDFCNTL    (Residues 105-116 of SEQ ID NO: 2)

SorCS1:
SLLISSDEGATY    (Residues 254-265 of SEQ ID NO: 3)

SorCS2:
SLFLSADEGATF    (Residues 1-12 of SEQ ID NO: 44)

SorCS3:
SILISSDEGATY    (Residues 277-288 of SEQ ID NO: 5)
```

The invention inhibits binding of a pro-neurotrophin to the sequences above thus preventing the pro-neurotrophin:Vps1 Op-domain receptor binary complex from performing a biologically or physiologically relevant activity, thus the agents of the present invention may be used to prevent diseases and disorders as specified herein below.

In a particularly preferred embodiment of the present invention, the agent administered to the animal is capable of inhibiting the binding of a proneurotrophin to a sortilin receptor thus inhibiting the receptor activity, said activity may be, but is not restricted to, one or more of the following:

i) cellular sorting of the receptor
ii) receptor binding directly or indirectly by ligand bridging to other receptors, such as the p75 and Trk receptors
iii) sortilin receptor signalling In one embodiment of the present invention, the agent is capable of inhibiting binding of a pro-neurotrophin to a receptor of the Vps10p-domain receptor family. Such inhibition may for example be due to binding of the agent either to the pro-neurotrophin and/or the Vps10p-domain receptor such as the receptor Sortilin.

In one embodiment the agent is a fragment or a variant of the Vps10p-domain of the Sortilin receptor said fragment or variant capable of binding the pro-domain of a pro-neurotrophin or a fragment or a variant thereof. In particular the agent include but is not limited to the fragments FANKNFV, RIFR and RIFRSSDF as displayed in figure 17 describing the length analysis of pro-domain-BDNF binding to sortilin peptides. Any fragment or variant capable of binding to a pro-neurotrophin is included herein. In particular a fragment is a peptide comprising a sequence corresponding to any of SEQ ID NOs: 25 to 28. This domain is herein referred to as the pro-neurotrophin binding motif of the Vps10p domain. Peptides comprising the SEQ ID NOs: 25 to 28 may be at least 3 residues long, such as 5 residues long, such as 7 residues long, such as 10 residues long, such as 13 residues long, such as 15 residues long, such as 20 residues long, such as 25 residues long, such as 30 residues long, such as 35 residues long, such as 40 residues long, such as 50 residues long, such as 60 residues long, such as 70 residues long, such as 80 residues long, such as at least 90 residues long, such as 100 residues long, such as 125 residues long such as 150 residues long, such as 175 residues long such as 200 residues long. The sequences within such a peptide identical to SEQ ID NO:25 may lie in the beginning of said peptide, the end, the middle or anywhere in between. Said peptides may furthermore be variants of the original SEQ ID NO:1 sequence, variants as defined in the above. Preferably the variant comprise conservative amino acid substitutions or other, benign alterations to the original sequence. A preferred peptide according to the present invention comprises SEQ ID NO: 26 and fragments and variants hereof, such as the sequences identified in SEQ ID NO: 27 and/or SEQ ID NO: 28 and fragments and variant of these. Examples of variants are also given in FIGS. 15 and 16, in which a sequence falling within SEQ ID NO: 25 is the subject of a substitution analysis. Herein it is confirmed that the especially relevant parts of the present binding motif of the Vps10p domain falls within the sequence described in SEQ ID NO: 26, and the most essential parts hereof again are the sequences identified in SEQ ID NO: 27 and SEQ ID NO: 28. Regarding either of SEQ ID NO: 1, 25, 26, 27 or 28, FIGS. 15 and 16 indicates that e.g. R196 as counted using pre-pro-Sortilin (corresponds to R163 for proSortilin) may in a manner conserving the ability to bind BDNF be substituted with either F, G, H, I, L, N, P, Q, T, V, W or Y, and preferably is substituted with either F, H, I, L, V, W or Y. Likewise any of the other residues of SEQ ID NO: 1, 25, 26, 27 or 28 may be substituted. 1197 as counted using pre-pro-Sortilin (corresponds to 1164 for proSortilin) is thus preferably substituted with A, F, G, H, P, R, S, T, V or Y; F198 as counted using pre-pro-Sortilin (corresponds to F165 for proSortilin) is preferably substituted with I, L, R, or W; R199 as counted using pre-pro-Sortilin (corresponds to R166 for proSortilin) is preferably substituted with A, D, F, G, H, I, L, S, T, V, W or Y; F203 as counted using pre-pro-Sortilin (corresponds to F170 for proSortilin) is preferably substituted with L, P or R; A204 as counted using pre-pro-Sortilin (corresponds to A171 for proSortilin) is preferably substituted with D, E, G, H, I, K, L, M, N, P, Q, R, S, T, V, W or Y; K205 as counted using pre-pro-Sortilin (corresponds to K172 for proSortilin) is preferably substituted with A, F, G, H, I, L, M, N, P, Q, R, S, T, V, W or Y; $N_2O6$ as counted using pre-pro-Sortilin (corresponds to N173 for proSortilin) is preferably substituted with A, F, G, H, I, K, L, M, P, Q, R, S, T, or V; and F207 as counted using pre-pro-Sortilin (corresponds to F174 for proSortilin) is preferably substituted with H, I, K, L, N, P, Q, R, or V. Any of these substitutions may be made alone or in combination with any of the other preferred substitutions or any of the other methods of generating variants as mentioned herein.

In another embodiment the agent is capable of binding to the receptor. The agent may bind to any part of the receptor relevant for inhibiting the binding of the neurotrophin. Accordingly, the agent may be capable of inhibiting the binding of said neurotrophin or said pro-neurotrophin to a receptor of the Vps10p-domain receptor family by binding to an intracellular part of the receptor.

An object of the invention is to provide agents that alone or assisted by a pharmaceutical agent/formulation are capable of crossing the blood/brain barrier.

An example of an agent according to the invention is an antibody directed against an extra-cellular part of the receptor. In an even more preferred embodiment, the antibody is purified. In the preferred embodiment wherein the agent is an antibody directed against an extra-cellular part of the receptor, the antibody is preferably directed against a peptide comprising a sequence corresponding to the binding motif of the Vps10p domain, said motif comprising SEQ ID NO: 25, 26, 27 or 28 or a fragment or variant hereof. Said fragment may comprise between 3 and 31 amino residues, such as between 3 and 29 amino acid residues, for example between 3 and 27 amino acid residues, such as between 3 and 25 amino acid residues, for example between 3 and 23 amino acid residues, such as between 3 and 21 amino acid residues, for example between 3 and 19 amino acid residues, such as between 3 and 17 amino acid residues, for example between 3 and 15 amino acid residues, such as between 3 and 13 amino acid residues, for example between 3 and 11 amino acid residues, such as between 3 and 9 amino acid residues, for example between 3 and 7 amino acid residues, such as between 3 and 5 amino acid residues, for example 4 amino acid residues, such as between 5 and 31 amino acid residues, for example between 7 and 31 amino acid residues, such as between 9 and 31 amino acid residues, for example between 11 and 31 amino acid residues, such as between 13 and 31 amino acid residues, for example between 15 and 31 amino acid residues, such as between 17 and 31 amino acid residues, for example between 19 and 31 amino acid residues, such as between 21 and 31 amino acid residues, for example between 23 and 31 amino acid residues, such as between 25 and 31 amino acid residues, for example between 27 and 31 amino acid residues, such as between 29 and 31 amino acid residues, for example 30 amino acid residues.

In particular the antibody should be directed against a position in this motif so that the antibody sterically blocks the binding of the pro-neurotrophin to the receptor.

In yet another embodiment, compounds of the present invention, thus capable of acting as inhibitors of proneurotrophins to Vps10p domain receptors, comprises polypeptides of between 1 and 500 amino acid residues comprising one or more of the SEQ ID NO:s 25, 26, 27 and 28.

In yet another embodiment the agent is a neurotensin analog and/or a neurotensin system modulator including, but not limited to SEQ ID NO. 24 and SEQ ID NOs. 29 to 42. Neurotensin and the neurotensin system modulators bind to Vps10-p domain receptors for example the Sortilin receptor or fragments thereof such as and not limited to the sequences displayed in FIG. 17, thus preventing any normal and/or natural ligand from binding to Sortilin hence acting as antagonists to the neurotrophins that otherwise would interact with Sortilin and herein disclosed fragments thereof. Furthermore, said neurotensin and neurotensin system modulators may bind to an alternate binding site of the Sortilin receptor inducing conformational changes affecting the binding affinity between neurotrophins and Sortilin in an antagonistic manner. Said neurotensin and neurotensin system modulators are preferably capable of crossing the blood-brain barrier and of the Vps10p-domain receptors preferably bind to Sortilin. In yet a preferred embodiment, neurotensin and the neurotensin system modulators do not have any significant binding affinity towards or adverse effects upon bind to other Vps10p-domin receptors or indeed other receptors than Sortilin.

Vps10p-domain receptors, especially Sortilin, initially identified as neurotensin receptor 3 (NTR-3) have partial overlapping substrate specificity with neurotensin receptors 1 and 2 (NTR-1 and NTR-2) both which bind NT(1-13) with high affinity. In addition a number of neurotensin system modulators are known ligands of NTR-1 and NTR-2. Examples hereof are the peptides NT66L (SEQ ID NO. 15), NT67L (SEQ ID NO. 16), NT69L (SEQ ID NO. 17), Eisai (SEQ ID NO. 18), JMV-449 (SEQ ID NO. 19), PD-149163 (SEQ ID NO. 20), PD-149598 (SEQ ID NO. 21), PD-156425 of the structure:

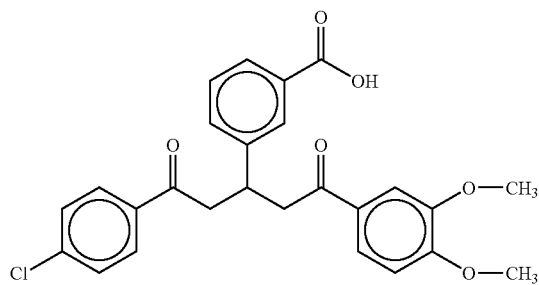

and PD-156556 (SEQ ID NO. 23), CGX-1160 (SEQ ID NO. 24), PD-147113 (SEQ ID NO 29), GZR-123 (SEQ ID NO 30), NT64D (SEQ ID NO. 31), NT64L (SEQ ID NO. 32), NT65L (SEQ ID NO. 33), NT66D (SEQ ID NO. 34), NT69L' (SEQ ID NO. 35), NT71 (SEQ ID NO. 36), NT72 (SEQ ID NO. 37), NT73 (SEQ ID NO. 38), NT74 (SEQ ID NO. 39), NT75 (SEQ ID NO. 40), NT76 (SEQ ID NO. 41), NT77 (SEQ ID NO. 42) and the compounds SR-142948A, SR-48692, UK-73093 and L-737631. All of these compounds and peptides are agents according to the present invention. Furthermore, derivates of the above compounds and variant or fragments or peptides comprising the abovementioned peptides are agents according to the present invention. By derivates are understood compounds retaining a substantial and/or significant part of the structure of the mentioned compounds but substituted differently, i.e. comprising other substituents. Derivates may also be molecules that are capable of interacting in the same manner as the parent compound, i.e. interact with the same residues on the Vps10p-domain receptor. Examples of such substituents comprise and are not limited to: Alicyclic groups: the term "alicyclic group" means a cyclic hydrocarbon group having properties resembling those of aliphatic groups. Aliphatic groups: in the context of the present invention, the term "aliphatic group" means a saturated or unsaturated linear or branched hydrocarbon group. This term is used to encompass alkyl, alkenyl, and alkynyl groups, for example. Alkyl groups: the term "alkyl group" means a saturated linear or branched hydrocarbon group including, for example, methyl, ethyl, isopropyl, t-butyl, heptyl, dodecyl, octadecyl, amyl, 2-ethylhexyl, and the like. Alkenyl groups: the term "alkenyl group" means an unsaturated, linear or branched hydrocarbon group with one or more carbon-carbon double bonds, such as a vinyl group. Alkynyl groups: the term "alkynyl group" means an unsaturated, linear or branched hydrocarbon group with one or more carbon-carbon triple bonds; Amphiphils: substance containing both polar, water-soluble and nonpolar, water-insoluble groups. Aromatic group: the term "aromatic group" or "aryl group" means a mono- or poly-cyclic aromatic hydrocarbon group. Cyclic groups: the term "cyclic group" means a closed ring hydrocarbon group that is classified as an alicyclic group, aromatic group, or heterocyclic group. Cycloalkenyls: means a monovalent unsaturated carbocyclic radical consisting of one, two or three rings, of three to eight carbons per ring, which can optionally be substituted with one or two substituents selected from the group consisting of hydroxy, cyano, lower alkenyl, lower alkoxy, lower haloalkoxy, alkenylthio, halo, haloalkenyl, hydroxyalkenyl, nitro, alkoxycarbonenyl, amino, alkenylamino, alkenylsulfonyl, arylsulfonyl, alkenylaminosulfonyl, arylaminosulfonyl, alkylsulfonylamino, arylsulfonylamino, alkenylaminocarbonyl, arylaminocarbonyl, alkenylcarbonylamino and arylcarbonylamino. Cycloalkyls: meaning a monovalent saturated carbocyclic radical consisting of one, two or three rings, of three to eight carbons per ring, which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino and arylcarbonylamino.

Cationic groups: A chemical group capable of functioning as a proton donor when a compound comprising the chemical group is dissolved in a solvent, preferably when dissolved in water. Generally a "Group"/Moiety/substitute is well understood in this technical area, and a large degree of substitution is not only tolerated, but is often advisable. Substitution is anticipated on the materials of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl groups or other conventional substitution. Where the term "moiety" is used to de-scribe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like. The same definitions apply to "alkenyl group" and "alkenyl moiety"; to "alkynyl group" and "alkynyl moiety"; to "cyclic group" and "cyclic moiety; to "alicyclic group" and "alicyclic moiety"; to "aromatic group" or "aryl group" and to "aromatic moiety" or "aryl moiety"; as well as to "heterocyclic group" and "heterocyclic moiety". Heterocyclic group: the term "heterocyclic group" means a closed ring hydrocarbon in which one or more of the atoms in the ring is an element other than carbon (e.g., nitrogen, oxygen, sulphur, etc.). Heterocyclyl means a monovalent saturated cyclic radical, consisting of one to two rings, of three to eight atoms per ring, incorporating one or two ring heteroatoms (chosen from N, O or S(O)0-2, and which can optionally be substituted with one or two substituents selected from the group consisting of hydroxyl, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, or arylcarbonylamino. Heteroaryl means a monovalent aromatic cyclic radical having one to three rings, of four to eight atoms per ring, incorporating one or two heteroatoms (chosen from nitrogen, oxygen, or sulphur) within the ring which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino and arylcarbonylamino. Substituted lower alkyl means a lower alkyl having one to three substituents selected from the group consisting of hydroxyl, alkoxy, amino, amido, carboxyl, acyl, halogen, cyano, nitro and thiol. Variants, fragments or peptides comprising the neurotensin system modulator peptides may be generated by conservative amino acid substitution as defined in the above or by the inclusion, and/or substitution of any of the residues for any naturally occurring L-, D- or amino acid or any synthetic amino acid derivative. Furthermore, the bonds between the residues in mentioned amino acids may be altered forming non-amide bond linked amino acid peptides.

Thus in an embodiment of the present invention neurotensin system modulators as defined in any of SEQ ID NOs. 10-11, 13-24, 29-42 and derivates or variants hereof and the compounds SR-142948A, SR-48692, UK-73093 and L-737631 and derivates or variants hereof are agents of the present invention. Furthermore, fragments of the peptides are also agents of the present invention. These fragments may be one or more amino acids shorter than the peptides according to the SEQ ID NO's listed above. It is of importance that the peptides that interact with Sortilin are retained in these fragments. Preferred agents are SR-48692, NT-69L and CGX-1160 and/or variants hereof.

In another preferred embodiment of the present invention, the agent is capable of binding to an intracellular part of the receptor and/or the transmembrane part of a receptor of the Vps10p domain receptor family. In particular the agent may be capable of binding to the cytoplasmic part of the receptor of the Vps10p domain receptor family, such as to a part of Sortilin corresponding to SEQ ID NO: 1 or a fragment thereof comprising any of SEQ ID NOs: 25 to 28.

In particular binding of an agent to the intracellular and transmembrane parts of the receptor may lead to modulation of the proneurotrophin activity through a modulation of the transport of at least one pro-neurotrophin out of, into or within cells expressing the receptor of the Vps10p domain receptor family as discussed below.

In another preferred embodiment, the agent is capable of modulating the expression of a receptor of the Vps10p-domain receptor family and thereby interfering with the activity of at least one proneurotrophin. The modulation may be either inhibition or stimulation of the expression. Preferable methods for modulating the expression of the receptor include, but are not restricted to:

(i) Blocking or inhibiting the activity of the translation products of one or more Vps10p-domain receptor genes and/or one or more derivatives thereof, by inhibiting mRNA translation or transcriptional activation using antisense nucleic acids.
(ii) Inactivating mRNA by ribozymes targeted to the mRNAs encoding one or more Vps10p-domain receptor genes and/or one or more derivatives thereof.
(iii) Inhibition of the intracellularly present translation products of the Vps10p-domain receptor genes by administering molecules which mimic targets of the translation products of one or more Vps10p-domain receptor genes and/or one or more derivatives thereof thereby competing with their natural targets.
(iv) Stimulating the expression of one or more Vps10p-domain receptor genes and/or one or more derivatives thereof, for example in one preferred embodiment, an agent is administered to cells in vitro or in vivo. Such an agent may act either specifically or non-specifically. It is also possible to activate genes responsible for further growth of differentiated tissue by introducing one or more Vps10p-domain receptor genes and/or one or more derivatives thereof into the respective cells and tissue by means of gene therapy. For this purpose the respective nucleic acid sequences may be put under control of a strong promoter, which optionally can be activated and deactivated upon administration of a stimulus to the cell/tissue.
(v) Stimulating expression of one or more Vps10p-domain receptor genes and/or one or more derivatives thereof by administering directly to the respective cell/tissue a translation product, either a peptide or a protein, that is derived from one or more Vps10p-domain receptor gene and/or one or more derivative thereof. Due to the low molecular weight of any of the aforementioned translation products these peptides/proteins can easily be applied to the cell, for example using encapsulation delivery systems.

The change in expression level of the receptor of the Vps10p-domain receptor family may be assayed for using methods known to those skilled in the art, including but not restricted to: DNA arrays or microarrays (Brazma and Vilo, FEBS Lett., 2000, 480, 17-24; Celis, et al., FEBS Lett., 2000, 480, 2-16), SAGE (serial analysis of gene expression)(Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (reviewed in (To, Comb. Chem. High Throughput Screen, 2000, 3, 235-41).

Methods for Treating a Disease or Disorder

In one preferred embodiment of the present invention, the invention comprises a method for treating a disease or disorder in an individual. Said method comprises administering to said individual, in a pharmaceutically acceptable carrier, a sufficient amount of an agent capable of interfering with binding between a receptor of the Vps10p-domain receptor family and a proneurotrophin. By "sufficient amount" herein is meant a dose that produces the therapeutic effects for which it is administered. The exact dose will depend on the disorder to be treated, and will be ascertainable by one skilled in the art using known techniques. In general, the agent of the present invention is administered to an animal in an amount of from 1 µg/kg to about 100 mg/kg per day. In addition, as is known in the art, adjustments for age as well as the body weight, general health, sex, diet, time of administration, drug interaction and the severity of the disease may be necessary, and will be ascertainable with routine experimentation by those skilled in the art.

Agents of the present invention are believed to be useful in promoting the development, maintenance, or regeneration of neurons in vitro and in vivo, including central (brain and spinal chord), peripheral (sympathetic, parasympathetic, sensory, and enteric neurons), and motor neurons. Accordingly, agents of the present invention may be utilized in methods for the treatment of a variety, of neurological diseases, disorders and degeneration. In a preferred embodiment, the formulations of the present invention are administered to a patient to treat neural disorders. By "neural disorders" herein is meant disorders of the central and/or peripheral nervous system that are associated with neuron degeneration or damage. Specific examples of neural disorders include, but are not limited to, Alzheimer's disease, Parkinson's disease, Huntington's chorea, stroke, ALS, peripheral neuropathies, and other conditions characterized by necrosis or loss of neurons, whether central, peripheral, or motor neurons, in addition to treating damaged nerves due to trauma, burns, kidney dysfunction or injury, pancreatic dysfunction or injury, lung dysfunction or injury, injury to fatty tissue, and the toxic effects of chemotherapeutics used to treat cancer and AIDS. For example, peripheral neuropathies associated with certain conditions, such as neuropathies associated with diabetes, AIDS, or chemotherapy may be treated using the formulations of the present invention.

In various embodiments of the invention, agents are administered to patients in whom the nervous system has been damaged by trauma, surgery, stroke, ischemia, infection, metabolic disease, nutritional deficiency, malignancy, or toxic agents, to promote the survival or growth of neurons, or in whatever conditions are treatable with NGF, NT-3, BDNF or NT4-5. For example, agents of the invention can be used to promote the survival or growth of motor neurons that are damaged by trauma or surgery. Also, agents of the invention can be used to treat motor neuron disorders, such as amyotrophic lateral sclerosis (Lou Gehrig's disease), Bell's palsy, and various conditions involving spinal muscular atrophy, or paralysis. Agents of the present invention can be used to treat human neurodegenerative disorders, such as Alzheimer's disease, Parkinson's disease, epilepsy, multiple sclerosis, Huntington's chorea, Down's Syndrome, nerve deafness, and Meniere's disease.

Neurotrophins are essential for the health and well-being of the nervous system. For example NGF (nerve growth factor), BDNF (brain-derived neurotrophic factor), NT-3 (neurotrophin-3) and NT-4 (neurotrophin-4) also mediate additional higher-order activities, such as learning, memory and behaviour, in addition to their established functions for cell survival. Agents of the present invention can thus be used as cognitive enhancers, to enhance learning, particularly in patients suffering from dementias or trauma. Alzheimer's disease, which has been identified by the National Institutes of Aging as accounting for more than 50% of dementia in the elderly, is also the fourth or fifth leading cause of death in Americans over 65 years of age. Four million Americans, 40% of Americans over age 85 (the fastest growing segment of the U.S. population), have Alzheimer's disease. Twenty-five percent of all patients with Parkinson's disease also suffer from Alzheimer's disease-like dementia. And in about 15% of patients with dementia, Alzheimer's disease and multi-infarct dementia coexist. The third most common cause of dementia, after Alzheimer's disease and vascular dementia, is cognitive impairment due to organic brain disease related directly to alcoholism, which occurs in about 10% of alcoholics. However, the most consistent abnormality for Alzheimer's disease, as well as for vascular dementia and cognitive impairment due to organic brain disease related to alcoholism, is the degeneration of the cholinergic system arising from the basal forebrain (BF) to both the codex and hippocampus (Bigl et al. in Brain Cholinergic Systems, M. Steriade and D. Biesold, eds., Oxford University Press, Oxford, pp. 364-386 (1990)). And there are a number of other neurotransmitter systems affected by Alzheimer's disease (Davies Med. Res. Rev. 3:221 (1983)). However, cognitive impairment, related for example to degeneration of the cholinergic neurotransmitter system, is not limited to individuals suffering from dementia. It has also been seen in otherwise healthy aged adults and rats. Studies that compare the degree of learning impairment with the degree of reduced cortical cerebral blood flow in aged rats show a good correlation (Berman et al. Neurobiol. Aging 9:691 (1988)). In chronic alcoholism the resultant organic brain disease, like Alzheimer's disease and normal aging, is also characterized by diffuse reductions in cortical cerebral blood flow in those brain regions where cholinergic neurons arise (basal forebrain) and to which they project (cerebral cortex) (Lofti et al., Cerebrovasc and Brain Metab. Rev 1:2 (1989)). Such dementias can be treated by administration of agents of the present invention.

It is an object of the present invention to use the agents hereof to treat multiple sclerosis. The agents of the present invention may be used alone or in combination with other medicaments. Examples of such compounds include and are not limited to: Interferon beta (e.g. beta-1a and/or beta-1b), glatiramer acetate (Copaxone, a mixture of polypeptides which may protect important myelin proteins by substituting itself as the target of immune system attack), mitoxantrone and natalizumab (Tysabri), corticosteroids, and monoclonal antibodies.

In addition, agents of the present invention may be used in the treatment of spinal cord injuries and/or in combination with other treatment applied after spinal cord injuries. Current examples of such agents include and are not limited to the steroid drug methylprednisolone given within the first 8 hours after injury to reduce the damage to nerve cells.

Moreover, agents of the present invention may be used in the treatment of Parkinson's disease (PD) and or in combination with other medicaments given in the treatment of Parkinson's disease; such agents include and are not limited to: levodopa, carbidopa, benserazide, talcopone, entacapone, mucuna pruriens, dopamine agonists such as bromocriptine, pergolide, pramipexole, ropinirole, cabergoline, apomorphine, and lisuride, MAO-B inhibitors such as selegiline and rasagiline. In addition other non-pharmacological treatments such as surgical interventions, speech therapy and physical exercise has proven to be moderately effective and agent of the present invention may be used in combination with these methods of therapy as well. Furthermore, the agents of the present invention may be used in combination with methods employing gene and/or cellular therapy, such as the implantation of cells genetically engineered to produce dopamine or stem cells that transform into dopamine-producing cells or the agents may be used in combination with GDNF (glial-derived neurotrophic factor) infusion. This involves the infusion of GDNF into the basal ganglia using surgically implanted catheters. Also, treatment with neuroprotective agents such as apoptotic drugs (CEP 1347 and CTCT346), lazaroids, bioenergetics and/or antiglutamatergic agents in combination with the agents described herein above fall within the scope of the present invention.

In yet another embodiment, agents of the current invention may be used in the treatment of stroke. Furthermore, agents of the present invention may be used in combination with medicaments used in the treatment of stroke such as antiplatelet medication (e.g. aspirin, clopidogrel and dipyridamole) or anticoagulant medication such as warfarin or the tissue plasminogen activator, tPA. The method of clearing the blocked blood vessel by mechanical thrombectomy may also be used in combination with agents of the present invention.

Further, agents of the present invention are preferably used to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include, but are not limited to, diabetic peripheral neuropathy, distal sensorimotor neuropathy, or autonomic neuropathies such as reduced motility of the gastrointestinal tract or atony of the urinary bladder. Examples of neuropathies associated with systemic disease include post-polio syndrome or AIDS-associated neuropathy; examples of hereditary neuropathies include Charcot-Marie-Tooth disease, Refsum's disease, Abetalipoproteinemia, Tangier disease, Krabbe's disease, Metachromatic leukodystrophy, Down's Syndrome, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine.

Furthermore, neuronal degeneration as seen in aging or senescence is an object of the present invention. Senescence is the combination of processes of deterioration which follow the period of development of an organism and is generally characterized by the declining ability to respond to stress, increasing homeostatic imbalance and increased risk of disease. Aging itself is by some gerontologists considered a "disease" that may be curable. In accordance with this view aging is an accumulation of damage to macromolecules, cells, tissues and organs, thus advanced biochemical and molecular repair technologies may be able to counter the damage caused by senescence. Agents of the present invention may be utilized in methods for the protection and or prevention of damage induced by senescence, especially neuronal degeneration due to senescence. In a preferred embodiment, the formulations of the present invention are administered to a patient to treat senescence related neuronal degeneration.

It is within the scope of the present invention to provide agent for the treatment, prevention and/or amelioration of neuropsychiatric disorders. Certain of the below mentioned conditions may also be referred to as neural diseases. Neuropsychiatric diseases and disorder may be divided onto three main groups: thought/psychotic disorders (these make it hard for people to separate what is real from what is not, e.g. schizophrenia), mood disorders (affect how a person feels; for example, very sad or hopeless. If a mood disorder becomes severe, it can appear to be a thought disorder, e.g. bipolar disorder and depressive disorders), anxiety disorders (make a person feel overwhelmingly anxious and fearful, e.g. Panic disorder and obsessive-compulsive disorder (OCD)). Examples of neuropsychiatric disorders include any neuropsychiatric disease or disorder such as, but not limited to: schizophrenia, bipolar disorder, depression, mania, substance dependence and abuse (e.g. alcohol dependence), depression, bipolar disorder, Alzheimer's disease, Parkinson's disease, psychotic disorders, schizophrenia, schizoaffective disorder, anxiety disorders, post-traumatic stress disorder, obsessive-compulsive disorder, borderline personality disorder, schizotypal personality disorder, avoidant personality disorder and antisocial personality disorder. The pathogenesis of schizophrenia may be ascribed to early maldevelopment of brain tissue. Accumulating preclinical and clinical data indicate that dysfunctions of neurotrophins, especially nerve growth factor (NGF), brain derived neurotrophic factor (BDNF) and neurotrophin-3 (NT-3) may contribute to impaired brain development, neuroplasticity and synaptic "dysconnectivity" leading to the schizophrenic syndrome. Furthermore there are several lines of evidence supporting a role for neurotrophins and proneurotrophins in the treatment of depression, chronic stress and substance abuse. An enhancement in neurotrophic support and associated augmentation in synaptic plasticity and function may form the basis for antidepressant efficacy. Thus neuropsychiatric diseases and disorders such as schizophrenia, depression, chronic stress, and substance abuse are objects of the present invention and may be treated, prevented or ameliorated by administration of the agents herein described.

Other disorders, diseases and degenerative conditions in a mammal that may be treated by a therapeutically effective amount of one or more agents of the present invention are diseases, disorders and degenerations of the eye. The conditions of this type that are of special interest to the present invention may be divided in to four categories: Acquired macular diseases (AMD), Retinal vascular diseases, Retina detachment, and hereditary fundus dystrophies. Preferably, the disorders are Acquired macular diseases such as exodative and non-exodative age-related macular degeneration, Retinal vascular diseases such as diabetic retinoplasy and blood clots in the eye, and hereditary fundus dystrophies such as lebers. Other disorders specifically relate to senescence of the eye that in accordance with most anatomical and physiological processes follow a gradual decline. Agents of the present invention are useful in preventing or improving pathological conditions of the eye.

In addition, pain and nociception are indications of relevance for the agents of the present invention. Pain is, and nociception may be, an unpleasant sensation, ranging in intensity from slight through severe to indescribable. Where pain is a subjective feeling, nociception is a measurable physiological event that may occur without pain being felt. Physiological pain can be classified according to source and its related pain detecting neurons (nociceptors) into cutaneous pain, somatic pain, viscera) pain, phantom limb pain and neuropathic pain. Cutaneous pain is caused by injury to the skin or superficial tissues. Somatic pain originates from ligaments, tendons, bones, blood vessels, and even nerves themselves. Visceral pain originates from body's viscera, or organs. Phantom limb pain is the sensation of pain from a limb that has been lost or from which a person no longer receives physical signals. Neuropathic pain, or "neuralgia", can occur as a result of injury or disease to the nerve tissue itself.

Pain and/or nociceptions may arise due to different causes, a main cause being trauma. Trauma may occur too any body part, and any trauma that causes pain or nociception is within the scope of the present invention. Other examples of pain and nociceptions include but are not limited to: Head and neck related: Jaw—Temporal arteritis (serious); Ear—otitis media (very common esp. in children), otitis externa; Eye—glaucoma; Head—migraine, tension headache, cluster headache, cancer, cerebral aneurysm, sinusitis, meningitis, Neck pain—MI (atypical); Thorax: Back—cancer; Breast—perimenstrual, cancer; Chest—MI (common and fatal), GERD (very common), pancreatitis, hiatal hernia, aortic dissection (rare), pulmonary embolism (more frequently asymptomatic), Costochondritis, Shoulder—cholecystitis (right side), MSK; Abdomen: Adominal—Left and right upper quadrant—peptic ulcer disease, gastroenteritis, hepatitis, pancreatitis, cholecystitis, MI (atypical), abdominal aortic aneurysm, gastric cancer, Left and right lower quadrant—appendicitis (serious), ectopic pregnancy (serious/women only), pelvic inflammatory disease (women only), diverticulitis (common in old), urolithiasis (kidney stone), pyelonephritis, cancer (colorectal cancer most common); Back: Back—MSK (muscle strain), cancer, spinal disc herniation, degenerative disc disease, coccyx (coccydynia); Limbs: Arm—MI (classically left, sometimes bilateral), MSK; Leg—deep vein thrombosis, peripheral vascular disease (claudication), MSK, spinal disc herniation, sciatica; Joints: Classically small joints—osteoarthritis (common in old), rheumatoid arthritis, systemic lupus erythematosis, gout, pseudogout; Classically large joints (hip, knee)—osteoarthritis (common in old), septic arthritis, hemarthrosis; Classically back—ankylosing spondylitis, inflammatory bowel disease; Other—psoriatic arthritis, Reiter's syndrome. Agents of the present invention may be used as analgesics or analgetic agents to treat and/or ameliorate any of the above types of pain and/or nociceptions.

Moreover, obesity is an indication of relevance for the agents of the present invention. Obesity is a condition in which the natural energy reserve, stored in the adipose tissue of humans and other mammals, is increased to a point where it is a risk factor for certain health conditions or increased mortality. Excessive body weight has been shown to predispose to various diseases, particularly cardiovascular diseases, sleep apnea, osteoarthritis and non-insulin-dependent diabetes mellitus. Obesity is the single most frequent contributor of type 2 diabetes. Type 2 diabetes is a metabolic disorder that is caused by insulin resistance and relative insulin deficiency, and chronic hyperglycemia. It is rapidly increasing in the world and it is estimated to increase according to epidemic trends. A Vps10p domain receptor gene has recently been associated with type 2 diabetes in mouse and rat. Other types of diabetes are also within the scope of the present invention, these are diabetes type 1 and gestational diabetes (GDM) occurring during pregnancy and other types. Type 1 is due to autoimmune destruction of the insulin-producing cells. It is an object of the present invention to provide agents for the treatment of obesity, diabetes type 1, 2, GDM and diabetes related disorders. In addition to diabetes, obesity also enhances the risk of myocardial infarction due to atherosclerosis which is an objective for agents of the present invention.

Accordingly, a method of treating, preventing and/or ameliorating a proneurotrophin related disorder, disease or degeneration in a mammal comprising administering to the mammal a therapeutically effective amount of one or more agents of the present invention is provided. These proneurotrophin related diseases, disorders or degenerative conditions may be any of the conditions of the above such as neuronal disorders, neuronal degeneration, neuropsychiatric disorders and diseases, senescence, pain and nociception, ocular diseases, disorders or degeneration, obesity and obesity related diseases and diabetes. Pain as used herein above refer to peripheral pain. Ocular diseases as used herin refer to retinal diseases, disorders and degeneration of the retina.

It is an object of the present invention that any of the herein described agents may be used alone or in combination with one another. The agents of the present invention may thus be administered simultaneously or in succession. The agent may furthermore alone or in combination be used together with a second active ingredient. These second active ingredients may be for the treatment of any of the herein mentioned diseases or disorders, or may be used for other purposes.

Another embodiment of the present invention comprises a kit of parts, wherein the kit includes at least one agent or pharmaceutical composition as described herein, a means for administering said vaccine and the instruction on how to do so. It is within the scope of the present invention to include multiple dosages of the same agent and/or pharmaceutical composition or several different agent and/or pharmaceutical compositions. In a preferred embodiment the kit of parts further comprises a second active ingredient.

Methods of Administration

Agents used in the methods of the present invention are generally administered to an animal in the form of a suitable pharmaceutical composition. Accordingly, the present invention also relates to a pharmaceutical composition comprising an agent as defined herein. Such compositions typically contain the agent and a pharmaceutically acceptable carrier. As used herein the language "pharmaceutically acceptable carrier" is intended to include any and all solvents, dispersion media, coatings, anti-bacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the agent, use thereof in the compositions is contemplated. Supplementary active compounds can also be incorporated into the compositions.

A pharmaceutical composition of the invention is formulated to be compatible with its intended route of administration. Examples of suitable routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™

(BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the agent in the required amount in an appropriate solvent with one or a combination of ingredients enumerated above, as required, followed by filtered sterilization. Generally, dispersions are prepared by incorporating the agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatine capsules or compressed into tablets. For the purpose of oral therapeutic administration, the agent can be incorporated with excipients and used in the form of tablets, troches, or capsules, oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, or orange flavouring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agent can also be prepared in the form of suppositories (e.g., with conventional suppository bases such as cocoa butter and other glycerides) or retention enemas for rectal delivery.

In one embodiment, the agent is prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents that exhibit large therapeutic indices are preferred. While agents that exhibit toxic side effects may be used, care should be taken to design a delivery system that targets such agents to the site of affected tissue in order to minimize potential damage to other cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test agent which achieves a half-maximal inhibition of symptoms) as determined in cell culture. Such information can be used to more accurately determine useful doses in humans. Levels in plasma may be measured, for example, by high performance liquid chromatography. With respect to inhibition of Sortilin 10-20 µmol of Neurotensin is used to inhibit Sortilin in a cell culture.

The pharmaceutical compositions can be included in a container, pack, or dispenser together with instructions for administration.

The agents of the present invention can further be inserted into vectors and used in gene therapy. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Vectors suitable for use in gene therapy are known in the art. For example, adenovirus-derived vectors can be used. The genome of an adenovirus can be manipulated such that it encodes and expresses a gene product of interest but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267). Most replication-defective adenoviral vectors currently in use and therefore favoured by the present invention are deleted for all or parts of the viral E1 and E3 genes but retain as much as 80% of the adenoviral genetic material (see, e.g., Jones et al. (1979) Cell 16:683; Berkner et al., supra; and Graham et al. in Methods in Molecular Biology, E. J. Murray, Ed. (Humana, Clifton, N.J., 1991) vol. 7, pp. 109-127). Expression of the gene of interest comprised in the nucleic acid molecule can be under control of, for example, the E1A promoter, the major late promoter (MLP) and associated leader sequences, the E3 promoter, or exogenously added promoter sequences.

Yet another viral vector system useful for delivery of the agents of the invention is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97-129). Adeno-associated viruses exhibit a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). Vectors containing as few as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into T cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790). Other viral vector systems that may be useful for delivery of the agents of the invention are derived from herpes virus, vaccinia virus, and several RNA viruses.

It should be understood that such treatments may also comprise administration of more than one agent, in which case the agents may be either administered concurrently and/or separately.

Animals

In one embodiment of the present invention, agents capable of inhibiting binding between a pro-neurotrophin and a Vps10p-domain receptor are administered to an animal. Said animal is preferably any animal that expresses a protein of the proneurotrophin family, more preferably a mammal, more preferably a domestic animal and most preferably a human being.

Methods for Screening for a Compound which Alters the Binding of at Least One Pro-Neurotrophin to a Receptor of the Vps10p-Domain Receptor Family In one preferred embodiment of the present invention, the invention comprises an in vitro method for screening for a compound which alters the binding of at least one pro-neurotrophin to a receptor of the Vps10p-domain receptor family, said method preferably comprising the steps of:
a) providing an assay for measuring the binding of a pro-neurotrophin to the binding site of the receptor Sortilin comprising SEQ ID NO. 25 or any variant or fragment thereof (including SEQ ID NOs: 26 to 28,
b) adding the compound to be tested to the assay, and
c) determining the amount of a pro-neurotrophin bound to the receptor of the Vps10p-domain receptor family, and
d) comparing the amount determined in step c) with an amount measured in the absence of the compound to be tested,
e) wherein a difference in the two amounts identifies a compound which alters the binding of pro-neurotrophins to the receptor of the Vps10p-domain receptor family.

In one preferred embodiment of this screening method of the present invention, the pro-neurotrophin may be selected from pro-NGF, pro-BDNF, pro-NT-3 or pro-NT-4/5. More preferably, the pro-neurotrophin is pro-NGF or pro-BDNF. In one preferred embodiment of this screening method, the receptor is selected from SorLA, Sortilin, SorCS1, SorCS3, or SorCS2. Even more preferably, the receptor is Sortilin. In another embodiment of the screening method of the present invention, the proneurotrophin is capable of binding to an extracellular part of the receptor. The receptor may in one embodiment of the present invention be a receptor that is expressed in a cell, within the plasma membrane and/or presented on a plasma membrane. The cell used in the screening method of the present invention may preferably be selected from primary cultures of neuronal cells, neurone-derived cell-lines, trans-fected cells capable of expressing receptor of the Vps10p-domain receptor family, peripheral neurons and central neurons. Preferably the cells are immortalised cell lines.

Assays that can be used for measuring the binding of a pro-neurotrophin to a receptor of the Vps10p-domain receptor family are well-known to those skilled in the art and include, but are not restricted to, yeast two-hybrid assays, competitive binding methods, such as RIAs, ELISAs, and the like. Other tests are Fluorescence resonance energy transfer (FRET), Surface plasmon resonance (Biacore), Western blotting, immunohistochemistry. Results from binding studies can be analyzed using any conventional graphical representation of the binding data, such as Scatchard analysis (Scatchard, Ann. NY Acad. Sci., 51:660-672 [1949]; Goodwin et al., Cell, 73:447-456 [1993]), and the like.

In another embodiment of the present invention, a method is provided for determining the effect of an agent on activity of pro-neurotrophins in cells presenting a receptor of the Vps10p-domain receptor family. Said method comprises the steps of:
b) administering said agent to a mammal expressing the receptor,
c) measuring the activity of pro-neurotrophins in said mammal,
d) comparing the measurement of step b) with a measurement obtained in the absence of the compound to be tested,
e) wherein the difference in the two measurements identifies the effect of said agent on the activity of pro-neurotrophins on cells presenting receptors of the Vps10p-domain receptor family.

The mammal may express the receptor naturally or may be transfected with the wild-type receptor gene.

The activity of said pro-neurotrophins in said mammal may be measured by one or more of the following measurements:
a) measuring expression level of a proneurotrophin responsive target gene, such as mRNA or protein in tissues of the mammal,
b) measuring expression level of a receptor as defined herein, such as mRNA or protein in tissues of the mammal
c) measuring receptor-mediated binding or transport of pro-neurotrophins bound to the receptor,
d) measuring uptake of pro-neurotrophins into cells of said mammal,
e) measuring signal transduction from said receptor or a related receptor in cells of said mammal, The related receptor may be p75 receptor or TrkA receptor.

In a preferred embodiment of said method, the method further comprises administering said agent to a mammal lacking expression of said receptor. Said mammal lacking expression of said receptor may only lack expression of said receptor in one or more selected tissues, and/or may have a lowered expression level of said receptor.

Methods for measuring expression of receptor mRNA or protein in tissues of the mammal are well known to those skilled in the art and have been described earlier. Methods for measuring receptor-mediated binding or transport of neurotrophins and/or pro-neurotrophins bound to the receptor are also well-known to those skilled in the art: said methods include, but are not restricted to, yeast two-hybrid screening, Biacore RTM screening, UV cross-linking, and immunoprecipitation.

Methods for measuring the uptake of pro-neurotrophins into cells of a mammal are also well known to those skilled in the art: said methods include but are not restricted to a method wherein proneurotrophin uptake is measured in cells presenting the receptor and cells not representing the receptor. The proneurotrophin is preferably labelled, such as labelled radioactively or fluorescently.

In another embodiment of the present invention, a method is provided for modulating the transport of at least one neurotrophin and/or pro-neurotrophin out of, or into a cell line or neuron of an animal, said method comprising administering to said animal a sufficient amount of an agent capable of binding a receptor of the Vps10p-domain receptor family. Said modulation may comprise an increase in the anterograde transport of the neurotrophin and/or pro-neurotrophin in the neuron. The modulation may alternatively comprise a decrease in anterograde transport of the neurotrophin and/or pro-neurotrophin in the neuron. In another preferred embodiment, the modulation comprises an increase in the retrograde transport of the neurotrophin and/or pro-neurotrophin in the neuron. In another preferred embodiment, the modulation comprises an decrease in retrograde transport of the pro-neurotrophin in the neuron. The modulation may be conducted by an agent as discussed above.

Library of Agents

In the present invention, libraries of compounds may be used to screen for agents capable of inhibiting binding between a Vps10p-domain receptor and a proneurotrophin.

As used herein, the term "library" means a collection of molecular entities or test compounds according to the present invention, herein also designated "library members".

In preferred embodiments of the present invention the library is a combinatorial library. Non-limiting examples of combinatorial libraries that may be used with the present invention and methods of producing such libraries are given in: Comprehensive Survey of Combinatorial Library Synthesis: 1998 Roland E. Dolle and Kingsley H. Nelson, Jr. J. Comb. Chem., 1999, pp 235-282; Comprehensive Survey of Combinatorial Library Synthesis: 1999 Roland E. Dolle J. Comb. Chem., 2000, pp 383-433; Comprehensive Survey of Combinatorial Library Synthesis: 2000 Roland E. Dolle J. Comb. Chem., 2001, pp 477-517; Comprehensive Survey of Combinatorial Library Synthesis: 2001 Roland E. Dolle J. Comb. Chem., 2002, pp 369-418 and Comprehensive Survey of Combinatorial Library Synthesis: 2002 Roland E. Dolle J. Comb. Chem., 2003, pp 693-753. The skilled person will appreciate that these protocols may be easily adapted to specific need of a particular embodiment of the present invention.

In one embodiment, these molecular entities can be natural oligomers (oligomers of building blocks occurring in nature) such as peptides, glycopeptides, lipopeptides, nucleic acids (DNA or RNA), or oligosaccharides. By way of example, a natural oligomer may be any peptide consisting of naturally occurring amino acid, even if said peptide comprises a sequence not present in nature. The libraries may comprise different natural oligomers or the libraries may comprise only one kind of natural oligomer, for example the library may be a peptide library. In another embodiment, they can be unnatural oligomers (oligomers comprising one or more building blocks not occurring in nature) such as chemically modified peptides, glycopeptides, nucleic acids (DNA or RNA), or, oligosaccharides, and the like. Said chemical modification may for example be the use of unnatural building blocks connected by the natural bond linking the units (for example, a peptide amide linkage), the use of natural building blocks with modified linking units (for example, oligoureas as discussed in Boeijen et al, 2001, J. Org. Chem., 66: 8454-8462; oligosulfonamides as discussed in Monnee et al, 2000, Tetrahedron Lett., 41: 7991-95), or combinations of these (for example, statine amides as discussed in Dolle et al, 2000, J. Comb. Chem., 2: 716-31). Preferred unnatural oligomers include oligomers comprising unnatural building blocks connected to each other by a naturally occurring bond linking. Said oligomers may thus comprise a mixture of naturally occurring and unnatural building blockslinked to each other by naturally occurring bonds. By way of example, the oligomer may comprise naturally occurring amino acids and unnatural building blocks linked by peptide bonds f.x. PNA or LNA. Thus, in one embodiment of the invention preferred oligomers comprise modified amino acids or amino acid mimics). Other preferred unnatural oligomers include, for example oligoureas, poly azatides, aromatic C—C linked oligomers and aromatic C—N linked oligomers. Still other preferred oligomers comprise a mixture of natural and unnatural building blocks and natural and unnatural linking bonds. For example, the unnatural oligomer may be any of the oligomers mentioned in recent reviews see: Graven et al., 2001, J. Comb. Chem., 3: 441-52; St. Hilaire et al., 2000, Angew. Chem. Int. Ed. Engl., 39: 1162-79; James, 2001, Curr. Opin. Pharmacol., 1: 540-6; Marcaurelle et al., 2002, Curr. Opin. Chem. Biol., 6: 289-96; Breinbauer et al., 2002, Angew. Chem. Int. Ed. Engl., 41: 2879-90. The libraries of the invention may also comprise cyclic oligomers, for example cyclic natural oligomers, such as cyclic peptides or cyclic unnatural oligomers. In certain embodiments of the invention, libraries of cyclic oligomers may be advantegous to use due to the rigid structure. This may result in higher selectively and affinity.

In yet another embodiment, the molecular entities may comprise non-oligomeric molecules such as peptidomimetics or other small organic molecules. Peptidomimetics are compounds that mimic the action of a peptidic messenger, such as bicyclic thiazolidine lactam peptidomimetics of L-proplyl-L-leucylglycinamide (Khalil et al, 1999, J. Med. Chem., 42: 2977-87). In a preferred embodiment of the invention, the library comprises or even more preferably consists of small organic molecules. Small organic molecules are non-oligomeric compounds of less than about 600 mass units containing any of a variety of possible functional groups and are the product of chemical synthesis, or isolated from nature, or isolated from nature and then chemically modified, and include, for example, Bayer's urea-based kinase inhibitors (Smith et al., 2001, Bioorg. Med. Chem. Lett, 11: 2775-78). Small organic compounds may for example be selected from the group consisting of alcohols, ethers, carboxylic acids, aryloxy, acyloxy, thiol, alkylthio, arylthio, heteroarylthio, sulphonyl, sulphoxy, amino, alkylamino, dialkylamino, acylamino, diacylamino, alkoxycarbonylamino, amides, alkyl, branched alkyl, aryl, heteroaryl, nitro, cyano, halogeno, silyloxy, keto, heterocycles, fused ring systems, fused heterocycles and mixtures thereof, wherein each of the aforementioned may be substituted independently on each position with one or more groups selected from the group consisting of —H, —OH, —SH, halogen, carboxyl, carbonyl, alkoxy, aryloxy, acyloxy, alkylthio, arylthio, heteroarylthio, sulphonyl, sulphoxy, amino, alkylamino, dialkylamino, acylamino, diacylamino, alkoxycarbonylamino, amides, alkyl, aryl, heteroaryl, nitro, cyano, halogeno, silyloxy, keto, heterocycles, fused ring systems, and fused heterocycles.

Non-limiting examples of small organic molecule libraries that may be used with the present invention and methods of producing them may for example be found in the reviews Thompson et al., 1996, Chem. Rev., 96: 555-600; Al-Obeidi et al., 1998, Mol. Biotechnol., 9: 205-23; Nefzi et al., 2001, Biopolymers, 60: 212-9; Dolle, 2002, J. Comb. Chem., 4: 369-418.

The libraries according to the invention may comprise at least 20, such as at least 100, for example at least 1000, such as at least 10,000, for example at least 100,000, such as at least 1,000,000 different test compounds. Preferably, the libraries comprises in the range of 20 to $10^7$, more preferably 50 to 7,000,000, even more preferably 100 to 5,000,000, yet more preferably 250 to 2,000,000 different compounds. In a very preferred embodiment of the present invention the libraries comprises in the range of 1000 to 20,000, such as in the range of 20,000 to 200,000 different test compounds. In preferred embodiments of the invention the library comprises in the range of 10,000 to 1,000,000 different test compounds.

Selection of an appropriate library is dependent upon the specific embodiment of the invention. For example, a totally random library designed to contain greatly diverse compounds may be used for screening for agents of the present invention. An advantage of this approach is that the outcome of the screening is not prejudiced in any specific manner.

Alternatively, a smaller, targeted library (hundreds to thousands of compounds) can be used, for example, starting with a known compound or compounds, and providing numerous variations of these known compounds for targeted screening. Alternatively, a smaller targeted library of compounds mimicking a compound known to inhibit binding between a pro-neurotrophin and a Vps-10pdomain receptor such as a Sortilin receptor may be prepared, for example using computer aided modelling followed by chemical synthesis. The smaller, targeted library can also comprise random molecules.

In one aspect the present invention also relates to methods of synthesizing libraries of test compounds, wherein said libraries are in particular useful for the screening for agents capable of inhibiting binding between a pro-neurotrophin and a Sortilin receptor especially SEQ ID NO: 25 of said Sortilin receptor or any fragment or variant of said SEQ ID NO. 25, said fragment having at least 70% sequence identity to SEQ ID NO. 25.

The libraries may be used by the general screening method described in example 5. By utilising a pipetting robot the method allows screening of very large libraries for the identification of agents capable of inhibiting binding between pro-neurotrophins and Sortilin. The agents may be any agent according to the present invention.

DESCRIPTION OF DRAWINGS

FIG. 2: Characterization of NGF binding to p75, TrkA, and Sortilin as measured by surface plasmon resonance analysis (BIAcore). Binding of 50-500 nM NGF was measured to 91.5 fmol/mm$^2$ immobilized p75-IgG-Fc chimeric protein (upper panel), to 66 fmol/mm$^2$ immobilized TrkA-IgG-Fc (middle panel), and to 51 fmol/mm$^2$ purified Sortilin extracellular domain (lower panel). The on and off rates—100 to 600 seconds and 600 to 1000 seconds, respectively—were recorded and the Kd values for NGF binding were calculated to ~1 nM for p75, ~2 nM for TrkA, and ~8 nM for Sortilin. Mature murine NGF was from Austral Biologicals (San Ramon, Calif.), recombinant human p75 neurotrophin receptor/Fc and human TrkA/Fc chimeras were from R&D systems (Oxon, UK). Human Sortilin was produced in stably transfected CHO-cells and purified as described elsewhere (Munck Petersen et al, EMBO J. (1999) 18:595-604).

All the data provided in this figure were obtained by surface plasmon resonance measurements (Biacore analysis).

FIG. 3: Characterization of proNGF binding to p75, TrkA, and Sortilin as measured by surface plasmon resonance analysis (Biacore). Binding of 25-500 nM pro-NGF was measured to 91.5 fmol/mm$^2$ immobilized p75-IgG-Fc chimeric protein (upper panel), to 66 fmol/mm$^2$ immobilized TrkA-IgG-Fc (middle panel), and to 51 fmol/mm$^2$ purified Sortilin extracellular domain (lower panel). The on and off rates—100 to 600 seconds and 600 to 1000 seconds, respectively—were recorded and the Kd values for proNGF binding were calculated to ~12 nM for p75, ~15 nM for TrkA, and ~5 nM for Sortilin. Human recombinant proNGF was produced and purified in *E. coli* as described (Rattenholl et al, Eur. J. Biochem. (2001) 268:3296-3303). All other reagents were as described in the legend to FIG. 2. All the data provided in this figure were obtained by surface plasmon resonance measurements (Biacore analysis)

FIG. 4: Characterization of binding of the proNGF propeptide to p75, TrkA, and Sortilin as measured by surface plasmon resonance analysis (Biacore). Binding of 25-500 nM propeptide was measured to 91.5 fmol/mm$^2$ immobilized p75-IgG-Fc chimeric protein (upper panel), to 66 fmol/mm$^2$ immobilized TrkA-IgG-Fc (middle panel), and to 51 fmol/mm$^2$ purified Sortilin extracellular domain (lower panel). The on and off rates—100 to 600 seconds and 600 to 1000 seconds, respectively were recorded and the Kd values for proNGF propeptide binding were calculated to ~8 nM for Sortilin. There was no detectable binding to p75 and TrkA. The human NGF-propeptide expressed in *E. Coli* was provided by Elisabeth Schwarz, Martin-Luther-Universität Halle-Wittenberg, Halle/Saale, Germany. All other reagents were as described in the legends to FIGS. 2 and 3. All the data provided in this figure were obtained by surface plasmon resonance measurements (Biacore analysis)

Figure 1:
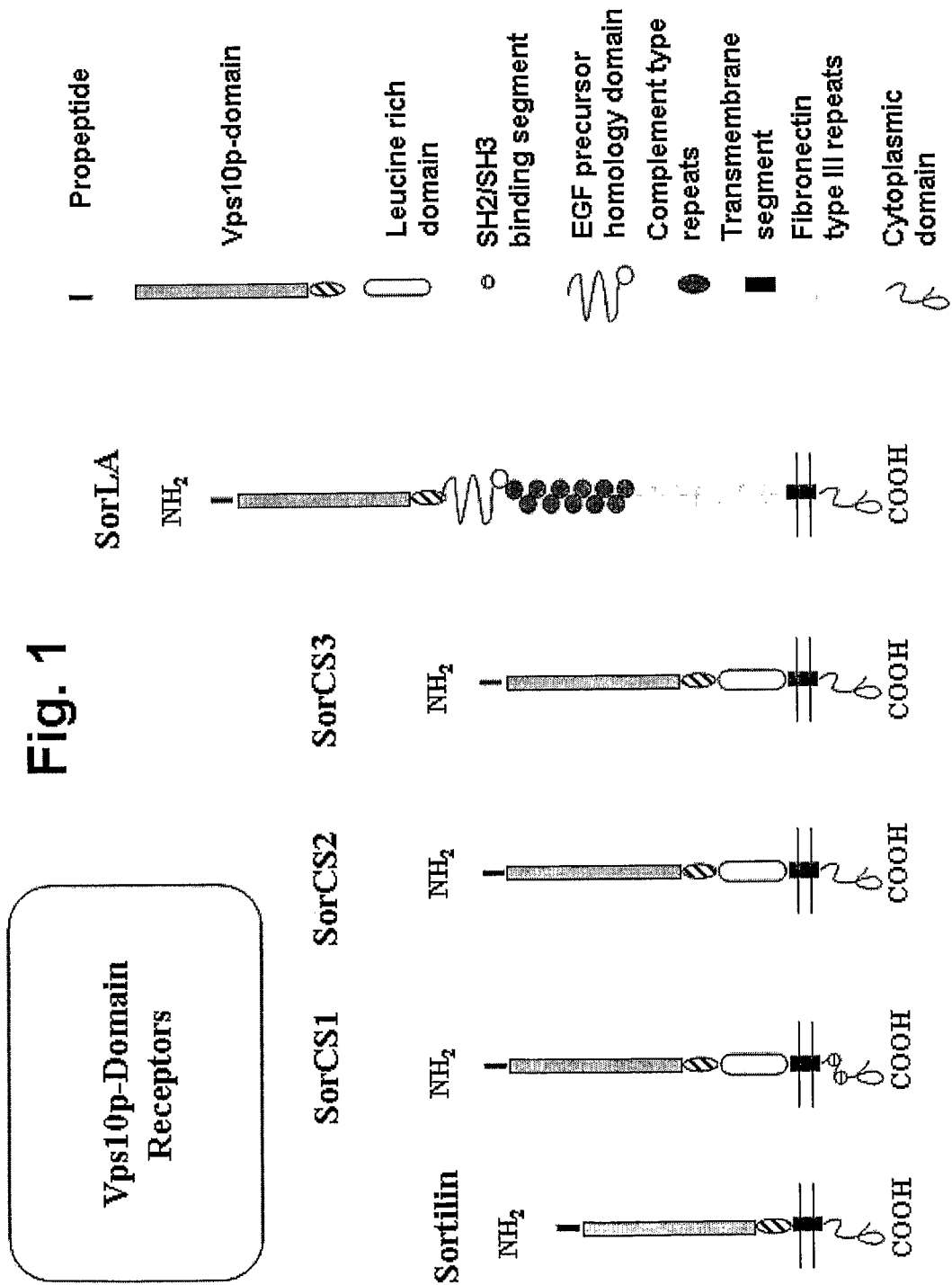
FIG. 1: Examples of Vps10p-domain receptors. Their structural composition is indicated.
Figure 5:
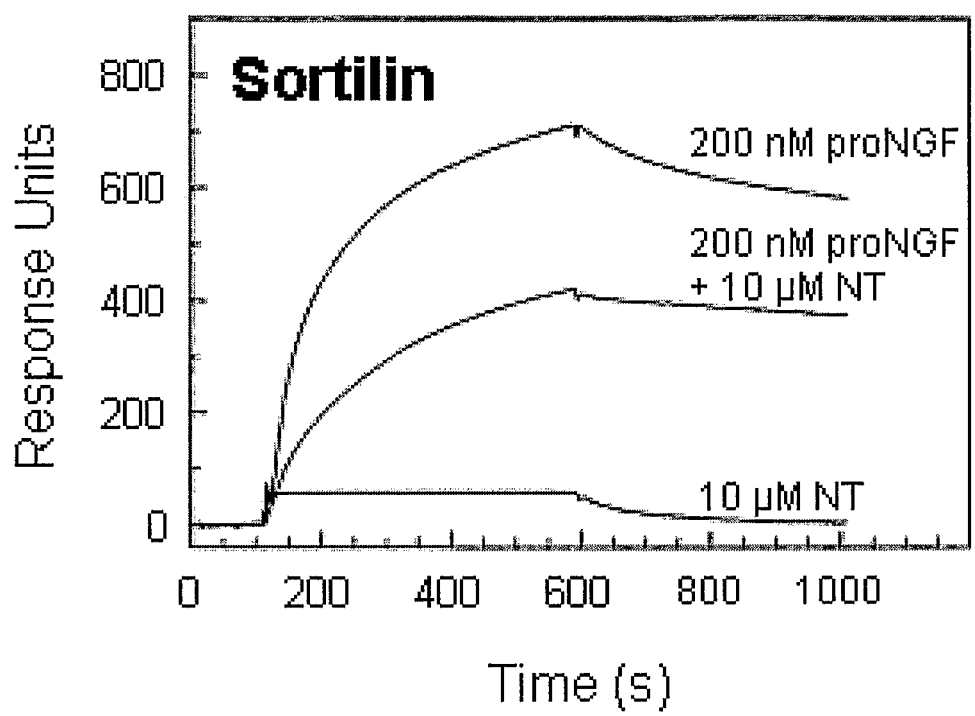

FIG. 5: This reference example which is not a part of the present invention demonstrates that it is possible to inhibit binding of a pro-neurotrophin to a Vps10p-domain receptor. The reference example figure displays inhibition of pro-NGF binding to immobilized Sortilin by neurotensin as measured by Biacore analysis. Binding of 200 nM proNGF to 51 fmol/mm$^2$ immobilized Sortilin is inhibited by ~45% following coinjection with 10 μM neurotensin. Binding of neurotensin alone is shown for comparison. Neurotensin was obtained from Sigma-Aldrich (St. Louis, Mo.). All other products were as indicated above. All the data provided in this figure were obtained by surface plasmon resonance measurements (Biacore analysis)

FIG. 6: This reference example which is not a part of the present invention demonstrates that it is possible to inhibit binding of a pro-neurotrophin to a Vps10p-domain receptor. The reference example figure displays proNGF binding to immobilized Sortilin by RAP (receptor-associated protein), the propeptide of proNGF, and the Sortilin propeptide. The inhibitors were prebound to Sortilin followed by coinjection with 200 nM proNGF. The baselines have been corrected for the signals obtained in the presence of each of the inhibitors. Maximal proNGF binding is measured without preincubation with the respective inhibitors. Binding of 200 nM pro-NGF to 51 fmol/mm$^2$ immobilized Sortilin is inhibited ~65% by 10 μM RAP, ~85% by 5 μM og the proNGF propeptide and ~65% by 5 μM the Sortilin propeptide. All the data provided in this figure were obtained by surface plasmon resonance measurements (Biacore Analysis)

Figure 7:
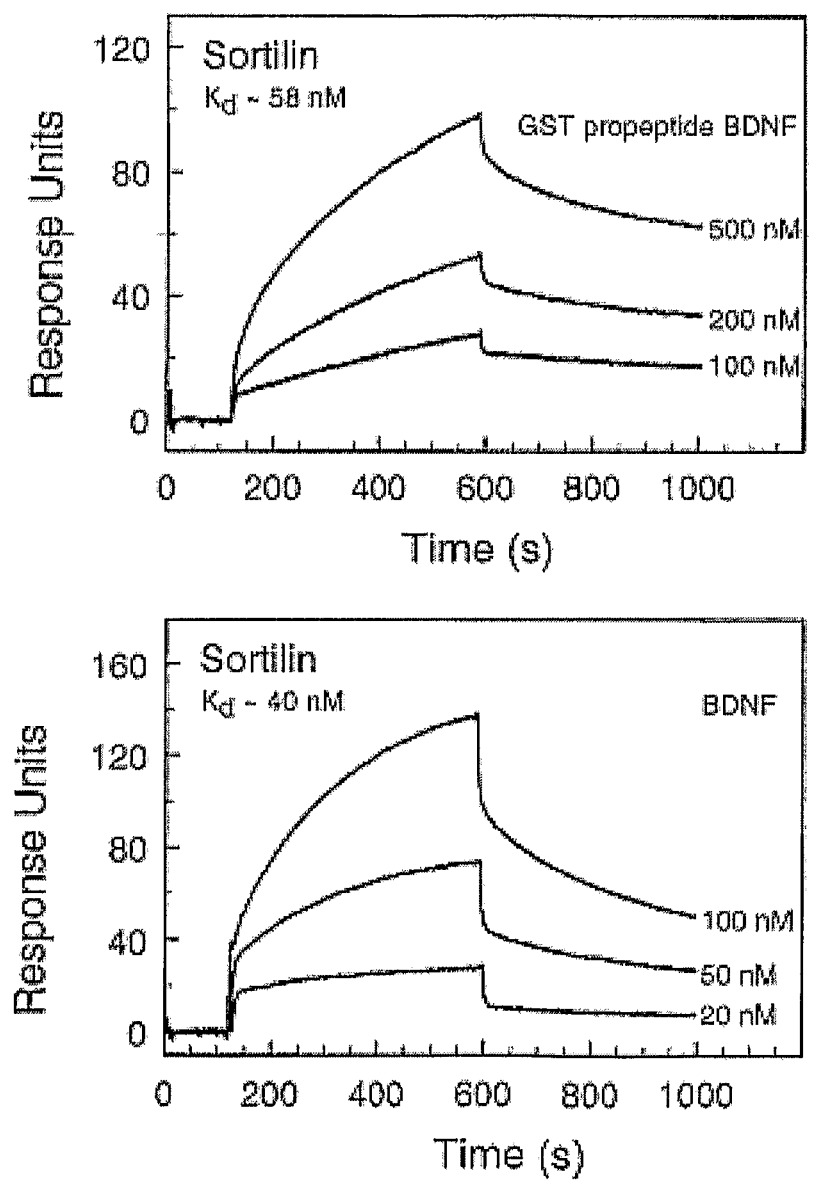

FIG. 7: Characterization of binding of BDNF and the pro-domain of proBDNF to purified Sortilin as measured by surface plasmon resonance (Biacore). Mature recombinant human BDNF was from Promega (#G1491) and the pro-domain of human BDNF fused to GST (glutathione S-transferase) was produced in *E. coli* and purified by glutathione-sepharose affinity chromatography. Binding of the pro-domain of proBDNF (a GST-fusion protein, upper panel) or BDNF (lower panel) was measured to 94 fmol/mm2 immobilized purified Sortilin extracellular domain. The experiment was carried out essentially as described for FIGS. 2-4. The on and off rates—100 to 600 seconds and 600 to 10000 seconds, respectively—were recorded and the Kd values for ligand binding were calculated to ~58 nM for the GST-pro-domain of proBDNF, and ~40 nM for mature BDNF. Other preparations of mature BDNF have shown Kd values for ligand binding at 10 nM. All the data provided in this figure were obtained by surface plasmon resonance measurements (Biacore analysis)

FIG. 8: Functional characterization of recombinant his-5-tagged neurotrophin pro-domains. A. Coomassie staining of purified polypeptides of pro-dom-NGF (residues Glu$^1$-Arg$^{102}$) and pro-dom-BDNF (residues Ala$^1$-Arg$^{110}$) cloned into the pET-30 fXa/LIC vector (Novagen) that adds the two N-terminal poly-histidine and S-peptide tags. B, C. The presence of both tags is verified by Western blotting and detection by using a primary antibody against histidine followed by incubation with HRP-conjugated secondary antibody (B) or with a directly HRP-conjugated version of S-protein (C). D, E. Surface plasmon resonance analysis of the binding of the bacterial pro-domains of NGF (D) and BDNF (E) to the immobilized extracellular domain of sortilin.

FIG. 9: Alignment of the amino acid sequences of the four mammalian neurotrophins. An alignment of the sequences of NGF, BDNF, NT-3, and NT-4/5, showing a high degree of conservation for the mature part, and much less sequence conservation among the pro-domains. Strictly conserved residues are highlighted on a black background, and partly conserved residues on a grey background.

Figure 10:
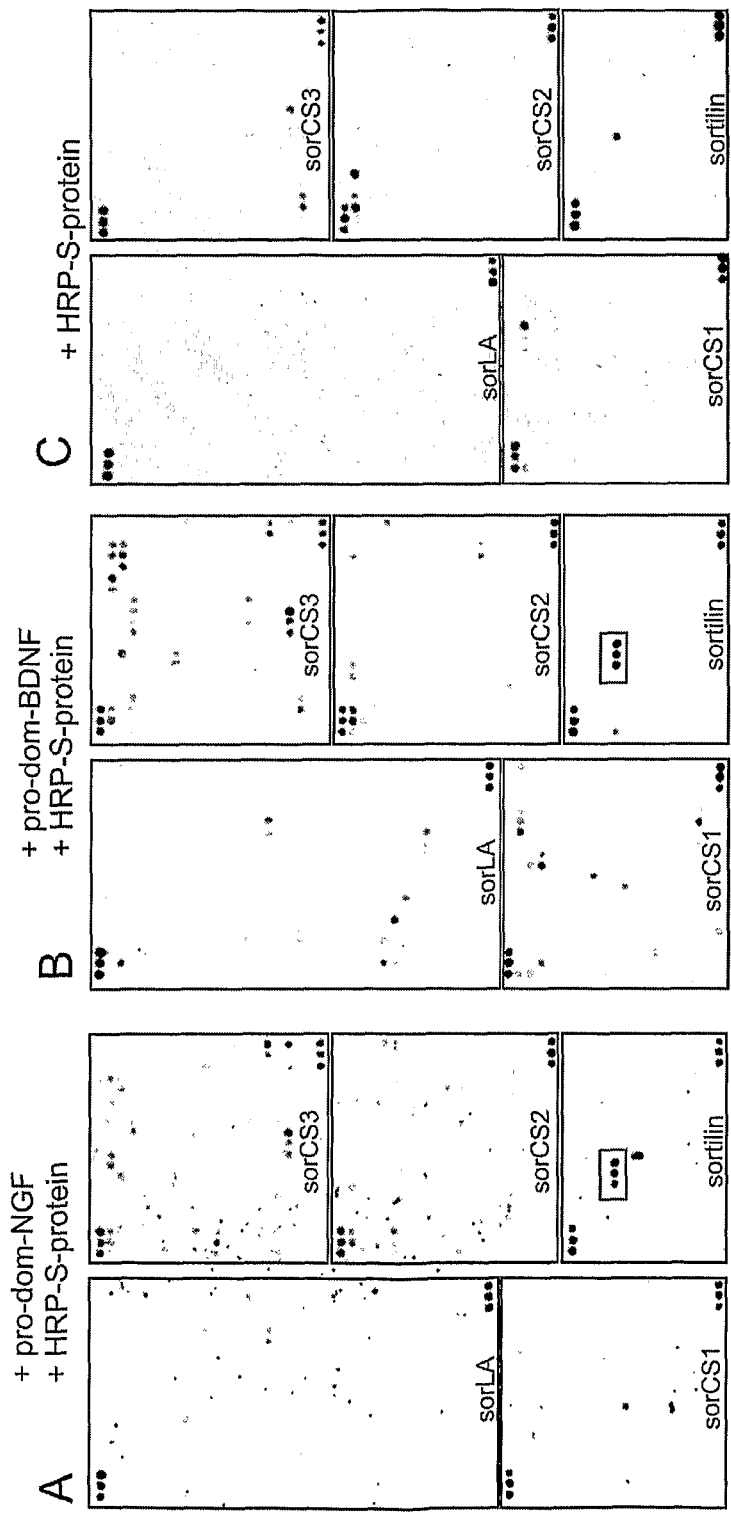

FIG. 10: SPOT analysis of pro-dom-NGF/BDNF binding to Vps10p receptors including sortilin and detection with HRP—S-protein. Membranes containing overlapping 16-mer peptides of the five human Vps10p-domain containing receptors (Sortilin, SorLA, SorCS1, SorCS2, and SorCS3) were incubated either in the presence of pro-dom-NGF (20 μg/mL, A) or pro-dom-BDNF (20 μg/mL, B) or in the absence of ligand (C). Bound ligand was detected by incubation of the membrane with HRP-conjugated S-protein, that also binds specifically to control peptides present on the upper left and lower right corner of each dissected receptor. A specific binding site for the neurotrophin pro-domains is shown in the box consisting of three consequtive sortilin binding peptides (SPOTs 67-68-69), but is not seen for detection solely using the HRP—S-protein.

Figure 11:
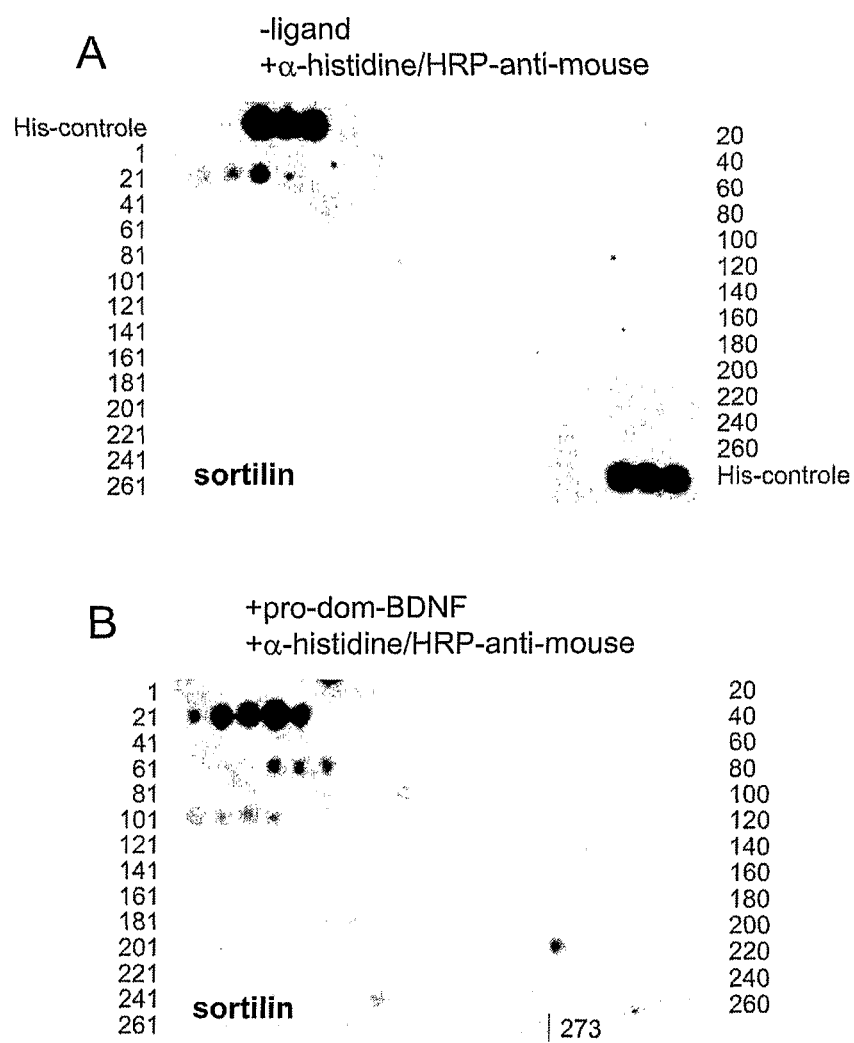

FIG. 11: SPOT analysis of pro-dom-BDNF binding to sortilin using the anti-histidine immunodetection. Repeated analysis of pro-dom-BDNF binding to the peptide library but detection using a primary antibody against poly-histidine followed by a HRP-conjugated anti-mouse secondary antibody showed a slight shift towards a specific interaction with peptides 64-65-66 (B), which is not identified when the membrane was not incubated with ligand prior to detection (A). SPOTs corresponding to 22-25 represent binding of the detection system independent on pro-dom-BDNF.

FIG. 12: Independent confirmation of pro-dom-BDNF binding to SPOTs 67-68-69 by HRP—S-protein detection. A new membrane was synthesized and probed for a newly produced batch of pro-dom-BDNF showing specific binding to SPOTs 67-68-69 at 1 min of exposure (A) to verify the binding to reside around this sortilin sequence. Following 5 min of exposure, a few additional peptides also show minor interactions.

FIG. 13: Amino acid sequence of SPOTs 64-69. The 16-mer sortilin sequences that correspond to SPOTs 64-69 likely to harbor the major binding site for pro-domains of neurotrophins.

FIG. 14: Alignment of the sortilin Vps10p domain. The repeated presence of the Asp-box motif (S/T-X-D-X-G-X-X-W/F) was used to make an alignment displaying an internal sequence repetition found in e.g. domains having a beta-propeller fold, where residues located around this motif are present on the molecular surface. Strictly conserved residues are highlighted on a black background, and partly conserved residues on a grey background.

Figure 15:
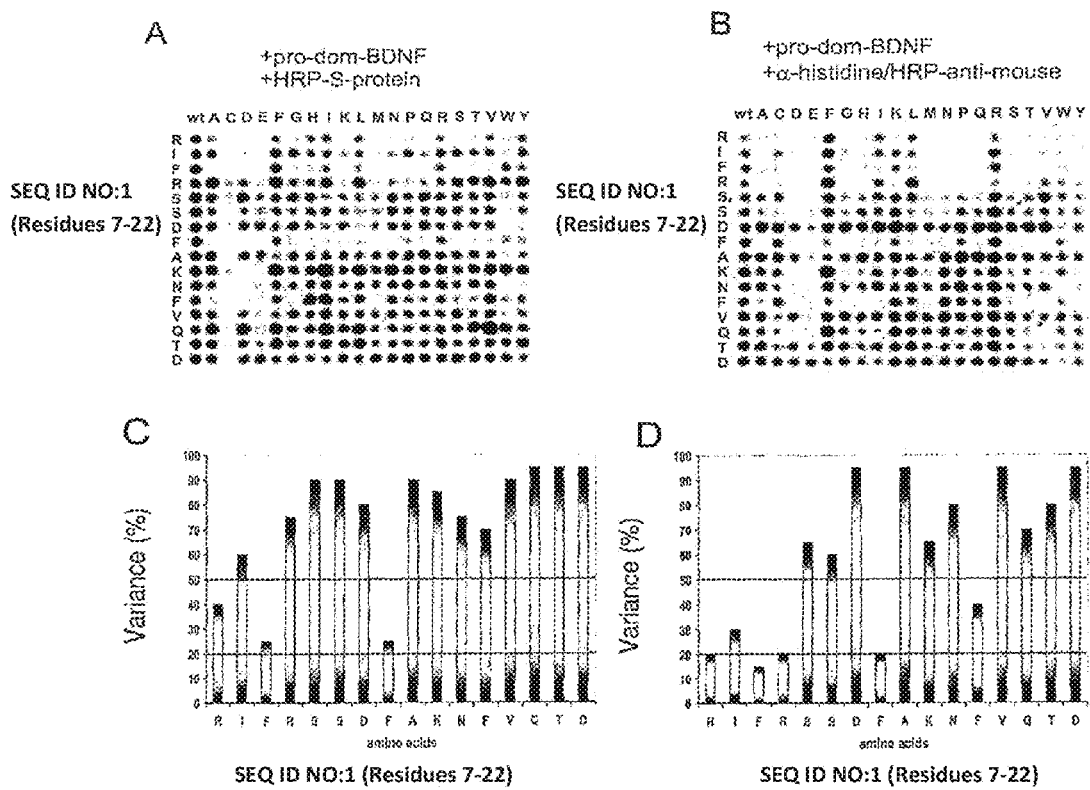

FIG. 15: Substitution analysis of the RIFRSSDFAKN-FVQTD peptide (SEQ ID NO:25, residues 7-22). Pro-dom-BDNF binding analysis to a peptide with the wild-type sortilin sequence RIFRSSDFAKNFVQTD (SEQ ID NO:25, residues 7-22) listed to the left on the membrane. Binding to mutant peptides where each amino acid has been substituted with each of the 20 naturally occurring amino acids is used for identification of specific residues important for interaction with the immature part of neurotrophins Detection using either HRP-S-protein (A) or the anti-histidine immunospecific method (B) identifies virtually identical residues for this method. C, D. Bar graph representation of the binding variation upon amino acid substitution. This method might be suitable for identification of super-binding peptides.

Figure 16:
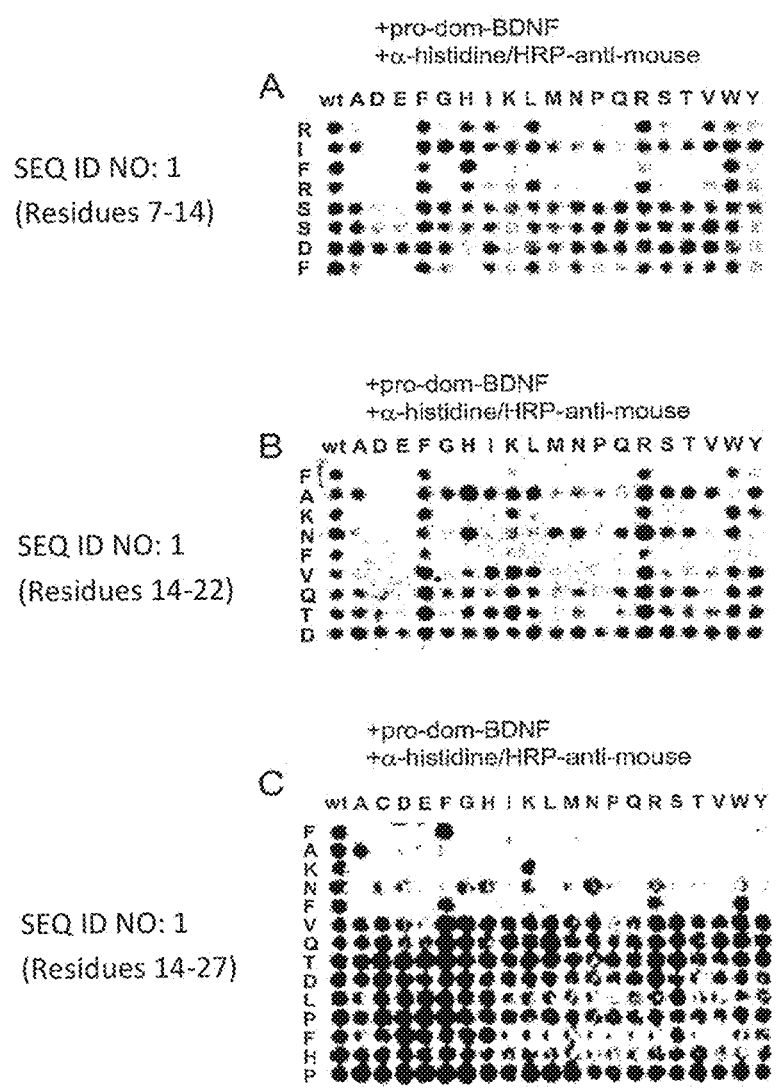

FIG. 16: Substitution analysis of pro-dom-BDNF binding to RIFRSSDF (SEQ ID NO:1, residues 7-14) and FAKN-FVQTD (SEQ ID NO:1, residues 14-22) peptides. A, B. Splitting of the peptide shown in FIG. 8 provides evidence that the longer peptide contains two independent binding motifs for prodom-BDNF binding, The substitution analysis clearly identify the two sequences RIFR (A) (SEQ ID NO:1, residues 7-10) and FAKNF (B) (SEQ ID NO:1, residues 14-18) as specific interaction sites for the pro-domains of BDNF. C. Confirmation by substitution analysis that the FAKNF (SEQ ID NO:1, residues 14-18) motif is not C-terminal extended.

FIG. 17: Length analysis of pro-dom-BDNF binding to sortilin peptides. By deletion of single amino acid residues, the length of a minimal functional sortilin peptide is determined, confirming that small e.g. tetrameric sequences have high affinity for pro-dom-BDNF (high-lighted in white on black background).

FIG. 18: Surface plasmon resonance binding analysis of sortilin peptides to prodom-NGF and -BDNF. The direct interaction between sortilin peptides (as identified by SPOT analysis) and the pro-domains of NGF and BDNF was verified by surface plasmon resonance analysis using immobilized pro-dom-NGF and -BDNF. A concentration series of the RSSDFAKNFVQTDLPF peptide (A) (SEQ ID NO:25, residues 10-25) (containing only one of the two potential binding sites residing in this region) or the RIFRSSDFAKNF (B) (SEQ ID NO:25, residues 7-18) confirming the result of a direct binding as seen from the immobilized peptide analysis on the SPOT membrane. By comparison of binding curves (sensorgrams) for a single peptide concentration to flow cells containing identical amounts of immobilized pro-dom-NGF and -BDNF, a higher affinity of the peptides towards BDNF than NGF could be observed, in line with previous reports describing a similar pattern for the binding of pro-BDNF and pro-NGF to full-length sortilin, supporting the concept that these peptides contain a major binding epitope. The numbering in this figure refers to the mature part of Sortilin.

Figure 19:
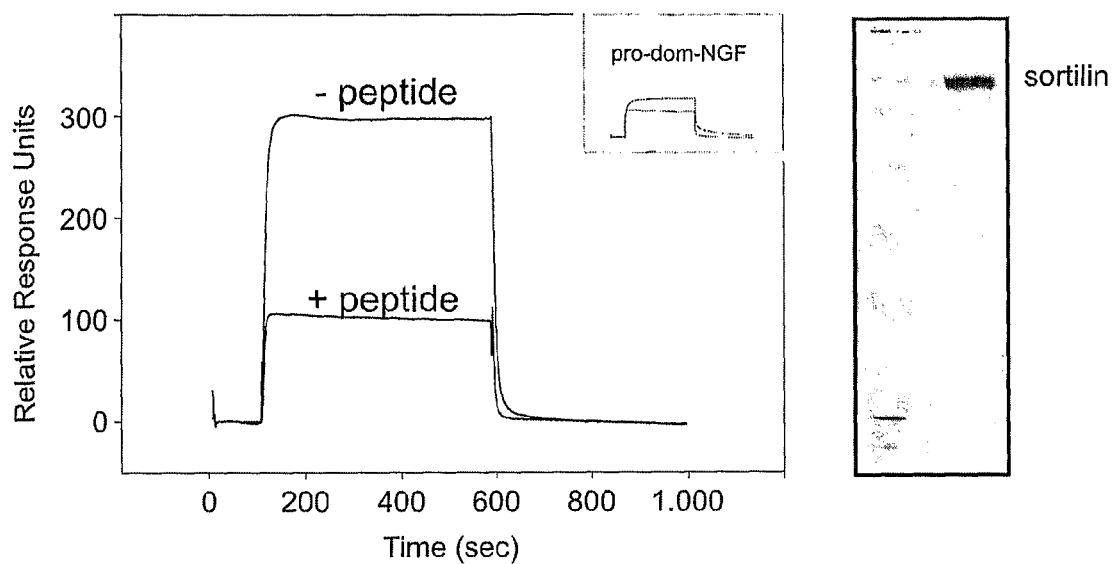

FIG. 19: Surface plasmon resonance analysis of competition studies by the sortilin peptides. Recombinant sortilin was purified from 293 cells, and used for binding studies to immobilized pro-dom-BDNF (−peptide; RSSDFAKNFVQTDLPF (SEQ ID NO:25, residues 10-25)), and binding was significantly inhibited in the presence of the identified sortilin peptides (+peptide). The inset indicates a similar effect of the peptide in the competition of sortilin binding to immobilized pro-dom-NGF, and the quality of applied sortilin is indicated to the right by a silver stained SDS-PAGE analysis.

Figure 20:
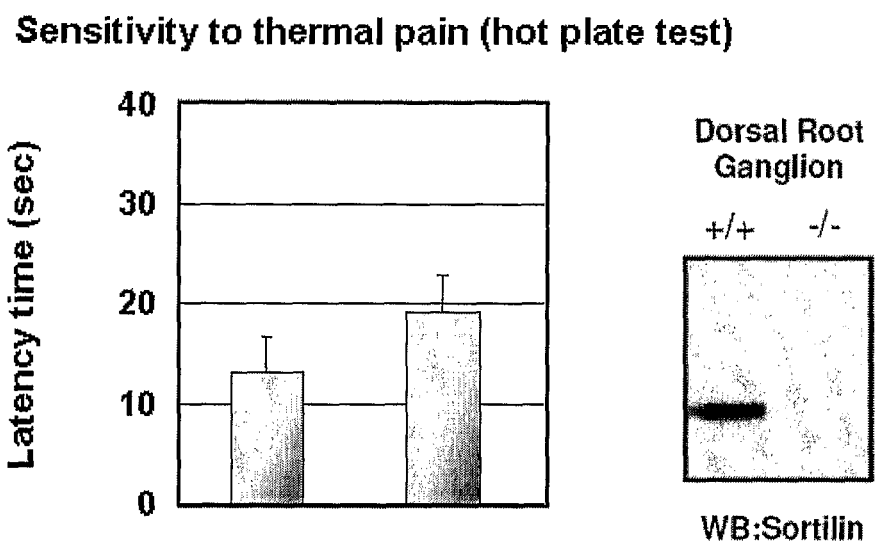

FIG. 20: Thermal hypoalgesia in Sortilin deficient mice as determined by the hot plate assay. The hot plate test was performed as follows. Wild-type (sortilin+/+) and sortilin knockout mice (sortilin−/−) were placed on a thermoregulated Plactronic hot plate set at 55° C. Each animal was subsequently observed for licking their hindlimb or jumping in response to the heat. The first response was registered per animal. A 30 sec cut-off was employed in order to prevent tissue damage.

Figure 21:
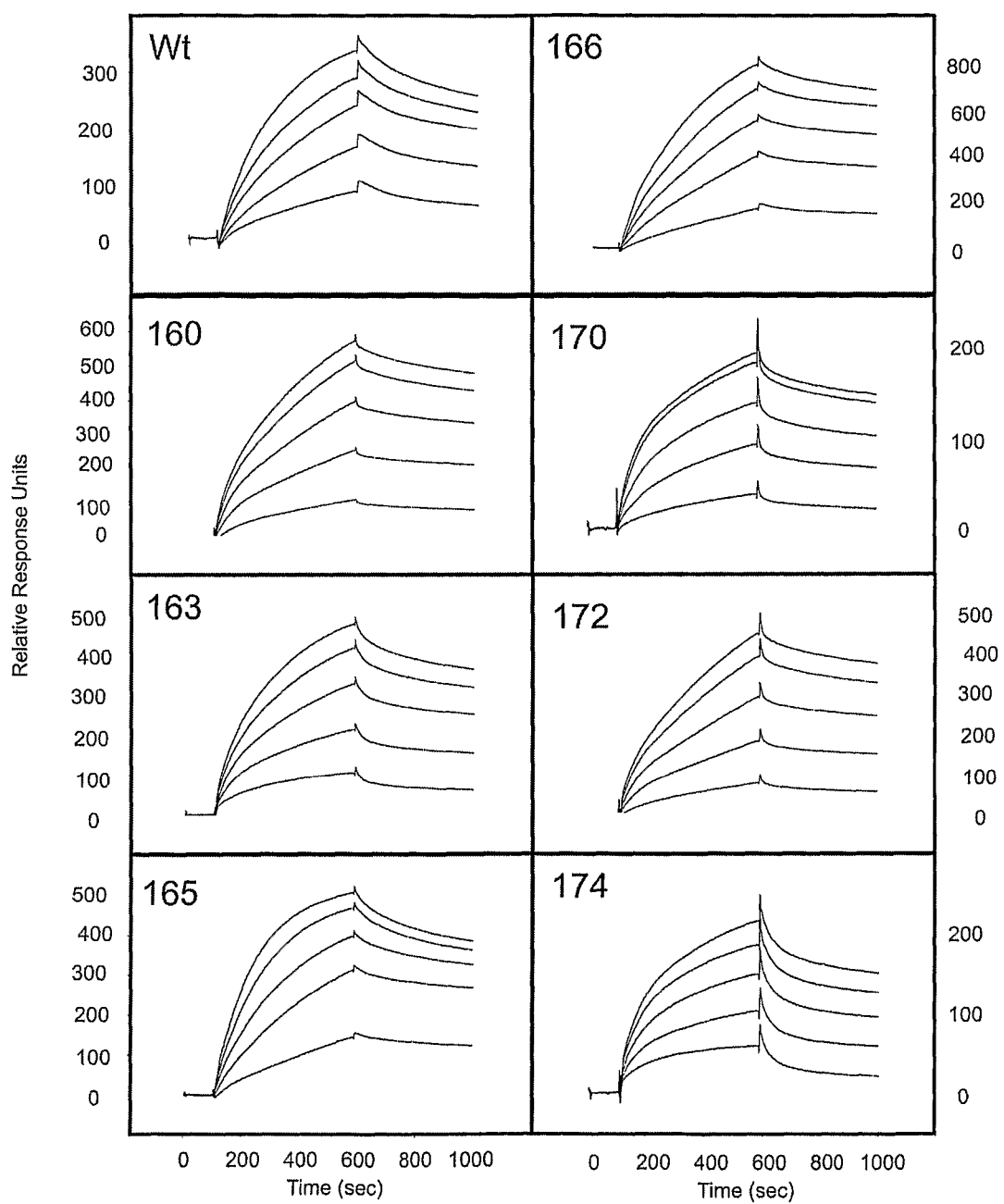

FIG. 21: Representative sensorgrams of pro-dom-NGF binding at similar concentration series of 10, 20, 30; 40, and 50 nM to biosensor chips containing immobilized sortilin wt or single residue mutations as indicated. Each sortilin construct was immobilized to a similar surface density allowing for direct comparison among different receptor domains.

Figure 22:
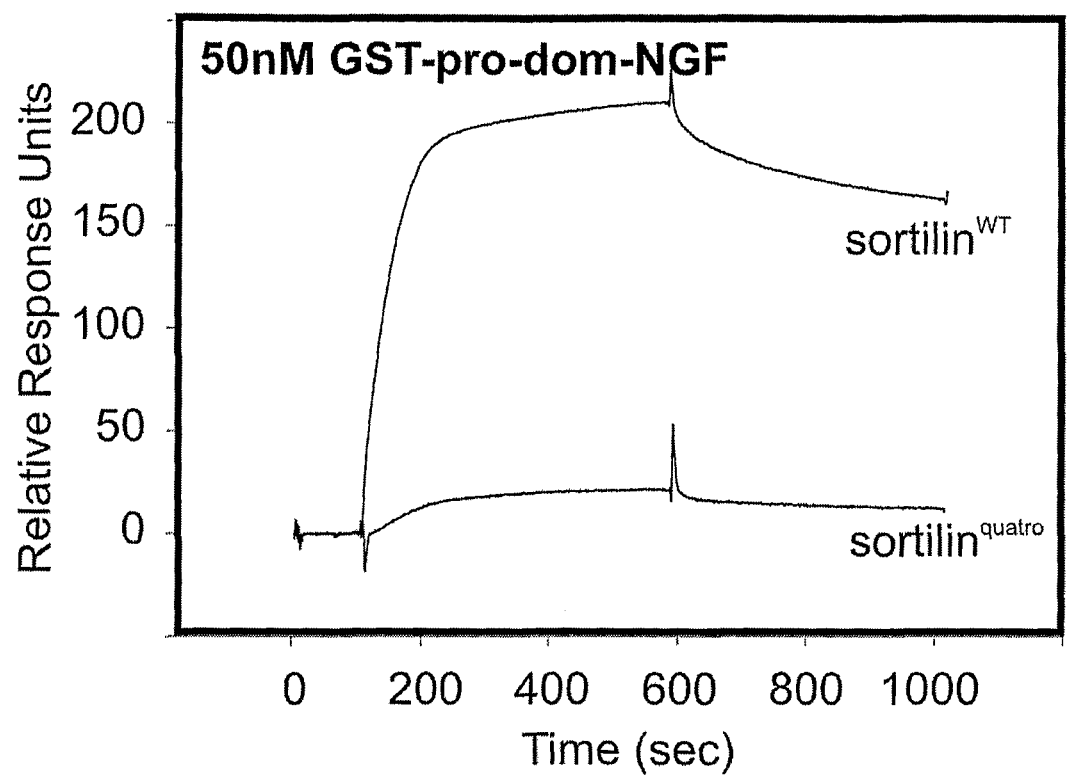

FIG. 22: Surface plasmon resonance analysis of 50 nM GST-pro-dom-NGF binding to immobilized sortilin wt or the sortilin quatro mutant (containing quadruple substitution at R163A, F165A, R166A, F170A) as indicated. Binding is severely affected upon mutation deleting the entire RIFR (SEQ ID NO:25, residues 7-10) motif and the proximal phenylalanine residue of the FAKNF (SEQ ID NO:25, residues 14-18) motif as seen by the much lower response level.

EXAMPLES

Example 1

Materials and Proteins

To obtain tagged forms of the neurotrophin pro-domains readily for detection in SPOT analysis, constructs were prepared for each protein allowing for addition of N-terminal S-peptide and poly-histidine tags. Template cDNA for human NGF and BDNF was ATCC clones used for generation of fragments spanning residues Glu1-Arg102 of NGF (SEQ ID NO:6) and Ala1-Arg110 of BDNF (SEQ ID NO:7) using the primer pairs

```
                                            (SEQ ID NO: 45)
5'GGTATTGAGGGTCGCGAACCACACTCAGAGAGCAATGTCCC3', (SEQ ID NO: 46)
3'GGGGGAAGTTGTCCTGAGTGTCCTCGTTCGCCACTCCGAGATTGAGAG

GAGA5'
and (SEQ ID NO: 47)
5'GGTATTGAGGGTCGCGCCCCCATGAAAGAAGCAAACATCCGAGG3', (SEQ ID NO: 48)
3'CACGTTTGTACAGGTACTCCCAGGCCGCGACTCCGAGATTGAGAGGAG

A5',
``` with compatible overhangs for ligation independent cloning into the pET-30 Xa/LIC vector from Novagen (cat. no. 70073-3) and amplification using Phusion DNA poly merase and following the protocol as provided by manufacturer. Proteins were expressed in the BL21/DE3 strain of *E. coli*, efficiently extracted from bacterial inclusion bodies using the Bugbuster reagent from Novagen (cat. no. 70921) with added benzonase (Novagen, cat. no. 70750), and purified by standard $Ni^{2+}$-NTA affinity chromatography in 500 mM NaCl, 5 mM Imidazole, and 20 mM Tris-HCl, pH 8.0. Protein elution was performed in buffer supplemented with 20 mM EDTA. Verification of the intact tagged versions of pro-domain-NGF and pro-domain-BDNF was carried out by SDS-PAGE analysis followed by commassie staining or Western blotting using either antibody against the histidine tag from Sigma (H-1029)

and secondary HRP-conjugated anti-mouse antibody from Calbiochem (cat. no. 401207), or alternatively by direct binding of HRP-conjugated S-protein from Novagen (cat. no. 69047-3).

For the production of the Sortilin ectodomain, a construct encompassing the entire coding region of the N-terminal part of human Sortilin including the endogenous signal peptide and followed by a C-terminal poly-histidine tag inserted in the pCEP-Pu vector was kindly provided by D. Militz, Berlin. The DNA was transferred into EBNA293 cells that were selected by G418 (Gibco cat. no. 10131-027, 300 µg/ml) and Puromycin from Sigma (cat. no. P8833, 1 µg/ml) before proteins were collected from medium conditioned for 48 h, and used for purification by applying to $Ni^{2+}$-NTA Sepharose. The secreted recombinant Sortilin polypeptide chain spanning the entire extracellular domain of human Sortilin is thus ending at Ser725 (+AMIEGRGVGHHHHHH (SEQ ID NO:49) containing the fXa site and poly-histidine tag). The quality of the protein was tested by silver staining of SDS-PAGE analysis. Peptides for binding and competition studies were synthesized in house, or from Eurogentec.

Example 2

Surface Plasmon Resonance Analysis

Determination of direct binding of ligand to immobilized protein was performed on a Biacore2000 instrument (Biacore, Sweden) using CaHBS as standard running buffer (10 mM HEPES, pH 7.4, 140 mM NaCl, 2 mM CaCl2, 1 mM EGTA, and 0.005% Tween-20). A biosensor chip from Biacore (CM5, cat. no. BR-1000-14) was activated using the NHS/EDC method as described by supplier followed by coating with Sortilin to a protein density of 79 fmol/mm$^2$, and used for affinity measurements of the recombinant pro-domains of NGF and BDNF. Regeneration of the flow cell after each cycle of ligand binding experiment was performed by two 10 uL pulses of regeneration buffer (10 mM glycine-HCl, pH 4.0, 500 mM NaCl, 20 mM EDTA, and 0.005% Tween-20) and a single injection of 0.001% SDS. Fitting of sensorgrams for affinity estimations was performed using the Biaevaluation version 3.1. Following similar protocols, immobilization of pro-dom-NGF or pro-dom-BDNF was also performed on a CM5 biosensor chip using the NHS/EDC coupling kit according to manufactures instructions (Biacore, Sweden), giving similar surface densities of immobilized protein (~300 fmol/mm$^2$). Purified peptides were applied to the chip at increasing concentrations to verify the direct binding of pro-neurotrophic domains to linear Sortilin peptides. This chip was subsequent used to examine the binding of 390 nM wild-type Sortilin domain in CaHBS buffer at a flow of 5 uL/min, which in the absence of any competing peptide gave a ~300 RU signal. For competition using 300 uM of the peptide, only ⅓ of the Sortilin can bind to immobilized pro-dom-BDNF (showing ~66% inhibition by the peptide).

Example 3

Cellulose Membrane Preparation

Peptide libraries were generated for all members of the Vps10p-domain receptor gene family or specific peptide variations in terms of substitution or length of identified Sortilin binding peptides. A total of 2181 peptides was used for representation of the Sortilin gene family, corresponding to 273 peptides for Sortilin (accession code: CAA66904), 734 peptides for SorLA (accession code: NP_003096), 389 peptides for SorCS1 (accession code: NP_001013049), 382 peptides for sorCS2 (accession code: Q96PQ0), and 403 peptides for SorCS3 (accession code: CAI64579), with a 13 amino acid overlap between 16-mers.

A cellulose support is prepared as a N-modified cellulose-amino-hydroxylpropyl ether membrane, and all rounds of synthesis starts with SPOT definition by 9-fluorenyl-methoxycarbonyl-β-alanine-pentafluorophenyl ester that creates an alanine linker between peptide and membrane. Then followed an automated linear synthesis of stepwise addition of the different amino acids protected at their amino terminal by 9-fluorenyl-methoxycarbonyl and appropriate side chain protection for the growing peptide chain. The pattern of deprotection, activation, and coupling continued until 16-mer peptides were produced, resulting in an equally distributed array of covalently anchored peptides to the cellulose support at their C-terminal and an N-terminal free end. The membrane was finally blocked in blocking buffer from Sigma (cat. no. B6429) diluted in TBS and supplemented with 5% saccharose (Merck, cat. no. K32055087 422) for 2 h before the predefined peptide library is ready for ligand binding analysis.

Example 4

Binding Studies of Cellulose-Bound Peptides

The membrane-bound libraries were incubated with a combined S-peptide and polyhistidine-tagged pro-domains (10 ug/mL) in blocking buffer over night at 4 C, followed by a second incubation with 1 ug/mL of HRP-conjugated S-protein from Novagen (cat. no. 69047-3) also in blocking buffer but for 3 h at room temperature. Subsequently, the membrane was washed three times for 10 min with TBS before quantitative characterization of bound ligand was carried out using the UptiLight chemoluminescence substrate from Uptima (cat. no. UP99619A) and the Lumilmager instrument from Roche Diagnostics, providing the SPOT signal intensities in Boehringer Light Units (BLUs). Alternatively, detection of bound ligand was performed by an immunochemical assay, where antibody against the histidine tag was from Sigma (H-1029) and the secondary HRP-conjugated anti-mouse antibody was from Calbiochem (cat. no. 401207). Incubations followed standard Western blotting procedures and SPOT detection as above.

The method of substitution analysis and length analysis to identify unique single amino acid residues and to determine the minimal peptide sequence, respectively, for efficient binding of the pro-domain-neurothrophins to the Sortilin peptide, followed similar protocols as for the initial testing of ligand binding to the SPOT membrane.

Example 5

Radioligand Assay

Recombinant Sortilin (38 pmol) is labeled with [$^{125}$I] using the Iodogen iodination reagent from Pierce (cat. no. 28600) to a specific activity of ~5×10$^{18}$ cpm/mol Sortilin. The pro-dom-NGF (or -BDNF) is coated in maxisorp microtiter wells from Nunc (cat. no. 439454) by incubation for 16 h at 4 C in 50 mM NaHCO$_3$, pH 9.6. After blocking using 5% bovine serum albumin (Sigma, cat. no. A9647) for 2 h at room temperature, the wells are washed three times with MB buffer (10 mM HEPES, pH 7.4, 140 mM NaCl, 2 mM CaCl$_2$, and 1 mM MgCl$_2$) before incubation with $^{125}$I-Sortilin allowing for total binding of ~2.000 cpm/well and varying amounts of competing peptide concentrations are performed for 16 h at 4° C. in MB buffer supplemented with 2% bovine serum albumin. Following washes with MB buffer, bound radioactivity is released by adding 10% SDS. Nonspecific binding of tracer to wells coated only with bovine serum albumin is determined and subtracted from the values determined in the binding experiments. Fitting data point to binding equations using the Prism software from GraphPad, version 4, made estimation of $IC_{50}$ constants.

Example 6

Investigation of Antagonistic Properties

Investigation of the properties of the peptide as an in vivo antagonist of proneurotrophin binding to Sortilin in an animal model of nerve lesions in the rat brain.
i) Determination of $IC_{50}$ values for the full-length peptide as well as smaller peptides as identified from our recent length analysis illustrate that the 4-mer peptides (e.g. RIFR) binds very strongly to the pro-domains of pro-NGF and pro-BDNF. This will be performed either by:
i-a) $^{125}$I-labelling of Sortilin and solid state competition assays using immobilized pro-domain-NGF/BDNF in maxisorb microtiter wells, followed by competition studies using increasing levels of the various peptides in order to compare inhibitory properties.
i-b) Using surface plasmon resonance analysis for concentration series of the various peptides similar to the results displayed for a single concentration of A2 peptide.
ii) Testing the influence of essential residues as identified by the substitution analysis for their contribution to pro-neurotrophin binding. Using the EBNA293 expression system for recombinant production of the Sortilin ectodomain (silver stained gel was included in one of the figures), single-residues alanine mutants of the Sortilin domain are currently produced using site-directed mutagenesis. The following 7 mutants have been tested: R160A, R163A, F165A, R166A, F170A, K172A, F174A as numbered according to pro-Sortilin specified in the sequence overview. Due to the indicated presence of two binding sites within this Sortilin region, production of double, triple, etc. mutants for verification of the binding site in the context of the entire Sortilin Vps10p domain might be required.

iii) Provided that it is possible to identify residues from (ii), essential for the interaction between Sortilin and the pro-domain of pro-NGF/BDNF, preparation of expression vectors (in pcDNA3.1/invitrogen) for the full-length Sortilin protein carrying such mutations will be performed. Use of these constructs (together with $p75^{NTR}$) for cell transfection should produce cells insensitive to pro-NGF mediated cell death as compared to wild-type Sortilin, since this pathway is disrupted.
iv) Application of the peptides (or derivatives of these) to the cell culture system for neuronal cell death, to verify that the peptides work as functional inhibitors.
v) Provided that identification of successful inhibitors can be performed, they could be utilized for rescue experiments in nerve lesions experiments for the rat brain.

Example 7

Binding Studies of Site Directed Mutants

Site-directed mutagenesis was performed for all important residues within the peptide sequence as identified by the substitution analysis in the SPOT method, using the pCepPU expression vector for sortilin as template. The thereby generated mutant constructs were used together with HEK293 cells to produce single residue mutants of the his-tagged sortilin luminal domain, to obtain the proteins R163A, F165A, R166A, F170A, K172A, and F174A numbered according to pro-Sortilin as specified in the sequence overview. As a control protein, the mutant R160A located N-terminally to the recognition sequence, was produced in order to have a protein with unaltered affinity for the NGF-pro-domain.

After purification by standard $Ni^{2+}$-NTA chromatography, each sortilin mutant was immobilized to a similar surface density on Biacore CM5 chips. Binding was tested using concentration series of the previously described GST-NGF-pro-domain fusion protein (Nykjaer et al., Nature 2004), which is able to render a higher response using the SPR system at low concentration. Thus concentration series of 10, 20, 30, 40, and 50 nM GST-pro-domain of NGF was applied to each chip surface, and data was fitted to a 1:1 binding model using the standard BIAevaluation software. Representative sensorgrams are presented in FIG. 21, and the binding parameters provided in Table 1 below.

TABLE 1

$R^{163}$IFRSSDFAKNF$^{174}$ (SEQ ID NO: 25, Residues 7-18)
Kinetic parameters for the binding reaction of GST-pro-dom-NGF (tested at 10-50 nM concentrations) to sortilin mutants as presented in FIG. 21. Binding curves were fitted using the BIAevaluation 3.1 software, showing that all produced single residue mutants exhibit a similar affinity towards the pro-neurotrophin domain as does the non-mutated receptor, although the F170A and F174A variants binds with a lower capacity as seen from the lower read out on the curves in FIG. 21. The numbering is according to pro-Sortilin as specified in the sequence overview.

| mutants | Site-directed PCR-clones | SEQ ID NO | 10 nM-50 nM series of sensorgrams | | |
|---|---|---|---|---|---|
| | | | ka | kd | KD |
| wt | RGGRIFRSSDFAKNF | 25 (Residues 4-18) | | | |
| R160A | AGGRIFRSSDFAKNF | 50 | $1.47 \times 10^5$ | $2.27 \times 10^{-4}$ | 1.89 nM |
| R163A | RGGAIFRSSDFAKNF | 51 | $1.85 \times 10^5$ | $4.21 \times 10^{-4}$ | 2.70 nM |
| F165A | RGGRIARSSDFAKNF | 52 | $1.10 \times 10^5$ | $4.22 \times 10^{-4}$ | 3.86 nM |
| R166A | RGGRIFASSDFAKNF | 53 | $6.48 \times 10^5$ | $2.85 \times 10^{-4}$ | 4.38 nM |

TABLE 1-continued

R$^{163}$IFRSSDFAKNF$^{174}$ (SEQ ID NO: 25, Residues 7-18)
Kinetic parameters for the binding reaction of GST-pro-dom-NGF (tested at
10-50 nM concentrations) to sortilin mutants as presented in FIG. 21.
Binding curves were fitted using the BIAevaluation 3.1 software, showing
that all produced single residue mutants exhibit a similar affinity towards
the pro-neurotrophin domain as does the non-mutated receptor, although the
F170A and F174A variants binds with a lower capacity as seen from the lower
read out on the curves in FIG. 21. The numbering is according
to pro-Sortilin as specified in the sequence overview.

| mutants | Site-directed PCR-clones | SEQ ID NO | 10 nM-50 nM series of sensorgrams | | |
|---|---|---|---|---|---|
| | | | ka | kd | KD |
| F170A | RGGPIFRSSDAAKNF | 54 | $1.30 \times 10^5$ | $5.91 \times 10^{-4}$ | 5.59 nM* |
| K172A | RGGRIFRSSDFAANF | 55 | $1.01 \times 10^5$ | $3.46 \times 10^{-4}$ | 3.91 nM |
| F174A | RGGRIFRSSDFAKNA | 56 | $2.35 \times 10^5$ | $1.03 \times 10^{-3}$ | 4.27 nM* |
| quatro | RGGAIAASSDAAKNF | 57 | | | no binding |

*these two mutants exhibit reduced binding capacity -- but similar affinity.

As described in the length analysis experiments, the peptide seem to carry two independent binding motives, one made by the RIFR (SEQ ID NO:25, residues 7-10) and one by FAKNF (SEQ ID NO:25, residues 14-18), as the small peptides RIFRSSDF (SEQ ID NO:25, residues 7-14:) and FAKNFVQTD (SEQ ID NO:25, residues 14-22) displayed efficient binding of the prodomain-NGF and pro-domain-BDNF in the SPOT analysis. This model is further supported by the previous data in the substitution analysis, where a stronger effect upon mutation was observed when using peptides containing only one of the binding motives, as compared to mutants spanning both motives. Accordingly, it was decided to "remove" an entire motif before substitution within the second motif and to be able to observe how that would influence binding of the ligand. A sortilin variant was produced containing quadruple substitutions (R163A, F165A, R166A, and 15 F170A) in a similar procedure using HEK293 cells as applied for single residue mutants. It was noticed that this protein was secreted into the medium of the HEK293 cells demonstrating that the quatro mutant was still able to fold into a soluble protein.

To determine ligand binding capacity, quatro protein was coupled in parallel to the wild-type sortilin on a new Biacore chip, and binding of GST-pro-NGF was measured in a manner similar to the analysis of single residue mutants (FIG. 21). A strongly reduced affinity for pro-neurotrophin domain binding was found, supporting the conclusion that a major binding site for the ligands is contained in the RGGRIFRSSDFAKNF peptide (SEQ ID NO:25, residues 4-18).

Binding of other ligands such as neurotensin and sortilin's own pro-peptide may be tested in a manner analogous to what is described herein above.

Example 8

Identification of Pro-Neurotrophin Binding Sites on the Sortilin Receptor

To identify antagonists for the neurotrophin pro-domain binding site in sortilin (i.e. the RGGRIFRSSDFAKNF peptide), the following set of experiments are performed:

Labeling of pro-NGF and the pro-dom-NGF is performed using the IODOGEN method and $^{125}$I from Amersham Biosciences. HEK293 cells are transfected with the sortilin expression vector using the HIFECT transfection reagent to optimize the efficiency. 24 hours post-transfection, cells are incubated at 4° C. for 2 hours before applying radio-ligand for 16 hours at 4° C. in 10 mM HEPES, pH 7.4 150 mM NaCl, 2 mM CaCl$_2$, and 1 mM MgCl$_2$ both in the absence and in the presence of candidate antagonists. Binding of ligand to sortilin is determined as cell-associated radioactivity. In a similar experiment conducted at 37° C., we will measure the amount of degraded ligand as counts secreted into the cell media over a time period of 16 hours. The ability of candidate antagonists to protect against pro-NGF induced apoptosis, is conducted as described (Jansen et al., Nature Neurosci., 2007).

The purification of the his-tagged sortilin extracellular domain is performed as described elsewhere, and coupled to the Nickel chelate (His-Tag) PS SPA Imaging scintillation beads according to the protocol of the manufacturer (GE Healthcare Life Sciences).

Single well homogenous assay is used for the direct quantitation of candidate agonist-induced or inverse induced $^{125}$I-pro-NGF or $^{125}$I-pro-dom-NGF binding activity for receptors coupled to the scintillation beads is performed by following guidelines as provided by GE Healthcare Life Sciences.

The antagonistic properties are tested in competition experiments using a scintillation proximity assay in a reverse setup. Prodomain of NGF fused to GST (described in Nykjcer, Nature, 2007) is coupled to Glutathione immobilized scintillation beads (GE Healthcare Life Sciences) and inhibition is determined using a radio-labeled $^{125}$I-RGGRIFRSSDFAKNF (SEQ ID NO:25, residues 4-AI or $^{125}$I-labeled intact sortilin extracellular domain binding to the beads by candidate antagonists as described above.

Antagonists binding directly to the RGGRIFRSSDFAKNF motif (as such molecules are very likely to interfere with the interaction of the particular ligand to intact sortilin) are identified. The peptide is synthesized by Eurogentec, Liege, Belgium, and immobilized to a CM5 biacore sensor chip (cat. no. BR-1000-14) using the NHS/EDC coupling kit (Biacore, Sweden). Binding properties of the candidate molecules are evaluated by screening their binding to the receptor/peptide at various concentrations in 10 mM HEPES, pH 7.4, 150 mM NaCl, 2 mM CaCl2, 0.005% Tween-20 as running buffer.

OVERVIEW OF SEQUENCES

SEQ ID NO 1: Sortilin
SEQ ID NO 2: SorLA

SEQ ID NO 3: SorCS1
SEQ ID NO 4: SorCS2
SEQ ID NO 5: SorCS3
SEQ ID NO 6: pre-pro-NGF
SEQ ID NO 7: pre-pro-BDNF
SEQ ID NO 8: Neurotrophin-3
SEQ ID NO 9: Neurotrophin-4/5
SEQ ID NO 10: Neurotensin (1-13)
SEQ ID NO 11: Neuromedin
SEQ ID NO 12: Receptor associated peptide (RAP)
SEQ ID NO 13: pro-Neurotensin/pro-Neuromedin
SEQ ID NO 14: NT(8-13)
SEQ ID NO 15: NT66L
SEQ ID NO 16: NT67L
SEQ ID NO 17: NT69L
SEQ ID NO 18: Eisai
SEQ ID NO 19: JMV-449
SEQ ID NO 20: PD-149163
SEQ ID NO 21: PD-149598
SEQ ID NO 22: PD-156425
SEQ ID NO 23: PD-156556
SEQ ID NO 24: CGX-1160
SEQ ID NO 25: Mature Sortilin G113-M143
   pro-Sortilin G157-M187
   pre-pro-Sortilin G190-M220
SEQ ID NO 26: Mature Sortilin R196-F207
   pro-Sortilin G163-M187
   pre-pro-Sortilin G196-M220
SEQ ID NO 27: Mature Sortilin G119-M122
   pro-Sortilin G163-M166
   pre-pro-Sortilin G196-M199
SEQ ID NO 28: Mature Sortilin G126-M130
   pro-Sortilin G170-M174
   pre-pro-Sortilin G203-M207
SEQ ID NO 29: PD-47113
SEQ ID NO 30: GZR-123
SEQ ID NO. 31: NT64D
SEQ ID NO. 32: NT64L
SEQ ID NO. 33: NT65L
SEQ ID NO. 34: NT66D
SEQ ID NO. 35: NT69L'
SEQ ID NO. 36: NT71
SEQ ID NO. 37: NT72
SEQ ID NO. 38: NT73
SEQ ID NO. 39: NT74
SEQ ID NO. 40: NT75
SEQ ID NO. 41: NT76
SEQ ID NO. 42: NT77
SEQ ID NO. 43: Signal peptide of Sortilin
SEQ ID NO. 44: SorCS2 peptide
SEQ ID NO. 45: Primer
SEQ ID NO. 46: Primer
SEQ ID NO. 47: Primer
SEQ ID NO. 48: Primer
SEQ ID NO. 49: Peptide containing fXa site and poly-histidine tag
SEQ ID NO. 50: R160A Site-Directed PCR clone
SEQ ID NO. 51: R163A Site-Directed PCR clone
SEQ ID NO. 52: F165A Site-Directed PCR clone
SEQ ID NO. 53: R166A Site-Directed PCR clone
SEQ ID NO. 54: F170A Site-Directed PCR clone
SEQ ID NO. 55: K172A Site-Directed PCR clone
SEQ ID NO. 56: F174A Site-Directed PCR clone
SEQ ID NO. 57: Quatro Site-Directed PCR clone

The invention claimed is:

1. A method of treating a neurological disease or a neural disorder comprising administering to a subject in need thereof a therapeutically effective amount of an antibody that binds to:
   (1) residues 7-10 (RIFR);
   (2) residues 14-18 (FAKNF); or
   (3) residues 7-10 (RIFR) and residues 14-18 (FAKNF);
   of a Sortilin receptor that consists of the amino acid sequence of SEQ ID NO:25, wherein:
   (i) said antibody inhibits binding of a pro-neurotrophin to a binding site on said Sortilin receptor, thereby treating said neurological disease or neural disorder; and
   (ii) said neurological disease or neural disorder is selected from the group consisting of Alzheimer's disease, Parkinson's disease, Huntington's chorea, stroke, nerve deafness, peripheral neuropathy, and Fabry's disease.

2. The method of claim 1, wherein the pro-neurotrophin is selected from the group consisting of pro-NGF (SEQ ID NO:6), pro-BDNF (SEQ ID NO:7), pro-NT-3 (SEQ ID NO:8), and pro-NT-4/5 (SEQ ID NO:9).

3. The method of claim 1, wherein said subject is a human being.

4. The method of claim 1, wherein said neurological disease or neural disorder is dementia associated with said Alzheimer's disease or Parkinson's disease.

5. The method of claim 1, wherein said antibody is administered in an amount of from about 1 μg/kg to about 100 mg/kg per day.

6. The method of claim 1, wherein said antibody is used in combination with a second active ingredient.

7. A method of treating nerve damage comprising administering to a subject in need thereof a therapeutically effective amount of an antibody that binds to:
   (1) residues 7-10 (RIFR);
   (2) residues 14-18 (FAKNF); or
   (3) residues 7-10 (RIFR) and residues 14-18 (FAKNF);
   of a Sortilin receptor that consists of the amino acid sequence of SEQ ID NO:25, wherein:
   (i) said antibody inhibits binding of a pro-neurotrophin to a binding site on a Sortilin receptor, thereby treating said nerve damage; and
   (ii) said nerve damage is caused by trauma, burns, kidney dysfunction, kidney injury, pancreatic dysfunction, pancreatic injury, lung dysfunction, lung injury, injury to fatty tissue, spinal cord injury, spinal cord trauma, diabetes, necrosis, loss of neurons, or the toxic effects of chemotherapeutics.

8. A method of treating a motor neuron disorder comprising administering to a subject in need thereof a therapeutically effective amount of an antibody that binds to:
   (1) residues 7-10 (RIFR);
   (2) residues 14-18 (FAKNF); or
   (3) residues 7-10 (RIFR) and residues 14-18 (FAKNF);
   of a Sortilin receptor that consists of the amino acid sequence of SEQ ID NO:25, wherein:
   (i) said antibody inhibits binding of a pro-neurotrophin to a binding site on a Sortilin receptor, thereby treating said motor neuron disorder; and
   (ii) said motor neuron disorder is selected from the group consisting of amyotrophic lateral sclerosis (Lou Gehrig's disease), and spinal muscular atrophy.

9. A method of treating pain or nociception comprising administering to a subject in need thereof a therapeutically effective amount of an antibody that binds to:
   (1) residues 7-10 (RIFR);
   (2) residues 14-18 (FAKNF); or
   (3) residues 7-10 (RIFR) and residues 14-18 (FAKNF);
   of a Sortilin receptor that consists of the amino acid sequence of SEQ ID NO:25; wherein said antibody inhibits binding of a pro-neurotrophin to a binding site on a Sortilin receptor, thereby treating said pain or nociception.

* * * * *

UNITED STATES PATENT AND TRADEMARK OFFICE
CERTIFICATE OF CORRECTION

PATENT NO.        : 8,748,384 B2
APPLICATION NO.   : 12/448422
DATED             : June 10, 2014
INVENTOR(S)       : Andersen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 61 days.

Signed and Sealed this

Twenty-ninth Day of September, 2015

Michelle K. Lee
*Director of the United States Patent and Trademark Office*